(12) United States Patent
Carlson-Stevermer et al.

(10) Patent No.: US 10,907,150 B2
(45) Date of Patent: Feb. 2, 2021

(54) MODIFIED GUIDE RNAS, CRISPR-RIBONUCLEOTPROTEIN COMPLEXES AND METHODS OF USE

(71) Applicant: WISCONSIN ALUMNI RESEARCH FOUNDATION, Madison, WI (US)

(72) Inventors: Jared Matthew Carlson-Stevermer, Madison, WI (US); Krishanu Saha, Middleton, WI (US); Amr Ashraf Abdeen, Madison, WI (US); Lucille Katherine Kohlenberg, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/008,376

(22) Filed: Jun. 14, 2018

(65) Prior Publication Data

US 2018/0362971 A1    Dec. 20, 2018

Related U.S. Application Data

(60) Provisional application No. 62/519,317, filed on Jun. 14, 2017.

(51) Int. Cl.
| | |
|---|---|
| *C12N 15/11* | (2006.01) |
| *C12N 15/10* | (2006.01) |
| *C12N 9/22* | (2006.01) |
| *C12N 15/90* | (2006.01) |

(52) U.S. Cl.
CPC ............ *C12N 15/11* (2013.01); *C12N 9/22* (2013.01); *C12N 15/102* (2013.01); *C12N 15/907* (2013.01); *C12N 15/111* (2013.01); *C12N 2310/16* (2013.01); *C12N 2310/20* (2017.05); *C12N 2310/3519* (2013.01); *C12N 2800/80* (2013.01)

(58) Field of Classification Search
CPC ............ C12N 2310/16; C12N 2310/20; C12N 15/102; C12N 2310/3519
See application file for complete search history.

(56) References Cited

U.S. PATENT DOCUMENTS

| | | |
|---|---|---|
| 8,889,418 B2 | 11/2014 | Zhang et al. |
| 9,856,497 B2 | 1/2018 | Qi et al. |
| 9,868,962 B2 | 1/2018 | May et al. |
| 10,377,998 B2 | 8/2019 | Zhang et al. |
| 10,450,584 B2 | 10/2019 | Barrangou et al. |
| 2015/0283265 A1* | 10/2015 | Peyman ............ A61K 47/6923 424/491 |
| 2017/0081650 A1 | 3/2017 | Joung et al. |
| 2017/0152508 A1 | 7/2017 | Joung et al. |
| 2020/0140858 A1 | 5/2020 | Saha et al. |

FOREIGN PATENT DOCUMENTS

WO    2016183402 A2    11/2016

OTHER PUBLICATIONS

Darmostuk et al. Current approaches in SELEX: An update to aptamer selection technology. Biotechnology Advances, vol. 33, pp. 1141-1161, 2015. (Year: 2015).*
Zetsche et al. Nature Biotechnology, vol. 33, No. 2, pp. 139-142, Feb. 2015, including pp. 1-9 of Supplementary Information. (Year: 2015).*
pp. 1-37 of Supplementary Information of Shechner et al. Nature Methods, vol. 12, No. 7, pp. 664-670, and pp. 1-5 of Online Methods, 2015, which is cited as reference 31 on the IDS filed Aug. 21, 2018. (Year: 2015).*
Walker et al. Chapter 26. Jeffrey E. Gerst (ed.), RNA Detection and Visualization: Methods and Protocols, Methods in Molecular Biology, vol. 714, Springer Science+Business Media, LLC, 2011, pp. 423-444. (Year: 2011).*
Carlson-Stevermer et al.; "Assembly of CRISPR Ribonucleoproteins With Biotinylated Oligonucleotides via an RNA Aptamer for Precise Gene Editing"; Nature Communications; 8(1); 13 pages; (2017).
International Search Report and Written Opinion; International Application No. PCT/US2018/037531; International filing date Jun. 14, 2018; dated Sep. 6, 2018; 18 pages.
Lee et al.; "Synthetically Modified Guide RNA and Donor DNA are a Versatile Platform for CRISPR-Cas9 Engineering"; ELIFE; 6; 17 pages; (2017).
Ming et al.; "Efficient Generation of Mice Carrying Homozygous Double-floxp Alleles Using the Cas9-Avidin/Biotin-Donor DNA System"; Cell Research; 27; pp. 578-581; (2017).
Bao et al.; "Multifunctional Nanoparticles for Drug Delivery and Molecular Imaging"; Annu. Rev. Biomed. Eng.; 15; pp. 253-282; (2013).
Brinkman et al.; "Easy Quantitative Assessment of Genome Editing by Sequence Trace Decomposition"; Nucleic Acids Research; 8 pages, (2014), downloaded from https://academic.oup.com/nar/article-abstract/42/22/e168/2411890, by University of Wisconsin—Madison on Jul. 5, 2018.
Carlson-Stevermer et al.; "High-Content Analysis of CRISPR-Cas9 Gene-Edited Human Embryonic Stem Stem Cells"; Stem Cell Reports; 6; pp. 109-120; (2016).
Chu et al.; "Increasing the Efficiency of Homology-Directed Repair for CRISPR-Cas9-Induced Precise Gene Editing in Mammalian Cells"; Nature Biotechnology; 33(5); pp. 543-550; (2015).
Davis et al.; "Small Molecule-Triggered Cas9 Protein With Improved Genome-Editing Specificity"; Nature Chemical Biology; vol. 11, pp. 316-318; (2015).

(Continued)

*Primary Examiner* — Jennifer Dunston
(74) *Attorney, Agent, or Firm* — Cantor Colburn LLP

(57) ABSTRACT

Described herein are modified guide RNAs such as a single guide RNA including, from 5' to 3', a single-stranded protospacer sequence, a first complementary strand of a binding region for the Cas9 polypeptide, an aptamer that binds a biotin-binding molecule, and a second complementary strand of the binding region for the Cas9 polypeptide. Also described is an RNP complex including the modified guide RNA and a Cas9 polypeptide or active fragment thereof. Also included are methods of modifying target genes in cells using the modified guide RNAs.

37 Claims, 31 Drawing Sheets
(19 of 31 Drawing Sheet(s) Filed in Color)
Specification includes a Sequence Listing.

(56) References Cited

OTHER PUBLICATIONS

De Ravin et al.; "CRISPR-Cas9 Gene Repair of Hematopoietic Stem Cells From Patients with X-Linked Chronic Granulomatous Disease"; Sci. Transl. Med.; 9; eaah3480; 10 pages; (2017).
Dever et al.; "CRISPR/Cas9 Beta-globin Gene Targeting in Human Haematopoietic Stem Cells"; Nature; vol. 539; 384, 19 pages; (2016).
DeWitt et al.; "Selection-Free Genome Editing of the Sickle Mutation in Human Adult Hematopoietic Stem/Progenitor Cells"; Sci. Transl. Med.; 8; 360ra134; 9 pages; (2016).
Duda et al.; "High-Efficiency Genome Editing via 2A-Coupled Co-Expression of Fluorescent Proteins and Zinc Finger Nucleases or CRISPR/Cas9 Nickase Pairs"; Nucleic Acids Research; 42(10);; e84; 16 pages; (2014); downloaded from https://academic.oup.com/nar/article-abstract/42/10/e84/2434652 by University of Wisconsin—Madison Libraries on Jul. 5, 2018.
Eyquem et al.; "Targeting a Car to the Trac Locus With CRISPR/Cas9 Enhances Tumour Rejection"; Nature; vol. 543; p. 113; 19 pages.; (2017).
Gaj et al.; "Targeted Gene Knock-In by Homology-Directed Genome Editing Using Cas9 Ribonucleoprotein and AAV Donor Delivery"; Nucleic Acids Research; 45(11); e98; 11 pages, Downloaded from https://academic.oup.com/nar/article-abstract/45/11/398/3059660 by University of Wisconsin—Madison on Jul. 5, 2018.
Hemphill et al.; "Optical Control of CRISPR/Cas9 Gene Editing"; J. Am. Chem. Soc.; 137; pp. 5642-5645; (2015).
Kleinstiver et al.; "High-Fidelity CRISPR-Cas9 Nucleases With No Detectable Genome-Wide Off-Target Effects"; Nature; 529; pp. 490; 17 pages; (2016).
Konermann et al.; "Genome-Scale Transcriptional Activation by an Engineered CRISPR-Cas9 Complex"; Nature; vol. 517; p. 583-585; (2015).
Landrum et al.; "ClinVar: Public Archive of Interpretations of Clinically Relevant Variants"; D862-D868 Nucleic Acids Research; vol. 44, pp. D862-D868; Database issue; (2016).
Le Trong et al.; "Streptavidin and Its Biotin Complex at Atomic Resolution"; Acta Cryst.; D67; pp. 813-821; (2011).
Leppek et al.; "An Optimized Streptavidin-Binding RNA Aptamer for Purification of Ribonucleoprotein Complexes Identifies Novel ARE-Binding Proteins"; Nucleic Acids Research; vol. 42(2); e13; 15 pages; (2014), downloaded from https://academic.oup.com/nar/article-abstract/42/2/e13/1030103 by University of Wisconsin—Madison Libraries on Jul. 5, 2018.
Li et al.; "Optimization of Genome Engineering Approaches With the CRISPR/Cas9 System"; PLoS One; 9(8): doi:10.1371/journal.pone.0105779; (2014) e105779.
Liang et al.; "Enhanced CRISPR/Cas9-Mediated Precise Genome Editing by Improved Design and Delivery of gRNA, Cas9 Nuclease, and Donor DNA"; Journal of Biotechnology; 241; pp. 136-146; (2017).
Lin et al.; "Enhanced Homology-Directed Human Genome Engineering by Controlled Timing of CRISPR/Cas9 Delivery"; Weigel D, ed. eLife.; 32 pages; (2014) ;3:e04766. doi:10.7554/eLife.04766.
Lonowski et al.; "Genome Editing Using FACS Enrichment of Nuclease-Expressing Cells and Indel Detection by Amplicon Analysis"; Nature Protocols; 12(3); pp. 581-603; (2017).
Ma et al.; "Efficient Generation of Mice Carrying Homozygous Double-Floxp Alleles Using the Cas9-Avidin/Biotin Donor DNA System"; Cell Research; 27; pp. 578-581; (2017).
Maruyama et al.; "Increasing the Efficiency of Precise Genome Editing With CRISPR-Cas9 by Inhibition of Nonhomologous End Joining" Nature Biotechnology; 33(5); p. 538; 9 pages; (2015).
Merkle et al.; "Efficient CRISPR-Cas9-Mediated Generation of Knockin Human Pluripotent Stem Cells Lacking Undesired Mutations at the Targeted Locus": Cell Reports; 11; pp. 875-883; (2015).
Nishimasu et al.; "Crystal Structure of Cas9 in Complex with Guide RNA and Target DNA"; Cell; 156; pp. 935-949; (2014).
Paquet et al.; "Efficient Introduction of Specific Homozygous and Heterozygous Mutations Using CRISPR/Cas9"; Nature; 533; p. 125; 18 pages; (2016).
Pattanayak et al.; "High-Throughput Profiling of Off-Target DNA Cleavage Reveals RNA-Programmed Cas9 Nuclease Specificity"; Nature Biotechnology; 31(9); pp. 839-845; (2013).
Ran et. al.; "Genome Engineering Using the CRISPR-Cas9 System"; Nature Protocols; 8(11); pp. 2281-2308; (2013).
Richardson et al.; "Enhancing Homology-Directed Genome Editing by Catalytically Active and Inactive CRISPR-Cas9 Using Asymmetric Donor DNA"; Nature Biotechnology; 34(3); pp. 339-345; (2016).
Sevier et al.; "Formation and Transfer of Disulphide Bonds in Living Cells"; Nature Reviews; Molecular Cell Biology; 3; pp. 836-847; (2002).
Shechner, et al.; "Multiplexable, Locus-Specific Targeting of Long RNAs With CRISPR-Display"; Nature Methods; 12(7); p. 664; 12 pages (2015).
Song et al; "RS-1 Enhances CRISPR/Cas9- and TALEN-Mediated Knock-In Efficiency"; Nature Communications 7 pages; Article No. 10548; (2016).
Steyer et al.; "Scarless Genome Editing of Human Pluripotent Stem Cells via Transient Puromycin Selection"; Stem Cell Reports; 10; pp. 642-654; (2018).
Yang et al.; "Optimization of Scarless Human Stem Cell Genome Editing"; Nucleic Acids Research; 41(19); pp. 9049-9061; (2013).
Zuris et al.; "Cationic Lipid-Mediated Delivery of Proteins Enables Efficient Protein-Based Genome Editing In Vitro and In Vivo"; Nature Biotechnology; 33(1); pp. 73-80; (2015).
Ellington et al.; "In Vitro Selection of RNA Molecules That Bind Specific Ligands"; Nature; 346; pp. 818-822; (1990).
Ruigrok et al., "Kinetic and Stoichiometric Characterisation of Streptavidin-Binding Apramers"; ChemBioChem; 13; pp. 829-836; (2012).
Srisawat et al.; "SteptavidinAptamers: Affinity Tags for the Study of RNAs and Ribonucleoproteins"; RNA; 7; pp. 632-641; (2001).
Wang et al.; "In Vitro Selection of High-affinity DNA Aptamers for Streptavidin"; Acta Biochim Biophys Sin; 41(4); pp. 335-340; (2009).
Chen et al.; "Enhanced proofreading governs CRISPR-Cas9 targeting accuracy"; Nature, vol. 550, Issue No. 7676; 2017; doi:10.1038/nature24268; pp. 407-422.
Chew et al.; "A multifunctional AAV-CRISPR-Cas9 and its host response"; Nature Methods, vol. 13, Issue No. 10; 2016; doi:10.1038/nmeth.3993; pp. 868-879.
Hasegawa et al.; "Methods for Improving Aptamer Binding Affinity"; Molecules, vol. 21, Issue No. 4; 2016; doi:10.3390/molecules21040421; pp. 421-435.
Hernandez et al.; "Aptamers as a model for functional evaluation of LNA and 20-amino LNA"; Bioorganic & Medicinal Chemistry Letters, vol. 19, Issue 23; 2007; doi:10.1016/j.bmcl.2009.10.039; pp. 6585-6587.
Hernandez et al.; "Label free optical sensor for Avidin based on single gold nanoparticles functionalized with aptamers"; Journal of Biophotonics, vol. 2, Issue No. 4; 2009; DOI 10.1002/jbio.200910006; pp. 227-231.
Lorenz et al.; "Genomic systematic evolution of ligands by exponential enrichment (Genomic SELEX) for the identification of protein-binding RNAs independent of their expression levels"; Nature Protocols, vol. 1, Issue No. 5; 2006; doi:10.1038/nprot.2006.372; pp. 2204-2212.
Ma et al.; "Rational Design of Mini-Cas9 for Transcriptional Activation"; ACS Synthetic Biology, vol. 7, Issue No. 4; 2018; DOI: 10.1021/acssynbio.7b00404; pp. 978-985.
Stoltenburg et al.; "FluMag-SELEX as an advantageous method for DNA aptamer selection"; Analytical and Bioanalytical Chemistry, vol. 383, Issue No. 1; 2005; DOI 10.1007/s00216-005-3388-9; pp. 83-91.
Stoltenburg et al.; "SELEX—a (r) evolutionary method to generate high-affinity nucleic acid ligands"; Biomolecular Engineering, vol.

(56) References Cited

OTHER PUBLICATIONS

24, Issue No. 4; 2007; doi:10.1016/j.bioeng.2007.06.001; pp. 381-403.

* cited by examiner

SEQ ID NO: 1

SEQ ID NO: 2

SEQ ID NO: 3

SEQ ID NO: 70

US 10,907,150 B2

MODIFIED GUIDE RNAS, CRISPR-RIBONUCLEOTPROTEIN COMPLEXES AND METHODS OF USE

CROSS-REFERENCE TO RELATED APPLICATIONS

This application claims priority to U.S. Provisional Application 62/519,317 filed on Jun. 14, 2017, which is incorporated herein by reference in its entirety.

FEDERAL FUNDING STATEMENT

This invention was made with government support under GM119644 awarded by the National Institutes of Health and CBET1350178 awarded by the National Science Foundation. The government has certain rights in the invention.

FIELD OF THE DISCLOSURE

The present disclosure is related to modified guide RNAs and CRISPR-ribonucleoprotein complexes containing the modified guide RNAs and their use in genome editing methods.

BACKGROUND

Precise editing of DNA sequences in the human genome can be used to correct mutations or introduce novel genetic functionality for many biomedical purposes. Specifically, nonviral delivery of pre-formed CRISPR ribonucleoproteins (RNPs) is currently being developed for somatic gene editing applications. RNPs combining *Streptococcus pyogenes* Cas9 nuclease (Sp.Cas9, a high-affinity nuclease isolated from a type II CRISPR-associated system) and a single-guide RNA (sgRNA), for example, generate on-target DNA double strand breaks (DSBs) with little to no off-target DNA cleavage. This break can be repaired through error prone non-homologous end joining (NHEJ) or precise homology directed repair (HDR), in which a template is used. Co-delivery of a nucleic acid donor template with the Sp.Cas9 RNP (Sp.Cas9+sgRNA) is capable of producing precise edits at target loci through HDR of the DSB. However, variable delivery of the CRISPR system along with the donor templates generates a spectrum of edits, where a majority of cells include imprecise insertions and deletions (indels) of DNA bases from NHEJ repair of the DSB. Even when precise HDR of the DSB occurs on one allele, there is a chance that both alleles in diploid cells are not identically edited, resulting in imprecise edits on the other allele. Faithful writing of DNA, or scarless gene editing, within human cells remains an outstanding challenge.

Strategies to promote precise editing include addition of small molecules to block NHEJ and restricting Sp.Cas9 activity to particular phases of the cell cycle, but variability and toxicity has been observed across human cell lines when applying small molecules to promote HDR. Also, selection strategies through viral integration and excision of drug or cell-surface selection cassettes, flow cytometry for co-expressed fluorescent protein, or through transient drug selection can assist in the isolation of cells with one or two precisely-edited alleles. For all of these strategies, imprecise editing through NHEJ typically outnumbers precise HDR outcomes. None of the current strategies precisely control the delivery of the RNP with the donor template, and many resort to 'flooding' the cell with high Cas9 expression and/or the donor template.

What is needed are new strategies for genome editing that have improved editing fidelity.

BRIEF SUMMARY

In one aspect, a modified guide RNA, comprises
a crRNA comprising a single-stranded protospacer sequence, and a first complementary strand of a binding region for the Cas9 polyp eptide, and
a tracrRNA comprising, a second complementary strand of the binding region for the Cas9 polypeptide,
wherein the crRNA or the tracrRNA comprises an aptamer that binds a biotin-binding molecule,
wherein the crRNA and the tracrRNA hybridize through the first and second complementary strands of the binding region for the Cas9 polypeptide.

In another aspect, a modified sg RNA comprises, from 5' to 3',
a single-stranded protospacer sequence,
a first complementary strand of a binding region for the Cas9 polypeptide,
an aptamer that binds a biotin-binding molecule, and a second complementary strand of the binding region for the Cas9 polypeptide.

In another aspect, an RNP complex comprises the modified guide RNA such as the sgRNA and a Cas9 polypeptide or active fragment thereof.

In another aspect, a method of modifying a target gene in a cell comprises delivering to the cell the RNP complex described above, wherein the single-stranded protospacer sequence of the modified guide RNA such as the sgRNA hybridizes to a sequence in the target gene to be modified.

In another aspect, a method of modifying a target gene in a cell comprises delivering to the cell the modified guide RNA described above, wherein the modified guide RNA is associated with a biotin-binding molecule, and wherein the single-stranded protospacer sequence of the modified guide RNA hybridizes to a sequence in the target gene to be modified.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19 shows absolute NHEJ (orange diamonds) and HDR percentages (purple diamonds) as a function of total reads at two different loci in hPSCs using different ssODN designs. Each symbol represents a single replicate analyzed by deep sequencing 4 days after nucleofection into hPSCs. HDR levels were generally higher in each replicate than NHEJ levels.

FIG. 20 shows the ratio of HDR:indel reads in deep sequencing using each ssODN combined with S1mplexes. Blue circles represent individual biological replicates. With each ssODN, S1mplexes increased the ratio of HDR:indel when compared to sgRNA controls but no significant trends as to symmetry, sidedness, or biotin location were observed.

FIG. 33a shows a biotin-ssODN that contained a UV-cleavable linker was attached to streptavidin and S1mplex particles in order to study the potential of releasing the ssODN inside the cell to promote HDR. Lane 1: DNA standard. Lane 2: Photo-cleavable biotin-ssODN. Lane 3: standard ssODN. Lane 4: Binary complexes of streptavidin and photo-cleavable biotin-ssODNs. Lane 5-6: Binary complexes cleaved by either exposure to light through a DAPI filter cube (lane 5) or exposure to a UV transilluminator (lane 6). DAPI filter cube cleaved nearly all ssODN after 10 minutes whereas transilluminator had complete cleavage. Cleaved DNA product was the same length as control standard ssODN. FIG. 33b shows release of biotin-ssODN by 15 minutes of light exposure through a DAPI filter cube every hour post transfection. Levels of HDR were not significantly affected by the release of the ssODN within the cell at any time point (n=3 biological replicates).

The above-described and other features will be appreciated and understood by those skilled in the art from the following detailed description, drawings, and appended claims.

DETAILED DESCRIPTION

Figure 1:
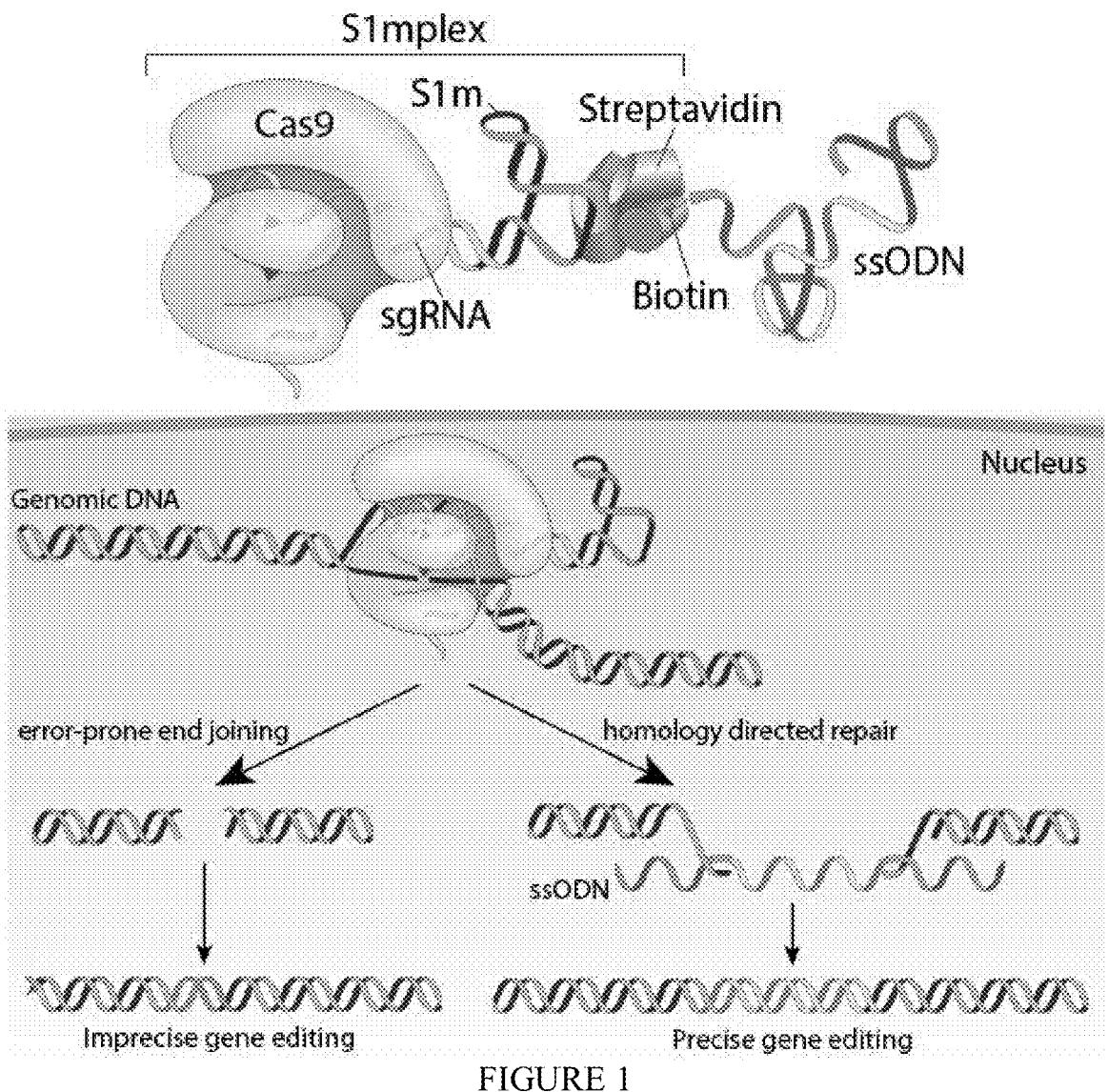
FIG. 1 is a schematic showing assembled ssODN-S1mplexes which are complexes of Sp.Cas9 protein, sgRNA with S1m aptamer, streptavidin, and a single-stranded oligodeoxynucleotide (ssODN) donor template. S1m-sgRNAs add an RNA aptamer at the first stem loop of the sgRNA that is capable of binding streptavidin protein. A biotin-ssODN is then added to this tertiary complex. ssODN-S1mplex particles are designed to promote homology directed repair (HDR).

Described herein are modified guide RNAs such as sgRNAs and their RNP complexes with Cas9. Without being held to theory, the inventors hypothesized that some of the errors in gene editing outcomes could be reduced by preassembling RNPs with donor template or other moieties that enable the isolation of precisely-edited cells (FIG. 1). The inventors designed a strategy inspired by CRISPR display that leverages structural studies of the RNP to identify locations in the guide RNA sequence where RNA aptamers could be tolerated.

The S1mplex tool described here exploits high affinity interactions between a short RNA aptamer and streptavidin to promote more faithful writing of the human genome. In an aspect, these RNP-containing complexes can be assembled outside the cell to a desired stoichiometry and delivered as an all-in-one gene-editing nanoparticle together with a donor nucleic acid template. In addition, the complexes can be easily decorated with additional moieties such as fluorophores or Qdots to enrich for edited cells. Use of these particles with a biotinylated ssODN reduced heterogeneity in delivery among RNPs and nucleic acids within human cells and enriches the ratio of precisely-edited to imprecisely-alleles edited alleles up to 18-fold higher than standard RNP methods, approaching a ratio of four precise edits to every one imprecise edit. Further functionalization with a unique fluorophore enables multiplexed editing and enrichment of precisely edited populations through cell sorting. Taken together, advances with the S1mplex tool generates new, chemically-defined reagents to promote precise editing of the human genome.

Figure 2:
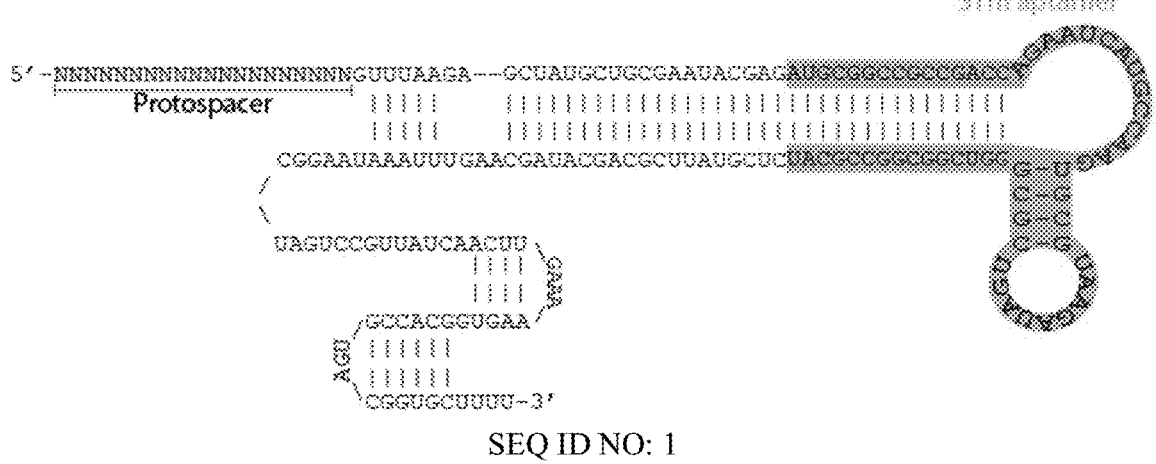
FIG. 2 shows the predicted secondary structure of S1m-sgRNA. Protospacer designates the region that defines the sequence to target in the human genome. S1m stem loop (coral) binds streptavidin.

The inventors devised a strategy inspired by CRISPR display that leverages structural studies of the RNP to identify locations in the sgRNA sequence where RNA aptamers could be tolerated (FIG. 1). Three sgRNAs with a modification either in a stem loop of the sgRNA or at the 3' end were designed (FIG. 2), as these locations have previously been shown to tolerate additions with a minimal loss in Cas9 binding activity. Separately, at each location, a perfectly complementary 10 nucleotide block was added which was previously shown to aid aptamer addition to sgRNAs and a 60 nucleotide S1m aptamer, which has a strong non-covalent interaction with streptavidin. The added sequence extends the sgRNA stem loop and contains two distinct bulges used for binding. We termed these new sgRNAs S1m-sgRNA-1, S1m-sgRNA-2, and S1m-sgRNA-3 in reference to their position in the sgRNA from 5' to 3' (FIG. 2).

CRISPR refers to the Clustered Regularly Interspaced Short Palindromic Repeats type II system used by bacteria and archaea for adaptive defense. This system enables bacteria and archaea to detect and silence foreign nucleic acids, e.g., from viruses or plasmids, in a sequence-specific manner. In type II systems, guide RNA interacts with Cas9 and directs the nuclease activity of Cas9 to target DNA sequences complementary to those present in the guide RNA. Guide RNA base pairs with complementary sequences in target DNA. Cas9 nuclease activity then generates a double-stranded break in the target DNA.

CRISPR/Cas9 is an RNP complex. CRISPR RNA (crRNA) includes a 20 base protospacer element that is complementary to a genomic DNA sequence as well as additional elements that are complementary to the transactivating RNA (tracrRNA). The tracrRNA hybridizes to the crRNA and binds to the Cas9 protein, to provide an active RNP complex. Thus, in nature, the CRISPR/Cas9 complex contains two RNA species.

sgRNA refers to a single RNA species which combines the tracrRNA and the crRNA and is capable of directing Cas9-mediated cleavage of target DNA. An sgRNA thus contains the sequences necessary for Cas9 binding and nuclease activity and a target sequence complementary to a target DNA of interest (protospacer sequence). In general, in an sgRNA, the tracrRNA and the crRNA are connected by a linker loop sequence. sgRNAs are well-known in the art. While sgRNA is generally used throughout this disclosure, two-part guide RNAs containing a crRNA and a tracrRNA can also be employed.

As used herein, a guide RNA protospacer sequence refers to the nucleotide sequence of a guide RNA that binds to a target DNA sequence and directs Cas9 nuclease activity to the target DNA locus. In some embodiments, the guide RNA protospacer sequence is complementary to the target DNA sequence. As described herein, the protospacer sequence of a single guide RNA may be customized, allowing the targeting of Cas9 activity to a target DNA of interest.

Any desired target DNA sequence of interest may be targeted by a guide RNA target sequence. Any length of target sequence that permits CRISPR-Cas9 specific nuclease activity may be used in a guide RNA. In some embodiments, a guide RNA contains a 20 nucleotide protospacer sequence.

In addition to the protospacer sequence, the targeted sequence includes a protospacer adjacent motif (PAM) adjacent to the protospacer region which is a sequence recognized by the CRISPR RNP as a cutting site. Without wishing to be bound to theory, it is thought that the only requirement for a target DNA sequence is the presence of a protospacer-adjacent motif (PAM) adjacent to the sequence complementary to the guide RNA target sequence. Different Cas9 complexes are known to have different PAM motifs. For example, Cas9 from *Streptococcus pyogenes* has a NGG trinucleotide PAM motif; the PAM motif of *N. meningitidis* Cas9 is NNNNGATT; the PAM motif of *S. thermophilus* Cas9 is NNAGAAW; and the PAM motif of *T. denticola* Cas9 is NAAAAC.

A modified guide RNA is a one-part or two-part RNA capable of directing Cas-9-mediated cleavage of target DNA. A modified sg RNA is a single RNA species capable of directing Cas9-mediated cleavage of target DNA. A modified sgRNA, for example, comprises sequences that provide Cas9 nuclease activity, a protospacer sequence complementary to a target DNA of interest, and an aptamer that binds a biotin-binding molecule. The inventors of the present application unexpectedly found that the linker loop that connects the tracrRNA and the crRNA in an sgRNA can be replaced with an aptamer that binds a biotin-binding molecule such as a streptavidin-binding aptamer. Unexpectedly, the modified sgRNAs can bind both Cas9 protein and streptavidin, and form active RNP complexes which induce error-prone DNA repair less frequently than standard CRISPR-Cas9 RNP complexes.

In an aspect, a modified guide RNA, comprises
a crRNA comprising a single-stranded protospacer sequence and a first complementary strand of a binding region for the Cas9 polypeptide, and
a tracrRNA comprising a second complementary strand of the binding region for the Cas9 polypeptide,
wherein the crRNA or the tracrRNA comprises an aptamer that binds a biotin-binding molecule, wherein the crRNA and the tracrRNA hybridize through the first and second complementary strands of the binding region for the Cas9 polypeptide.

In another aspect, the crRNA and the tracrRNA form an sgRNA, the sgRNA comprise from 5' to 3',
the single-stranded protospacer sequence,
the first complementary strand of a binding region for the Cas9 polypeptide,
the aptamer that binds a biotin-binding molecule, and
the second complementary strand of the binding region for the Cas9 polypeptide.

More specifically, a modified sgRNA comprises, from 5' to 3', a single-stranded protospacer sequence, a first complementary strand of a binding region for the Cas9 polypeptide, an aptamer that binds a biotin-binding molecule, and a second complementary strand of the binding region of the Cas9 protein. In an embodiment, in the secondary structure of the modified sgRNA, the stem forms a stem-loop structure with the aptamer that binds the biotin-binding molecule. Specific modified sgRNAs are provided in FIG. 2.

The single-stranded protospacer region can comprise 17 to 20 nucleotides. Exemplary binding regions for Cas9 polypeptides comprise 10 to 35 base pairs.

In an aspect, the aptamer that binds a biotin-binding molecule forms a stem-loop structure. The stem portion of the stem-loop structure optionally forms a contiguous double strand with the double-stranded binding region for the Cas9 polypeptide. The stem portion of the aptamer can comprise 9 to 15 base pairs, while the loop comprises 30 nucleotides. As shown in FIG. 2, the aptamer may contain more than one stem-loop structure. As shown in Example 9, the length of the stem portion of the aptamer is not critical and can be adjusted depending on the application of the modified guide RNA.

Also included herein is an RNP complex comprising the modified guide RNA, e.g., sgRNA, and a Cas9 polypeptide or active fragment thereof. Exemplary modified sgRNAs include:

(SEQ ID NO: 1)
NNNNNNNNNNNNNNNNNNNNGUUUAAGAGCUAUGCUGCGAAUACGAGA

UGCGGCCGCCGACCAGAAUCAUGCAAGUGCGUAAGAUAGUCGCGGGUC

GGCGGCCGCAUCUCGUAUUCGCAGCAUAGCAAGUUUAAAUAAGGCUAG

UCCGUUAUCAACUUGAAAAAGUGGCACCGAGUCGGUGCUUUU;

(SEQ ID NO: 2)
NNNNNNNNNNNNNNNNNNNNGUUUAAGAGCUAUGCUGGAAACAGCAUA

GCAAGUUUAAAUAAGGCUAGUCCGUUAUCAACUUCGAAUACGAGAUGC

GGCCGCCGACCAGAAUCAUGCAAGUGCGUAAGAUAGUCGCGGGUCGGC

GGCCGCAUCUCGUAUUCGGAAAAAGUGGCACCGAGUCGGUGCUUUU;
or (SEQ ID NO: 3)
NNNNNNNNNNNNNNNNNNNNGUUUAAGAGCUAUGCUGGAAACAGCAUA

GCAAGUUUAAAUAAGGCUAGUCCGUUAUCAACUUGAAAAAGUGGCACC

GAGUCGGUGCCGAAUACGAGAUGCGGCCGCCGACCAGAAUCAUGCAAG

UGCGUAAGAUAGUCGCGGGUCGGCGGCCGCAUCUCGUAUUCGUUUU;
or (SEQ ID NO: 70)
NNNNNNNNNNNNNNNNNNNNGUUUAAGAGCUAUGCUGCGAAUACGAGC

CGCCGACCAGAAUCAUGCAAGUGCGUAAGAUAGUCGCGGGUCGGCGGC

UCGUAUUCGCAGCAUAGCAAGUUUAAAUAAGGCUAGUCCGUUAUCAAC

UUGAAAAAGUGGCACCGAGUCGGUGCUUUU

A "Cas9" polypeptide is a polypeptide that functions as a nuclease when complexed to a guide RNA, e.g., an sgRNA or modified sgRNA. The Cas9 (CRISPR-associated 9, also known as Csn1) family of polypeptides, for example, when bound to a crRNA:tracrRNA guide or single guide RNA, are able to cleave target DNA at a sequence complementary to the sgRNA target sequence and adjacent to a PAM motif as described above. Cas9 polypeptides are characteristic of type II CRISPR-Cas systems. The broad term "Cas9" Cas9 polypeptides include natural sequences as well as engineered Cas9 functioning polypeptides. The term "Cas9 polypeptide" also includes the analogous Clustered Regularly Interspaced Short Palindromic Repeats from *Prevotella* and *Francisella* 1 or CRISPR/Cpf1 which is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. Additional Class I Cas proteins include Cas3, Cas8a, Cas5, Cas8b, Cas8c, Cas 10d, Case1, Cse 2, Csy 1, Csy 2, Csy 3, GSU0054, Cas 10, Csm 2, Cmr 5, Cas10, Csx11, Csx10, and Csf 1. Additional Class 2 Cas9 polypeptides include Csn 2, Cas4, C2c1, C2c3 and Cas13a.

Exemplary Cas9 polypeptides include Cas9 polypeptide derived from *Streptococcus pyogenes*, e.g., a polypeptide having the sequence of the Swiss-Prot accession Q99ZW2 (SEQ ID NO: 5); Cas9 polypeptide derived from *Streptococcus thermophilus*, e.g., a polypeptide having the sequence of the Swiss-Prot accession G3ECR1 (SEQ ID NO: 6); a Cas9 polypeptide derived from a bacterial species within the genus *Streptococcus*; a Cas9 polypeptide derived from a bacterial species in the genus *Neisseria* (e.g., GenBank accession number YP_003082577; WP_015815286.1 (SEQ ID NO: 7)); a Cas9 polypeptide derived from a bacterial species within the genus *Treponema* (e.g., GenBank accession number EMB41078 (SEQ ID NO: 8)); and a polypeptide with Cas9 activity derived from a bacterial or archaeal species. Methods of identifying a Cas9 protein are known in the art. For example, a putative Cas9 protein may be complexed with crRNA and tracrRNA or sgRNA and incubated with DNA bearing a target DNA sequence and a PAM motif.

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). In some embodiments, a Cas9 nuclease has an inactive (e.g., an inactivated) DNA cleavage domain, that is, the Cas9 is a nickase. Other embodiments of Cas9, both DNA cleavage domains are inactivated. This is referred to as catalytically-inactive Cas9, dead Cas9, or dCas9.

Functional Cas9 mutants are described, for example, in US20170081650 and US20170152508, incorporated herein by reference for its disclosure of Cas9 mutants.

In addition, to the modified sgRNA and the Cas9 polypeptide or active fragment thereof, an RNP complex may further comprise a biotin-binding molecule such as an avidin such as avidin, streptavidin, or NeutrAvidin™ which bind with high affinity to the aptamer that binds the biotin-binding molecule in the modified sgRNA. Avidin, streptavidin and NeutrAvidin™ are a tetramers and each subunit can bind biotin with equal affinity. Avidin, streptavidin and NeutrAvidin™ variants that contain one, two or three biotin binding sites are also available and may be employed in the complex.

When the RNP complex comprises a biotin-binding molecule, the complex can further comprise a biotinylated molecule which associates with the complex via the biotin-binding molecule. The biotinylated molecule can target the RNP complex to a specific cell type, organ or tissue. For example, PEG-coated gold nanoparticles exhibit size-dependent in vivo toxicity; the renal clearance of quantum dots can be controlled; and the accumulation of PEGylated silane-coated magnetic iron oxide nanoparticles has been shown to be size dependent.

In one embodiment, the biotinylated molecule is a biotinylated oligodeoxynucleotide, such as a biotinylated donor DNA template. Homologous recombination can insert an exogenous polynucleotide sequence into the target nucleic acid cleavage site. An exogenous polynucleotide sequence can be called a donor polynucleotide or a donor sequence. In some embodiments, a donor polynucleotide, a portion of a donor polynucleotide, a copy of a donor polynucleotide, or a portion of a copy of a donor polynucleotide can be inserted into a target nucleic acid cleavage site. A donor polynucleotide can be single-stranded DNA, double-stranded DNA, RNA, or a duplex of RNA and DNA. A donor polynucleotide can be a sequence that does not naturally occur at a target nucleic acid cleavage site. In some embodiments, modifications of a target nucleic acid due to NHEJ and/or HDR can lead to, for example, mutations, deletions, alterations, integrations, gene correction, gene replacement, transgene insertion, nucleotide deletion, gene disruption, and/or gene mutation. The process of integrating non-native nucleic acid(s) into genomic DNA can be referred to as "genome engineering".

In an embodiment, the biotinylated molecule is a nanoparticle, such as a quantum dot, a gold particle, a magnetic particle, a polymeric nanoparticle. In another embodiment, the biotinylated molecule is a biotinylated fluorescent dye such as Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexa Fluor® 488 biocytin, Alexa Fluor®546, Alexa Fluor® 549, lucifer yellow cadaverine biotin-X, Lucifer yellow biocytin, Oregon green 488 biocytin, biotin-rhodamine and tetramethylrhodamine biocytin. Biotinylated molecule may also be a peptide, proteins or protein domains, specifically antibodies and Fab domains.

In another aspect, the biotin-binding molecule can be covalently linked to a donor polynucleotide, a nanoparticle, or a dye molecule either directly or via a linker molecule, using, for example a disulfide linker. The bound biotin-binding molecule can then bind the aptamer of the modified sgRNA. Additional biotinylated donor polynucleotides, nanoparticle, contrast agent, or dye molecules can then be associated with the bound biotin-binding molecule. Alternatively, the biotin-binding molecule can be associated with the biotinylated molecule prior to adding to modified sgRNA.

Further included herein are methods of modifying a target gene, such as a target gene in a cell by contacting the cell with the RNP complexes and modified guide RNAs described herein. The cell can be from any organism (e.g., a bacterial cell, an archaeal cell, a cell of a single-cell eukaryotic organism, a plant cell, an algal cell, a fungal cell (e.g., a yeast cell), a cell from an invertebrate animal, a cell from a vertebrate animal, or a cell from a mammal, including a cell from a human.

Also included herein is a method of modifying a target gene in a cell, comprising delivering to the cell the modified guide RNA, wherein the modified guide RNA is associated with a biotin-binding molecule, and wherein the single-stranded protospacer sequence of the modified guide RNA hybridizes to a sequence in the target gene to be modified.

In some embodiments, the present disclosure provides for methods of modifying a target gene in a plant. As used herein, the term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue).

In an embodiment, modifying the target gene increases or decreases the expression of a gene product of the target gene.

In another embodiment, modifying the target gene comprises high-fidelity homology-directed repair (HDR).

In another embodiment, modifying the target gene comprises the addition of a genetic functionality, or the correction of a mutation.

In yet another embodiment, modifying the target gene creates a double strand break (DSB) which is repaired by a non-homologous end joining (NHEJ) cell repair mechanism generating indels thereby modifying the polynucleotide sequence of the target gene.

In a further embodiment, modifying the target gene creates a DSB which is repaired by a homologous recombination (HDR) cell repair mechanism incorporating a donor DNA sequence thereby modifying the polynucleotide sequence of the target gene.

In an aspect, the S1m-sgRNAs described herein can be used for biallelic correction. Infantile-onset Pompe disease contains two distinct deleterious mutations at different points within a single gene. In an aspect, two S1m-sgRNAs can be employed simultaneously, one for correction of each disease locus. As shown in Example 11, clones containing edits at both alleles were identified.

In another aspect, the S1m-sgRNAs described herein can be used for the excision of genomic DNA. In an aspect, two S1m-sgRNAs can be employed simultaneously, wherein each S1m-sgRNA targets an end of the region to be excised. As shown in Example 12, human cells contain the properly excised region of genomic DNA Delivery of polynucleotides and RNPs of the present disclosure to cells, in vitro, or in vivo, may be achieved by a number of methods known to one of skill in the art. These methods include lipofection, electroporation, nucleofection, microinjection, biolistics, liposomes, immunoliposomes, polycation or lipid:nucleic acid conjugates. Lipofection is well known and lipofection reagents are sold commercially. Cationic and neutral lipids that are suitable for efficient receptor-recognition lipofection of polynucleotides are described in the art.

Lipid:nucleic acid complexes, including targeted liposomes such as immunolipid complexes, and the preparation of such complexes is well known to one of skill in the art.

Electroporation can be used to deliver the polynucleotides and RNPs of the present disclosure. In these methods, the polynucleotides or RNPs are mixed in an electroporation buffer with the target cells to form a suspension. This suspension is then subjected to an electrical pulse at an optimized voltage, which creates temporary pores in the phospholipid bilayer of the cell membrane, permitting charged molecules like DNA and proteins to be driven through the pores and into the cell. Reagents and equipment to perform electroporation are sold commercially.

Biolistic, or microprojectile delivery, can be used to deliver the polynucleotides and RNPs of the present disclosure. In these methods, microprojectiles, such as gold or tungsten, are coated with the polynucleotide by precipitation with calcium chloride, spermidine or polyethylene glycol. The microprojectile particles are accelerated at high speed into a cell using a device such as the BIOLISTIC® PDS-1000/He Particle Delivery System (Bio-Rad; Hercules, Calif.).

In another embodiment, a viral vector expressing the modified guide RNA of the present disclosure, a viral vector expressing a Cas9 polypeptide and biotinylated donor DNA template (e.g., a biotinylated donor DNA template), can be transfected into a cell, such as a human cell. Human cells include human pluripotent stem cell lines and primary blood cell such as hematopoietic stem and progenitor cells and T-cells. Once editing has occurred in the cell line, the cells can be differentiated and transplanted into a subject, or used for drug development.

In some embodiments, the polynucleotides of the present disclosure may also comprise modifications that, for example, increase stability of the polynucleotide. Such modifications may include phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and amino alkylphosphoramidates, phosphorodiamidates, thionophosphoramidates, thionoalkylphosphonates, thionoalkylphosphotriesters, selenophosphates, and boranophosphates having normal 3'-5' linkages, 2-5' linked analogs, and those having inverted polarity wherein one or more internucleotide linkages is a 3' to 3', a 5' to 5' or a 2' to 2' linkage. Exemplary nucleic acid-targeting polynucleotides having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

In some embodiments, the polynucleotides of the present disclosure may also contain other nucleic acids, or nucleic acid analogues. An example of a nucleic acid analogue is peptide nucleic acid (PNA).

The invention is further illustrated by the following non-limiting examples.

EXAMPLES

Methods

Cell Culture:

WA09 hESCs (WiCell, Madison, Wis.) were maintained in E8 medium on Matrigel® (WiCell) coated tissue culture polystyrene plate (BD Falcon). Cells were passaged every 3-4 days at a 1:6 ratio using Versene® solution (Life Technologies). WA09-BFP hESCs were generated through lentiviral transduction of BFP dest clone (Addgene #71825) and sorted to ensure clonal populations. After expansion, lines were sorted monthly on a BD FACS Aria to maintain expression levels.

Human embryonic kidney cells (293T) were obtained from ATCC and were maintained between passage 15-60 in Growth medium containing DMEM (Life Technologies), 10% v/v FBS (WiCell), 2 mM L-Glutamine (Life Technologies), and 50 U/mL Penicillin-Streptomycin (Life Technologies). Cells were passaged 1:40 with Trypsin-EDTA (Life Technologies) onto Gelatin-A (Sigma) coated plates. HEK-H2B-mCherry lines were generated through CRISPR-mediated insertion of a modified AAV-CAGGS-EGFP plasmid (Addgene #22212) at the AAVS safe harbor locus using gRNA AAVS1-T2 (Addgene #41818). HEK-BFP lines were generated and maintained as mentioned above. All cells were maintained at 37° C. and 5% $CO_2$.

One Pot Transcription of S1m-sgRNA:

S1m-sgRNAs were synthesized by first creating a double stranded DNA block that encoded the sgRNA scaffold as well as the S1m aptamer. This scaffold was formed by overlap PCR using Phusion® High-Fidelity Polymerase (New England Biolabs) according to the manufacturer's protocols and was placed in the thermocycler for 30 cycles of 98° C. for 10 s and 72° C. for 15 s with a final extension period of 72° C. for 10 min. A second primer consisting of a truncated T7 promoter, the sgRNA target, and homology to the S1m scaffold was then added to the scaffold and PCR was performed again using Phusion® and placed in a thermocycler at 98° C. for 30 s followed by 35 cycles of 98° C. for 5 s, 60° C. for 10 s, and 72° C. for 15 s, with a final extension period of 72° C. for 10 min. S1m PCR products were then incubated overnight at 37° C. in a HiScribe™ T7 IVT reaction (New England Biolabs) according to manufacturer's protocol. The resulting RNA was purified using MEGAclear™ Transcription Clean-Up Kit (Thermo Fisher) and quantified on a Nanodrop™2000.

S1m RNP Formation:

NLS-Cas9-NLS protein (Aldevron, Madison, Wis.) was combined with S1m-sgRNAs and allowed to complex for 5 minutes with gentle mixing. To this complex, streptavidin (Life Technologies) was added and the mixture was allowed to complex for an additional 5 minutes. Finally, biotin-ssODNs (Integrated DNA Technologies) were added to the tertiary complex and subsequently vortexed at low speed. This final mixture was then allowed to sit for 10 minutes to ensure complete complexation.

S1m-sgRNA and Streptavidin Binding Gel Shift Assays:

S1m-sgRNAs were heated at 75° C. for 5 min and cooled to room temperature for 15 min. 20 pmol S1m-sgRNA was combined with streptavidin at 10:1, 1:1, and 1:10 molar ratios in a final volume of 5 µl and the mixture was allowed to complex for 10 min. The S1m-sgRNA-streptavidin complexes were run on a 1% agarose gel. Tertiary complexes were assembled by first mixing 15 pmol each of S1m-sgRNA and streptavidin. To this mixture, 6, 15, or 30 pmol of ssODN was added prior to running the complexes through a 1% agarose gel. All gels were run using Kb+ Ladder (Invitrogen) as a molecular weight marker to allow for inter-gel size comparisons even when running RNA samples.

Biotin Competition Assay:

S1m-sgRNA was heated to 75° C. for 5 min and cooled to room temperature. 20 pmol each S1m-sgRNA and streptavidin were complexed for 10 min. 80 pmol biotin was added at 30, 20, 10, 5, and 0 min intervals prior to running the complexes through a 1% agarose gel.

Dynamic Light Scattering:

DLS was performed using a DynaPro® NanoStar® (Wyatt Technology) using small volume (4 µL) disposable cuvettes. 10 µg of each component was added into the cuvette and diluted as necessary with $dH_2O$ to reach 4 µL solution volume. In mixed component conditions, components were allowed to mix for 5 minutes while taking readings. Acquisitions were performed for 20 seconds with a minimum of 4 acquisitions per measurement. 5 measurements were performed per sample and were conducted at room temperature. Data was graphed as a function of percent intensity.

Quantum Dot Biotin Conjugation:

To make Qdot-SS-s1mplexes, amine-PEG green fluorescent quantum dots (Qdot® ITK™ 525—ThermoFisher) were reacted with a degradable dithiol biotin linker (EZ-Link™® Sulfo-NHS-Biotin—ThermoFisher) as follows: First, 25 µl of an 8 µM Quantum dot solution in 50 mM Borate buffer were desalted into PBS using Zeba desalting columns (40K MWCO—ThermoFisher) and then reacted with excess sulfoNHS-dithiol-biotin linker for 2 hours at 4° C. with shaking. The conjugate was purified from excess linker through buffer exchange in the desalting columns. Quantum dots retained their fluorescence and were stored at 4° C. until use.

RNP Delivery:

HEK transfections were performed using TransIT-X2® delivery system (Mirus Bio, Madison, Wis.) according to manufacturer's protocol. $2.5 \times 10^5$ cells/$cm^2$ were seeded in a 24-well plate 24 hours prior to transfection. RNP complexes were formed as described in 25 uL of Opti-MEM™ (Life Technologies). 1 µg of Ca9 protein, 500 ng sgRNA, 500 ng streptavidin, and 500 ng ssODN were used. In a separate tube, 25 uL of Opti-MEM™ was combined with 0.75 uL of TransIT-X2® reagent and allowed to mix for 5 minutes. TransIT-X2® and RNP solutions were then mixed by gentle pipetting and placed aside for 15 minutes. After this incubation, 50 µL of solution were added dropwise into the well. Media was changed 24 hours post transfection.

For HEK transfections involving quantum dots, Lipofectamine™ 2000 (Life Technologies) was used for delivery. Qdot-RNP complexes were formed according to the following amounts (for 24 wells: 500 ng of Ca9 protein, 187.5 ng sgRNA, 187.5 ng streptavidin, 3.125 pMoles of quantum dots and 3 ul Lipofectamine™ per well; a quarter of these amounts were used when transfecting 5000 cells in 96 well plates).

All hPSC transfections were performed using the 4D-Nucleofector™ System (Lonza) in P3 solution using protocol CB150. Cells were pretreated with Rho-kinase (ROCK) inhibitor (Y-27632 Selleck Chemicals) 24 hours prior to transfection. 8 µg Cas9, 3.5 µg sgRNA, 3.5 µg streptavidin, and 1 µg ssODN were used to form particles as described above. Cells were then harvested using TrypLE™ (Life Technologies) and counted. $2 \times 10^5$ cells per transfection were then centrifuged at 100×g for 3 minutes. Excess media was aspirated and cells were resuspended using 20 µL of RNP solution per condition. After nucleofection, samples were incubated in nucleocuvettes at room temperature for 15 minutes prior to plating into one well of a 6-well plate containing E8 media+10 µM ROCK inhibitor. Media was changed 24 hours post transfection and replaced with E8 medium.

Immunocytochemistry:

To measure correlation hPSCs were transfected with Cas9 protein and streptavidin-AF-647. 24 hours post transfection, cells were fixed using 4% PFA and incubated at room temperature for 10 minutes. Cells were then permeabilized using 0.05% Triton X-100 and incubated for 10 minutes. Following two washes with 5% goat serum, Cas9 antibody (Clontech #632607, 1:150) was added to cells and incubated overnight at 4° C. The next day, cells were rinsed twice with 5% goat serum and then incubated with a goat anti-rabbit secondary antibody (Santa Cruz Biotech #sc-362262, 1:500) for one hour at room temperature. Cells were then washed twice with PBS and mounted for imaging.

To visualize S1mplexes in the nucleus human embryonic kidney cells (HEK293T) were plated at 16,000 cells per well in an 8-well chamber slide at day 0. On day 1, 20 mL of transfection media was added to cells in 200 µL of maintenance media. Transfection media contained 20 µL Opti-MEM® (Life Technologies), 10 pmol Streptavidin Alexa Fluor® 488 conjugate (Thermo Fisher), and 0.6 µL TransIT® transfection reagent (Mirus). On day 3, cells were incubated with 1× CellMask™ Plasma Membrane Stain (ThermoFisher) and 1× Hoechst for 10 min. Following incubation at 37° C., cells were immediately washed with PBS and fixed in 4% paraformaldehyde (IBI Scientific) at room temperature for 15 min. Cells were analyzed using a Nikon Eclipse TI epifluorescent microscope and a Nikon AR1 confocal microscope.

Multispectral Imaging Flow Cytometry:

hPSCs were transfected and stained as described above. After staining, cells were centrifuged and resuspended in 50 µL PBS. Fluorescence was detected on ImageStream® X Mark II (EMD Millipore) according to manufacture instructions. Cellular colocalization was measured by IDEAS software package (Amnis) using predefined colocalization wizard.

Flow Cytometry:

Flow cytometry of BFP expression and conversion to GFP was measured using a BD FACS Aria using the DAPI and FITC filters and analyzed using FlowJo. Voltages were established by running wild type WA09 hPSCs as well as WA09-BFP hPSCs. Sorting was performed on a BD FACSAria™ II with a nozzle size of 100 μm at room temperature and sorted into culture media.

Genomic Analysis:

DNA was isolated from cells using DNA QuickExtract™ (Epicentre, Madison, Wis.) following treatment by 0.05% trypsin-EDTA and centrifugation. QuickExtract™ solution was incubated at 65° C. for 15 minutes, 68° C. for 15 minutes, and finally 98° C. for 10 minutes. Genomic PCR was performed following manufacturer's instructions using AccuPrime™ HiFi Taq (Life Technologies) and 500 ng of genomic DNA. Products were then purified using AMPure® XP magnetic bead purification kit (Beckman Coulter) and quantified using a Nanodrop™2000. For deep sequencing, samples were pooled and run on an Illumina HiSeq™ 2500 High Throughput at a run length of 2×125 bp or an Illumina Miseq® 2×150 bp.

Deep Sequencing Data Analysis:

A custom python script was developed to perform sequence analysis. The pipeline starts with preprocessing, which consists of filtering out low quality sequences and finding the defined ends of the reads. For each sample, sequences with frequency of less than 100 were filtered from the data. Sequences in which the reads matched with primer and reverse complement subsequences classified as "target sequences". Target sequences were aligned with corresponding wildtype sequence using global pairwise sequence alignment. Sequences that were misaligned around the expected cut site were classified as NHEJ events while sequences that had insertions larger that 15 bp were classified as HDR events. The frequency, length, and position of matches, insertions, deletions, and mismatches were all tracked in the resulting aligned sequences.

Cell Membrane Staining:

Human embryonic kidney cells (HEK293) were plated at 16,000 cells/well in an 8-well chamber slide at day 0. On day 1, 20 pt of transfection media was added to cells in 200 μL of maintenance media. Transfection media contained 20 μL Opti-MEM® (Life Technologies), 400 ng Streptavidin Alexa Fluor® 488 conjugate (Thermo Fisher), and 0.6 μL TransIT® transfection reagent (Mirus). On day 3, cells were incubated with 1× CellMask™ Plasma Membrane Stain (ThermoFisher) and 1× Hoechst for 10 min. Following incubation at 37 C, cells were immediately washed with PBS and fixed in 4% paraformaldehyde (IBI Scientific) at room temperature for 15 min. Cells were analyzed using a Nikon Eclipse TI epifluorescent microscope and a Nikon AR1 confocal microscope.

Statistics:

All error bars are shown as ±1 standard deviation. p values were computed using a Student's two-tailed t-test and deemed significant at α<0.05.

Nucleic Acid Sequences:

The relevant nucleic acid sequences are provided in the following tables:

TABLE 1

Primers used to create sgRNA and S1m-sgRNAs.

| S1m Construct Name | Sequence (5' to 3') | SEQ ID NO: |
|---|---|---|
| S1m-sgRNA-1_F | GTTTAAGAGCTATGCTGCGAATACGAGATGCGGC CGCCGACCAGAATCATGCAAGTGCGTAAGATAGT CGCGGGTCGGCGGCCGCATCTCGTATTC | 8 |
| S1m-sgRNA-1_R | AAAAGCACCGACTCGGTGCCACTTTTTCAAGTTGA TAACGGACTAGCCTTATTTAAACTTGCTATGCTGC GAATACGAGATGCGGCCGCCGACCCG | 9 |
| S1m Forward | TTAATACGACTCACTATAGGNNNNNNNNNNNNNNN NNNNNNGTTTAAGAGCTATGCTGCGA | 10 |
| RNATracR | AAAAGCACCGACTCGGTGCC | 11 |

TABLE 2

Protospacer and respective PAMs used for genomic targeting.

| sgRNA Name | Sequence (5' to 3') | PAM | SEQ ID NO: |
|---|---|---|---|
| BFP (BFP→GFP) | GCTGAAGCACTGCACGCCAT | GGG | 12 |
| EMX1 (EMX1_21) | GTCACCTCCAATGACTAGGG | TGG | 13 |
| mCherry (mCherry_15) | GGAGCCGTACATGAACTGAG | GGG | 14 |

TABLE 3

Forward and reverse primers for genomic loci.

| Genomic Primer | Forward (5' to 3') | SEQ ID NO: | Reverse (5' to 3') | SEQ ID NO: |
|---|---|---|---|---|
| EMX1 | CCATCCCCTT CTGTGAATGT | 15 | GGAGATTGGAG ACACGGAGA | 16 |
| EMX1 Symmetric | TCCACCTTGG CTTGGCTTTG | 17 | CCCTCCACCAG CTACCCAC | 18 |
| mCherry Interior | AAGGGCGAGG AGGATAACATGG | 19 | TTGTACAGCTC GTCCATGCCG | 20 |
| EMX1 Insertion | CCAATGACAA GCTTGCTAGC | 21 | | |

TABLE 4 ssODNs used to direct HDR after DSB formation.

| ssODN Donor | Sequence (5' to 3') | SEQ ID NO: |
|---|---|---|
| BFP→GFP NT | TCATGTGGTCGGGGTAGCGGCTGAAGCACTGCA CGCCATGGGTCAGGGTGGTCACGAGGGTGGGC CAGGGCACCGGCAGCTTGCCGGTGGTGCAGAT GAA | 22 |

TABLE 4-continued ssODNs used to direct HDR after DSB formation.

| ssODN Donor | Sequence (5' to 3') | SEQ ID NO: |
|---|---|---|
| BFP→GFP 5PCBi NT | 5Biotin/TCATGTGGTCGGGGTAGCGGCTGAAG CACTGCACGCCATGGGTCAGGGTGGTCACGAGGGT GGGCCAGGGCACCGGCAGCTTGCCGGTGGTGC AGATGAA | 23 |
| EMX1 NT | AAGCAGCACTCTGCCCTCGTGGGTTTGTGGTTG CCCACCGCTAGCAAGCTTGTCATTGGAGGTGAC ATCGATGTCCTCCCCATTGGCCTG | 24 |
| EMX1 5PCBio NT | 5Biotin/AAGCAGCACTCTGCCCTCGTGGGTTT GTGGTTGCCCACCGCTAGCAAGCTTGTCATTGGAG GTGACATCGATGTCCTCCCCATTGGCCTG | 25 |

TABLE 5

Off-target sequences and corresponding genomic locus for each sgRNA used. Mismatches from protospacer are labelled in red.

| sgRNA Target Sequence | | Off-Target Sequence | SEQ ID NO: | PAMLocus |
|---|---|---|---|---|
| BFP→ GFP GCTGAAGCACT GCACGCCAT (SEQ ID NO: 26) | OT1 | GCAGAAGCACTG CAAGCCAT | 27 | CAGchr17: +39786906 |
| | OT2 | TCTGAAGTGCTG CACGCCAT | 28 | CAGchr2: -238397265 |
| | OT3 | GTGGAAGCACTG CAAGCCAT | 29 | TGGchr7: -11228464 |
| | OT4 | GCTGGAGCAGGG CACGCCAT | 30 | CAGchr9: +109114765 |
| | OT5 | GAAGAAGCACTG CACCCCAT | 31 | CAGchr13: -75660548 |
| EMX1 GTCACCTCCAA TGACTAGGG (SEQ ID NO: 32) | OT1 | AGGACCACCAAT GACTAGGG | 33 | CAGchr3: -64303990 |
| | OT2 | ACCACCTGTAAT GACTAGGG | 34 | TAGchr4: -149749778 |
| | OT3 | GGAGCCTCCAGT GACTAGGG | 35 | GAGchr17: -38423030 |
| | OT4 | GTGAACTACAGT GACTAGGG | 36 | TGGchr8: +112210096 |
| | OT5 | CTGGCCTCCAAA GACTAGGG | 37 | GAGchr15: -75011931 |

TABLE 6

Forward and reverse primers used to amplify off-target genomic loci.

| Off-Target Primer | Forward (5' to 3') | SEQ ID NO: | Reverse (5' to 3') | SEQ ID NO: |
|---|---|---|---|---|
| BFP OT1 | TTTCCTAGCAAGC AGACTCAGA | 38 | AGCTGTCCTTTGTCC CATTGA | 39 |
| BFP OT2 | TCTCCATGCCCTCC TTTCCAT | 40 | GGATGTAGTCCATGA TCTTCCCC | 41 |
| BFP OT3 | TCCCAGAATGTGA AAGTGGAGG | 42 | CTGTGGGCTTTCCTC AGCTC | 43 |
| BFP OT4 | GCTGACTAACGTC CACTGCT | 44 | TGGACCTATGTTTTT CTTCGTCAC | 45 |
| BFP OT5 | AAAGTCTGTGGCC TTGTGAGA | 46 | AACCCTACCCCCTAC CTGAA | 47 |
| EMX1 OT1 | TTCCCCAGGTAGT TGCTGTTC | 48 | TCTGCACATGTCCCA ACTGTC | 49 |
| EMX1 OT2 | ATCCGTACCTAAC ATGACCC | 50 | GCACAGATCTTGGTG GCTTT | 51 |
| EMX1 OT3 | GGCTGGGTTTCCC AAACGTA | 52 | CAAACTGCTGTGTTG GGTGG | 53 |
| EMX1 OT4 | ACTTGGAAGGGTC CACACAA | 54 | CCTTGAATAGAGCAT TTTTCCCCA | 55 |
| EMX1 OT5 | TCCTACCCTTGGA TGGGGTT | 56 | GGGCTACACGGTCCC TAAAG | 57 |

Example 1: Design of Modified sgRNA

Figure 3:
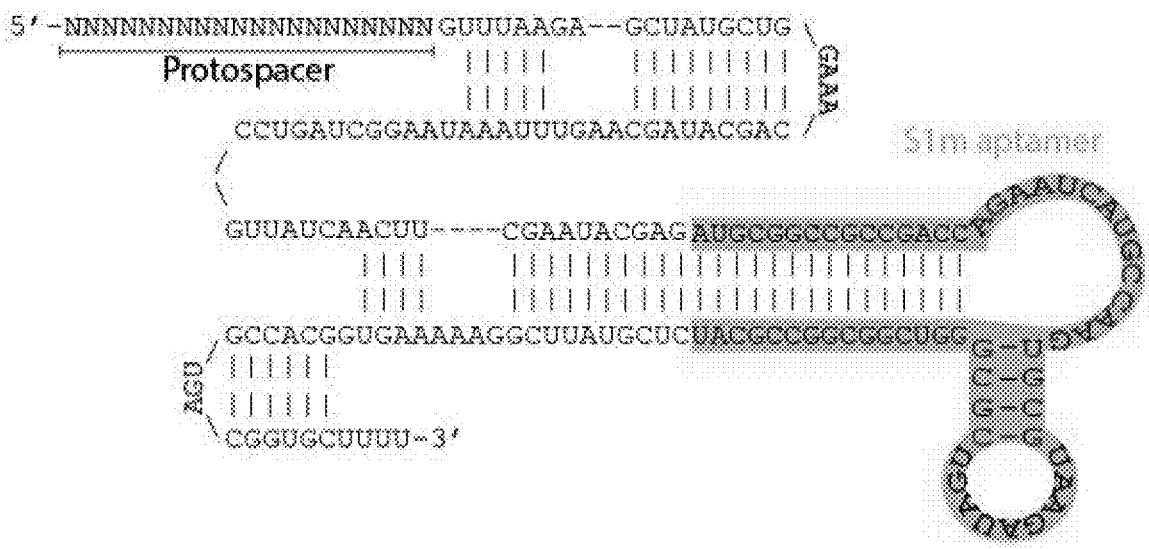
FIG. 3 shows the predicted secondary structure of S1m-sgRNAs variants.
Figure 3:
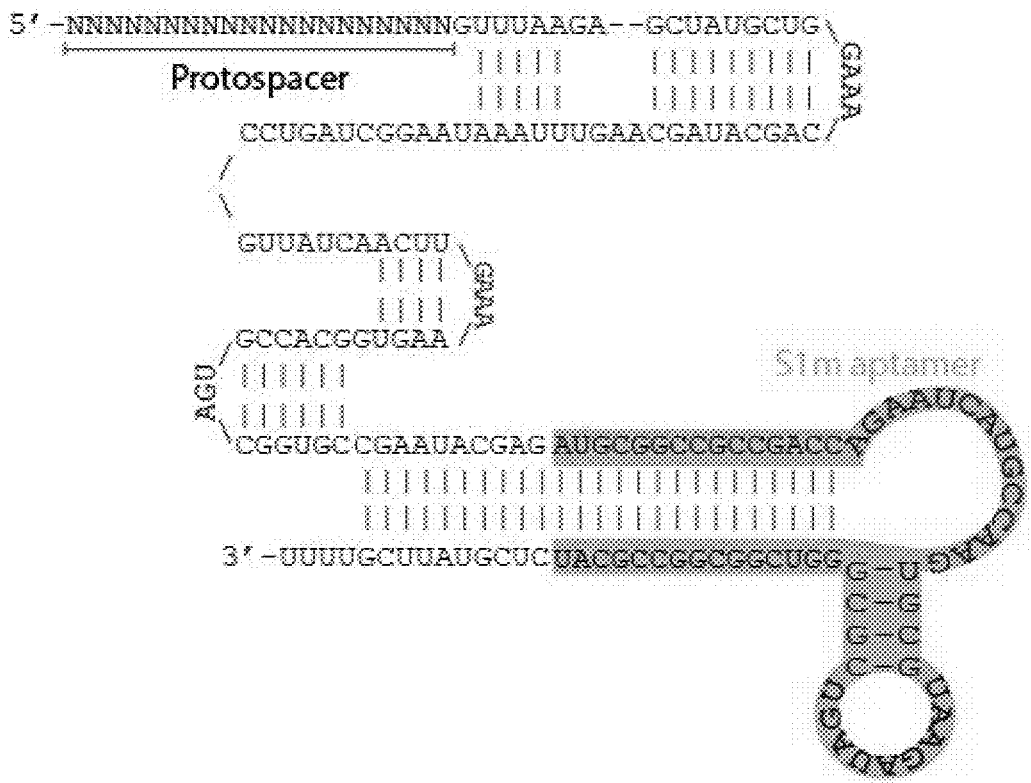
Figure 4:
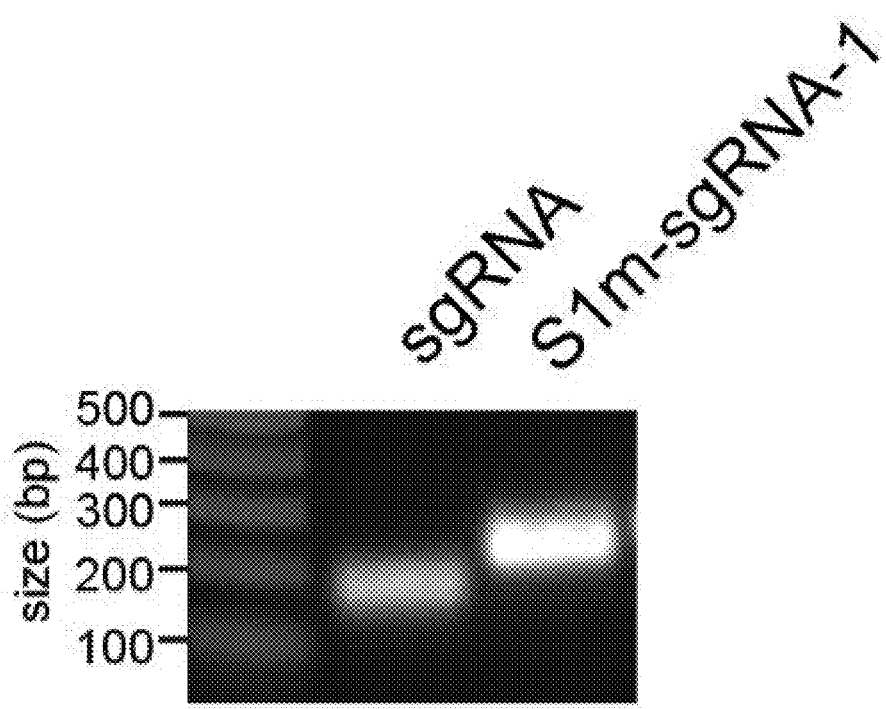
FIG. 4 shows in vitro transcription of S1m-sgRNAs compared to standard sgRNAs. S1m-sgRNAs are larger than sgRNAs due to the insertion of S1m stem loop.

A novel sgRNA with a modification at the stem loop closest to the 5' end of the sgRNA was designed (FIG. 3). This location was chosen because it has previously been shown to tolerate additions with a minimal loss in activity. An S1m aptamer was added, which has a strong non-covalent interaction with streptavidin. The added S1m aptamer extends the sgRNA stem loop closest to the 5' end and contains two distinct bulges used for binding. These modifications do not otherwise disrupt the predicted sgRNA secondary structure (FIG. 3). We confirmed that S1m-sgRNAs can be made rapidly in vitro via one-pot transcription and are larger than standard sgRNAs when analyzed by agarose gel electrophoresis (FIG. 3).

Similar experiments were performed with sgRNAs S1m-sgRNA-1, S1m-sgRNA-2, S1m-sgRNA-3, and S1m-sgRNA-V3.

Example 2: Formation of Streptavidin and Cas9 Complexes with Modified sgRNA

Figure 5:
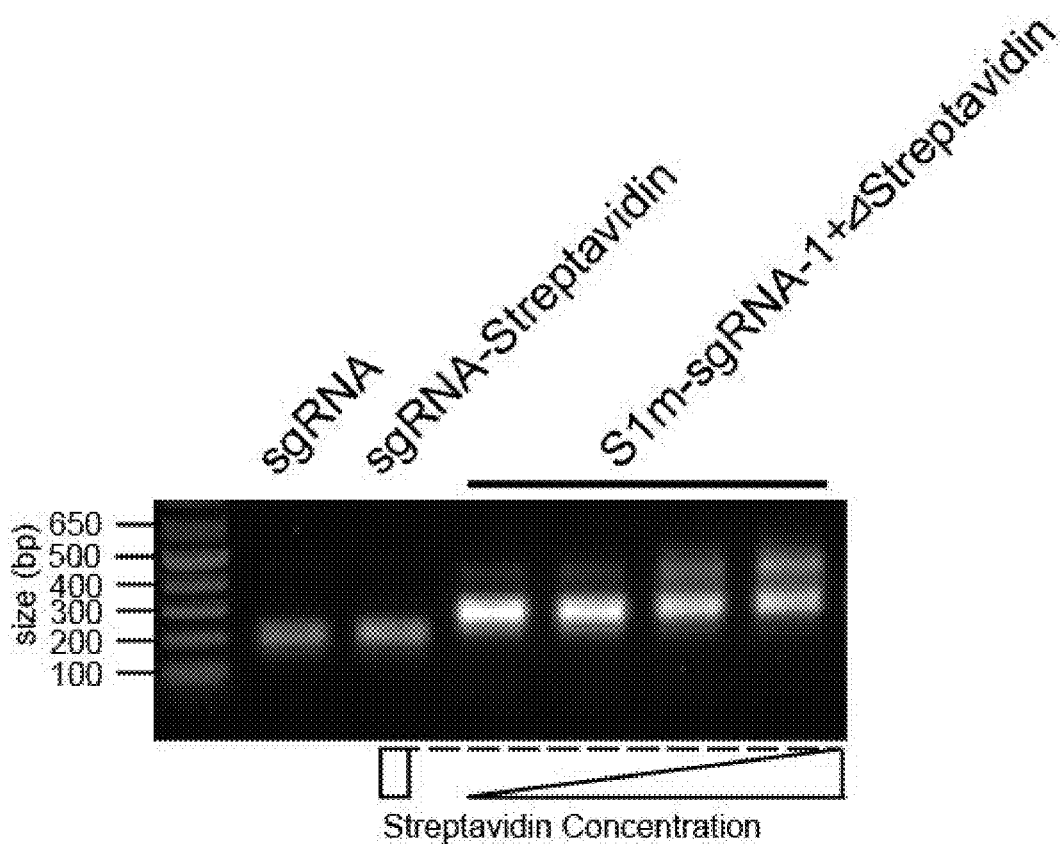
FIG. 5 shows in vitro complexes of sgRNAs and streptavidin. Lane 1: S1m-sgRNA. Lane 2: streptavidin. Lane 3-5: Progressive ratios of S1m-sgRNA streptavidin. As streptavidin concentration was increased the electrophoretic front of S1m-sgRNAs was slowed. The presence of several bands may be due to multiple S1m-sgRNAs binding to a single streptavidin. Lane 6-7: Addition of streptavidin to standard sgRNAs do not shift the electrophoretic front.

Next, we verified the ability of S1m-sgRNAs to complex with streptavidin in vitro by combining a constant amount of S1m-sgRNA with increasing amounts of streptavidin. The electrophoretic front of the S1m-sgRNA slowed as streptavidin levels increased (FIG. 5). At the maximum amount of streptavidin, 40% of the front had slowed demonstrating the binding of the S1m-sgRNA with streptavidin. In contrast, when the same amount of standard (non-S1m) sgRNA was run with streptavidin, the electrophoretic front remained constant.

Figure 6:
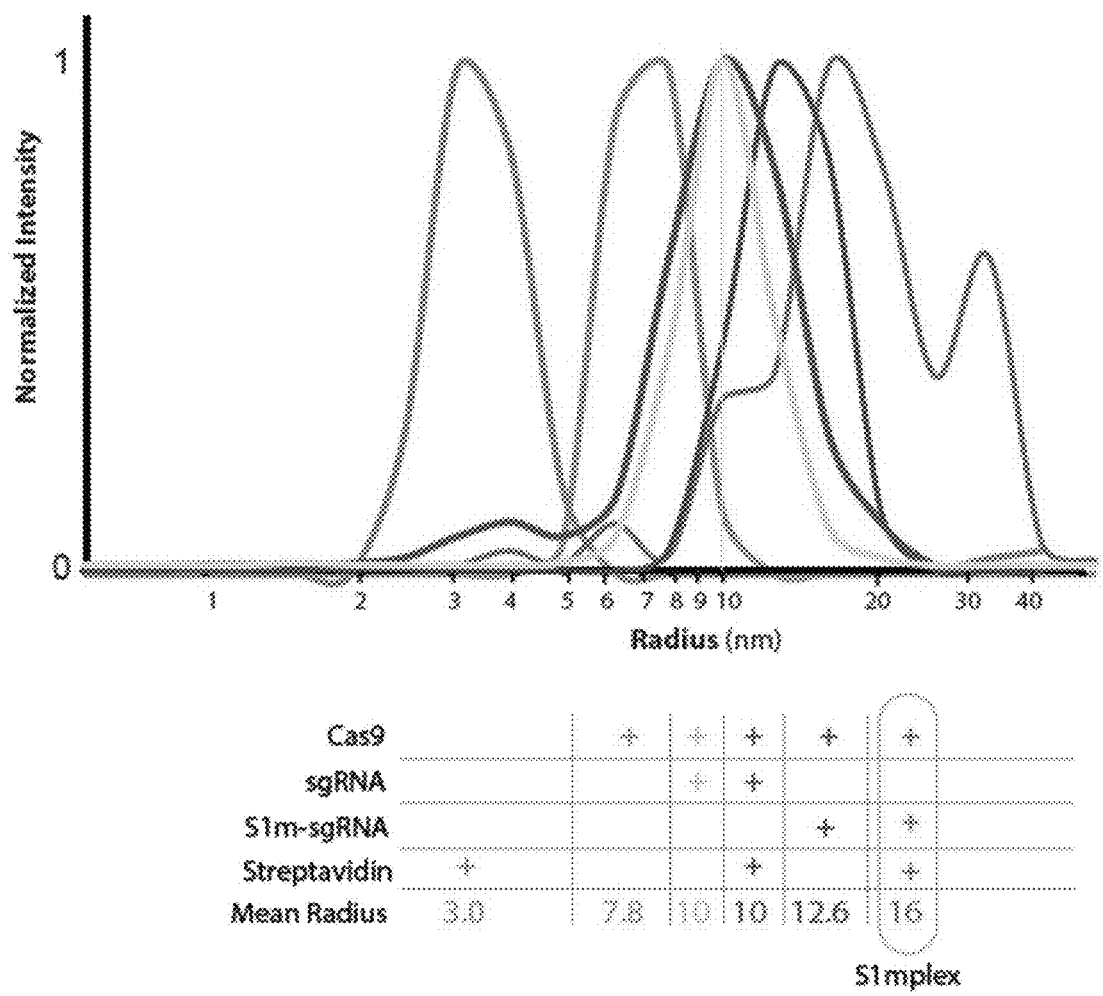
FIG. 6 shows dynamic light scattering of ssODN-S1mplex (S1mplex=tertiary complexes of Sp.Cas9, S1m-sgRNA, and streptavidin) particle assembly. Cas9 (orange) and streptavidin (blue) proteins fail to interact when in solution together and have a hydrodynamic radius consistent with published data. The addition of sgRNA to Sp.Cas9 protein increases the radius of the particle to 10 nm (yellow). This radius does not change with the addition of streptavidin (red). When S1m-sgRNAs are added to Sp.Cas9 (purple), the radius is increased by a larger amount than sgRNAs, potentially due to the larger size of the S1m-sgRNA. When streptavidin is added to this complex (green), a shift in size of about 3 nm occurs, the size of streptavidin. A second peak at 35 nm may be associated with multiple Cas9-S1m-sgRNA complexes connected to a single streptavidin.

To demonstrate the ability of S1m-sgRNA-1 to complex with streptavidin and Cas9 protein simultaneously, we performed dynamic light scattering (DLS). When streptavidin and Cas9 were combined in solution, two peaks were distinct at 3.0 nm and 7.8 nm (FIG. 6), both of which match closely the radii previously reported for each protein. We next formed Cas9 RNPs with excess standard sgRNAs and observed that the species formed were larger than Cas9 alone and did not increase in radius with the addition of streptavidin. Excess sgRNA was not detected by DLS and was included in the DLS studies to ensure all key components were able to assemble together (data not shown). Additionally, these samples had a discernable peak corresponding to the presence of streptavidin alone. RNPs containing S1m-sgRNAs and Sp.Cas9 protein increased in radius by a larger amount than RNPs containing standard sgRNAs and Sp.Cas9 protein, likely due to the increased length of S1m-sgRNAs. When streptavidin was added to S1m-sgRNA RNPs, the average radius of the complex was increased by ~3 nm, the radius of streptavidin protein. These tertiary complexes of Sp.Cas9, S1m-sgRNA-1, and streptavidin are termed "S1mplexes". The second, larger peak in the S1mplex DLS trace is attributed to the tetrameric nature of streptavidin that can harbor up to four RNPs.

Figure 7:
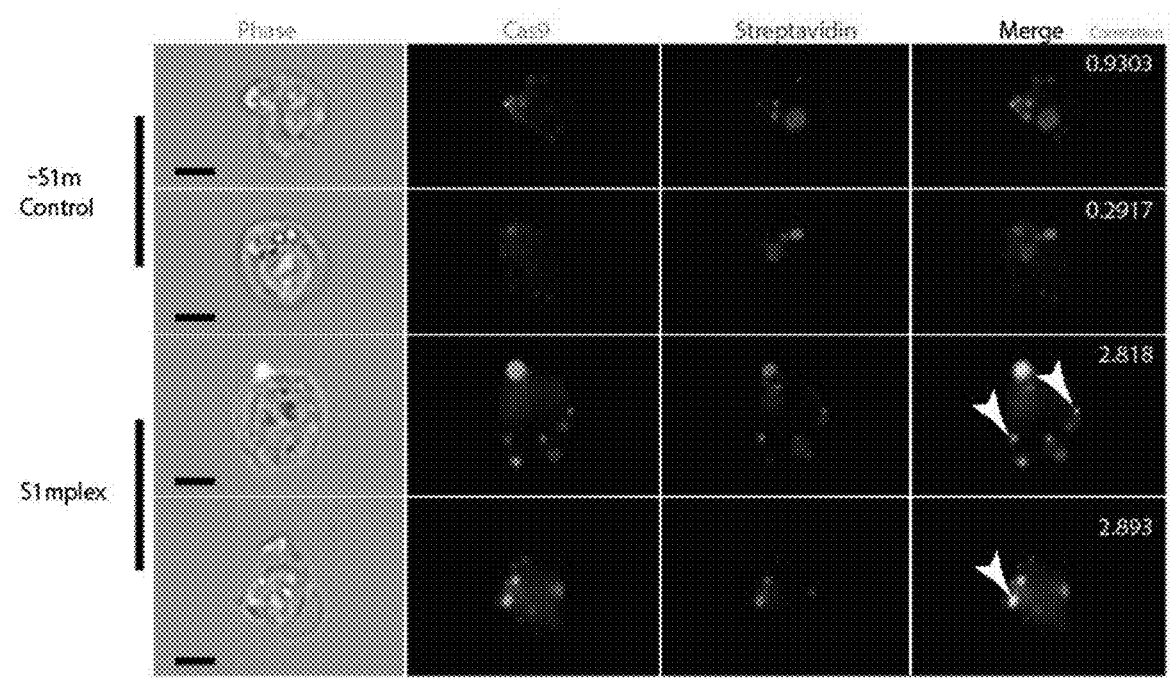
FIG. 7 shows two representative single cell multispectral flow cytometric images of S1m-sgRNA and sgRNA transfected cells with Cas9 immunohistochemistry and fluorescent streptavidin (scale bar: 10 μm). Arrowheads indicate presence of overlapping colors. Numbers in yellow are measured log Pearson correlation coefficient as determined by IDEAS software.
Figure 8:
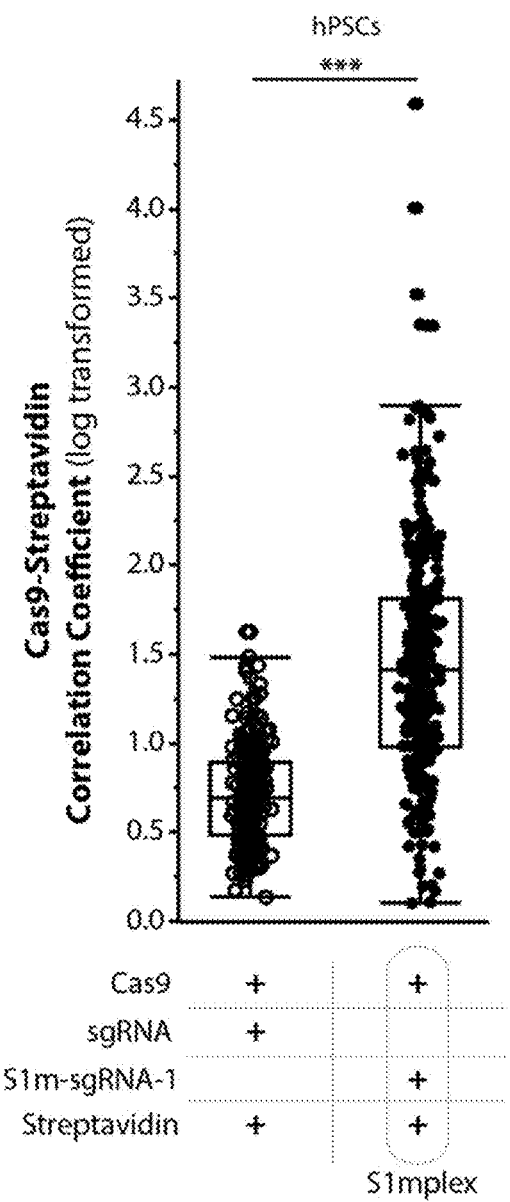
FIG. 8 shows the correlation coefficient of Cas9 immunocytochemistry fluorescent signal and streptavidin fluorescence, as measured by multispectral image cytometry within hPSCs. Use of S1m-sgRNA significantly increased the correlation between the two signals (***$p<10^{-5}$, Student's two-tailed t-test).
Figure 9:
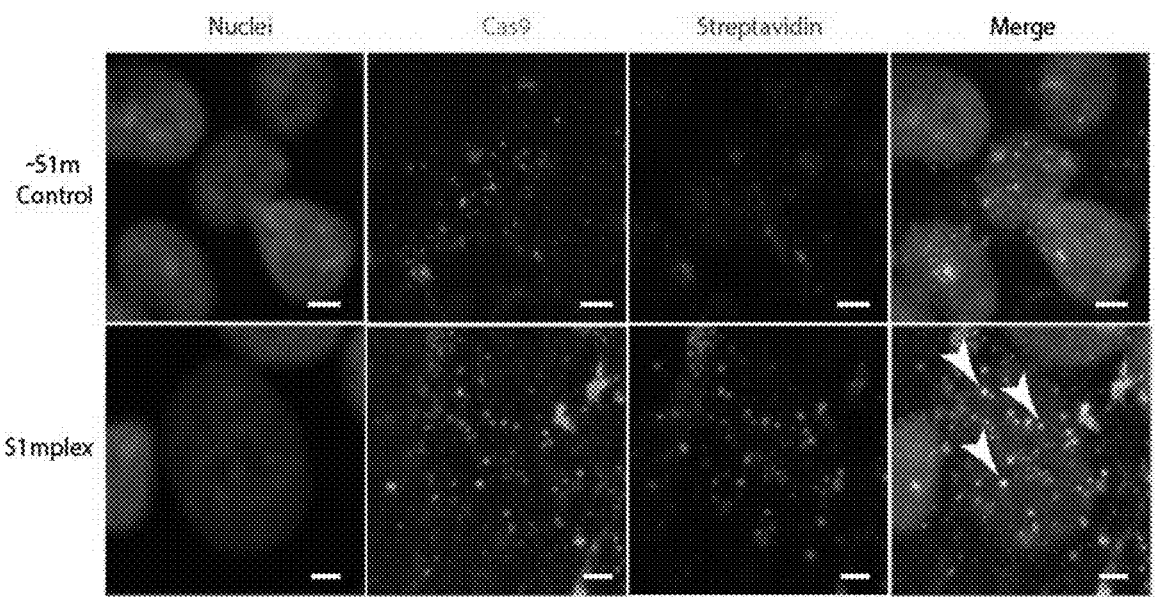
FIG. 9 shows representative confocal images of S1m-sgRNA and sgRNA transfected cells with Cas9 immunohistochemistry and fluorescent streptavidin (scale bar: 5 μm). Arrowheads indicate presence of overlapping colors.
Figure 10:
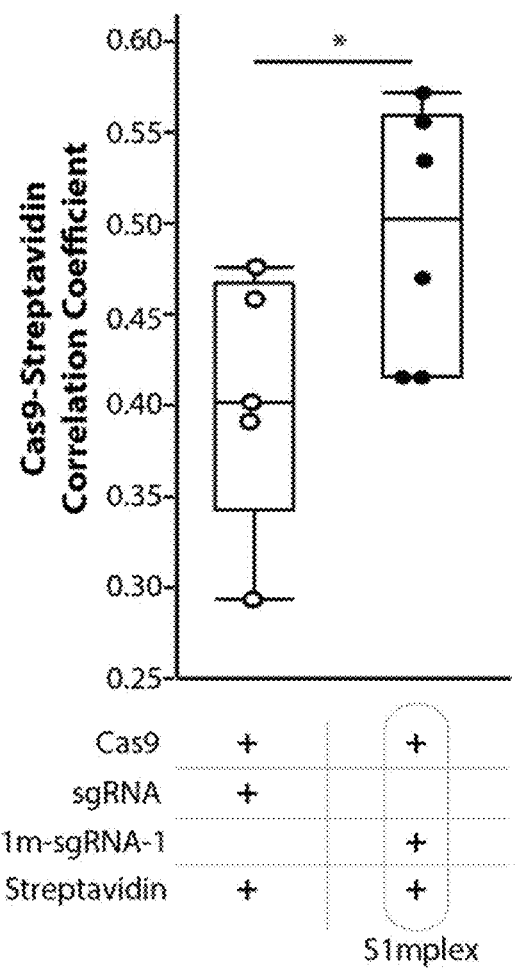
FIG. 10 shows the correlation coefficient of Cas9 immunocytochemistry and streptavidin fluorescence inside the nuclei of transfected cells. Introduction of S1m-sgRNAs significantly increased the correlation between the two molecules (*p<0.05, Student's two-tailed t-test).

While assembly of S1mplexes in vitro is important, the maintenance of complexes post-delivery is imperative to gene editing function. To demonstrate this capability, we delivered Cas9 protein and streptavidin in combination with either sgRNAs or S1m-sgRNAs into human pluripotent stem cells (hPSCs) via nucleofection and conducted immunohistochemistry for the two protein components. Multispectral imaging flow cytometric analysis of single fixed cells confirmed the co-localization of the two protein components within hPSCs (FIG. 7). Significantly higher correlation in the fluorescent signals from the two protein components were seen when S1m-sgRNA-1 was included ($p<10^{-5}$, Student's two-tailed t-test FIG. 8). To gain further subcellular resolution of these components after S1mplex delivery, images obtained using confocal microscopy on fixed, intact hPSC cultures were analyzed using CellProfiler for overlap between the two components within the nuclei. At 24 hours after delivery, the correlation between the fluorescent signals arising from Cas9 and streptavidin within the nucleus was significantly higher when using S1m-sgRNAs than sgRNAs ($p<0.05$, Student's two-tailed t-test, FIG. 9, 10). Together, these results indicate that complexes between Cas9 and streptavidin are preserved specifically through the S1m aptamer during transfection and subsequent subcellular trafficking such as nuclear transport.

Example 3: Formation of a Quaternary Complex with Donor DNA Template

Figure 11:
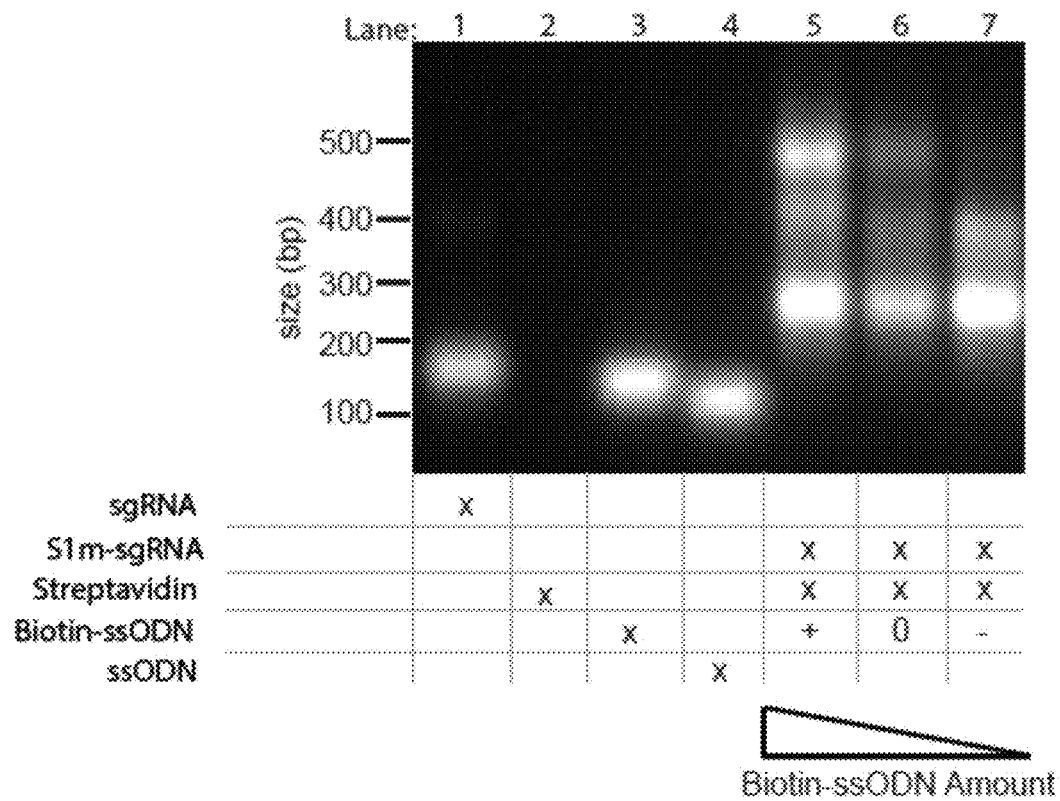
FIG. 11 shows in vitro tertiary complexes of S1m-sgRNA, streptavidin, and ssODN. Lanes 1-4: Components of S1m particles ran individually. Lanes 5-7: complexes of S1m-sgRNAs, streptavidin, and biotin-ssODNs. Three concentrations of ssODN were used while amount of S1m-sgRNA and streptavidin was held constant. Major bands showing the complexation of all three components can be seen. Elongated bands may be due to different stoichiometry of bio-ssODN and S1m-sgRNA connected to streptavidin.
Figure 12:
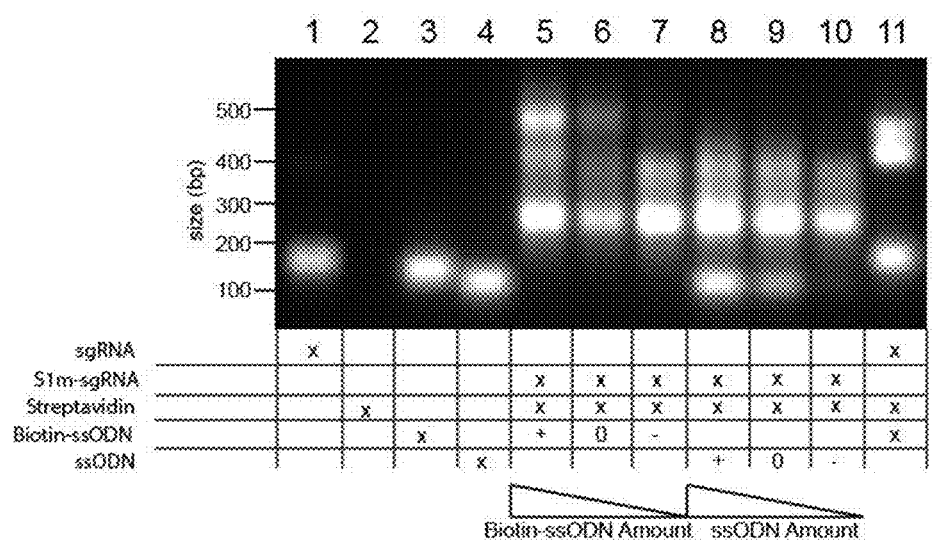
FIG. 12 shows in vitro tertiary complexes of S1m-sgRNA, streptavidin, and ssODN. Lanes 1-4: Components of S1m particles ran individually. Lanes 5-7: complexes of S1m-sgRNAs, streptavidin, and biotinylated ssODNs. Numbers represent relative stoichiometry between components ran on gel. Major bands showing the complexation of all three components can be seen. Elongated bands may be due to different stoichiometry of biotin-ssODN and S1m-sgRNA connected to streptavidin. Lanes 8-10: complexes of S1m-sgRNAs, streptavidin, and ssODNs. ssODNs do not interfere with the binary complex. Lane 11: complexes of streptavidin and biotin-ssODNs, with free sgRNAs. None of the typical S1m-sgRNA-streptavidin complexes can be seen in this lane.

After demonstrating the ability to form S1mplexes, we searched for a method to combine donor DNA template with S1mplexes and form a quaternary complex. Given the strong interaction between streptavidin and biotin ($K_D=10^{-15}M$) we selected biotinylated single-stranded oligodeoxynucleotide (ssODNs) donor templates. All components (S1m-sgRNA, streptavidin, biotin-ssODN) were run alone individually on a gel and compared side-by-side with standard reagents (sgRNA, ssODN) to establish baseline migration characteristics. The biotin-ssODN ran slightly higher than the standard ssODN, presumably due to the biotin modification (FIG. 11, 12). Tertiary complexes were formed using varying levels of biotin-ssODNs. The primary band displayed a higher electrophoretic shift than either the sgRNA or ssODN alone, indicating complex formation (FIG. 11, lanes 5-7). To demonstrate that all components combined successfully, unmodified ssODNs were run in the place of biotin-ssODNs. The unmodified ssODN displayed the expected electrophoretic shift despite the presence of the S1m-streptavidin complex (FIG. 12, lanes 8-10). Finally, standard sgRNA was run with streptavidin and biotin-ssODN. In this condition, the smeared band from S1m-streptavidin binding was not observed and instead solid bands representing sgRNA and ssODN-streptavidin were present (FIG. 12, lane 11).

Due to the strong interaction of biotin and streptavidin, we needed to ensure that biotin did not displace S1m-sgRNA-1 already bound to streptavidin when added in solution. To do so, we combined S1m-sgRNA-1s with streptavidin at a 1:1 molar ratio. We then added 4-fold molar excess of biotin to occupy every binding site on each streptavidin molecule and incubated the complex for 0, 5, 10, 20, or 30 minutes. After incubation, gel shift following electrophoresis was not different from bound S1m-sgRNA: streptavidin combinations suggesting that biotin did not interfere with the S1m-streptavidin interaction at four times the concentrations used in this study (data not shown).

Example 4: Gene Editing Activity of S1m-sgRNAs in Human Cells

Next, we examined the ability of S1m-sgRNAs to edit genes within human cells. We created a human embryonic kidney (HEK) cell line that constitutively expressed blue fluorescent protein (BFP) from an integrated transgene. DSBs produced by sgRNAs that target the fluorophore in combination with Cas9 expressed from a transfected plasmid are repaired predominantly through NHEJ, with indel formation at the DSB. NHEJ-mediated gene edits are expected to result in a loss of BFP fluorescence within this HEK line. After delivery of S1m-sgRNAs and a plasmid encoding Cas9 to this HEK line, BFP expression was analyzed via flow cytometry. All S1m-sgRNAs (1, 2, and 3) created indels at approximately half the frequency of standard sgRNAs (data not shown). While the ~2-fold decrease in generating indel edits is significant, such decreases in indel formation have been linked to a concomitant decrease in off-target effects.

Figure 13:
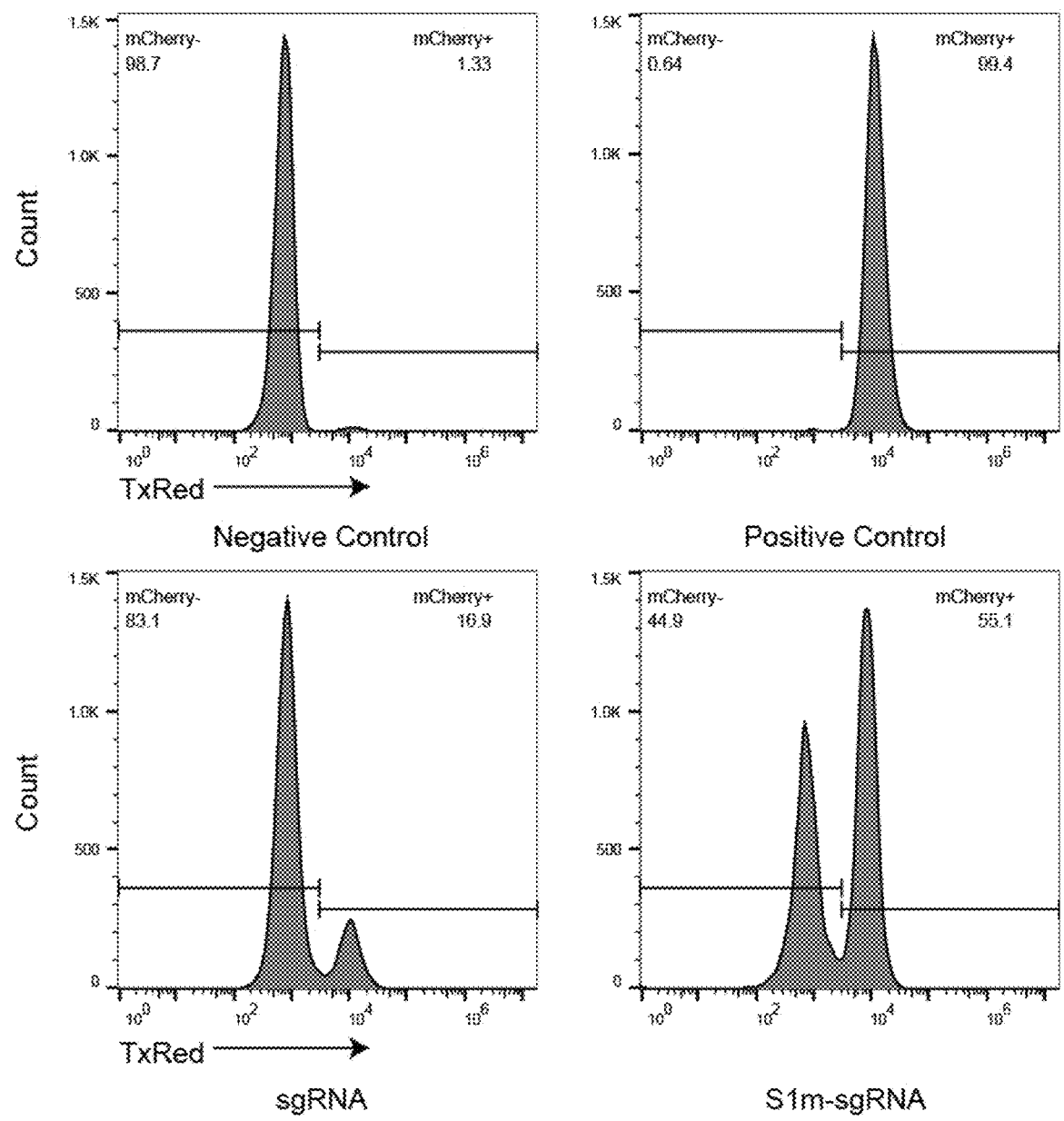
FIG. 13 shows gene editing via NHEJ using S1m-sgRNA RNPs. Knockout of integrated H2B-mCherry fluorescence in human embryonic kidney (HEK) cells. When transfected together with a plasmid encoding Sp.Cas9, S1m-sgRNAs induced ~50% the level of NHEJ as sgRNA as measured by the loss of fluorescence (44.9% vs. 83.1%) five days post transfection.

We also created a human embryonic kidney (HEK) cell line that constitutively expressed a histone 2B (H2B)-mCherry fusion protein generated by integrating a transgene into one chromosome at the safe harbor AAVS1 locus. DSBs produced by sgRNAs that target the mCherry fluorophore in combination with Sp.Cas9 expressed from a transfected plasmid will be repaired predominantly though NHEJ, with indel formation at the DSB. NHEJ-mediated gene edits are expected to create a loss of mCherry fluorescence assayed via flow cytometry. When transfected into cells, S1m-sgRNAs created NHEJ gene edits at approximately half the frequency of standard sgRNAs, knocking out fluorescence in 45% of cells compared to 83% loss by standard sgRNAs (FIG. 13). While the ~2-fold decrease in generating NHEJ edits is significant, such decreases in NHEJ activity have been linked to a concomitant decrease in off-target effects.

Example 5: Increased HDR to Indel Ratios in Human Cells

Figure 14:
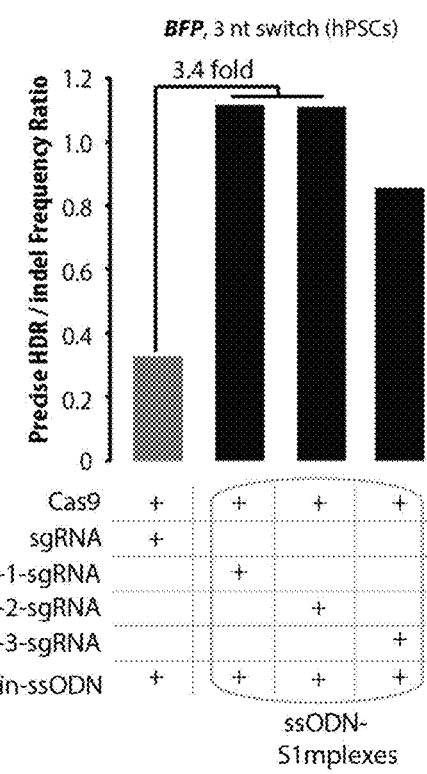
FIG. 14 shows the ratio of precise to imprecise editing using S1mplexes formed with different S1m-sgRNA variants in hPSCs. Each S1m-sgRNA increased the ratio of precise to imprecise editing when compared to sgRNAs. S1mplexes with S1m-sgRNA-1, and S1m-sgRNA-2 had the highest ratios of precise editing.

We tested the ability of all three ssODN-S1mplexes to induce HDR in a hPSC line containing a BFP-expressing transgene that can be switched to express GFP through a 3 nucleotide switch (data not shown). S1mplexes with biotin-ssODNs (ssODN-S1mplexes) were assembled using one of the three S1m-sgRNAs and compared to standard sgRNAs and ssODN combinations. After delivery of ssODN-S1mplexes and subsequent deep sequencing of genomic DNA, we found that all three ssODN-S1mplexes had a higher ratio of HDR:indel editing than standard RNPs. ssODN-S1mplexes with S1m-sgRNA-1 and S1m-sgRNA-2 induced similar ratios of HDR:indel editing while ssODN-S1mplexes with S1m-sgRNA-3 had a slightly depressed HDR:indel ratio (FIG. 14). The decreased HDR:indel ratio found using S1m-sgRNA-3 may have been due to the lower binding affinity of this sgRNA with streptavidin, as seen in the EMSA (data not shown). In order to minimize the frequency of indel mutations while maximizing HDR, we decided to use S1m-sgRNA-1 for all remaining experiments and will refer to it henceforth simply as S1m-sgRNA.

Figure 15:
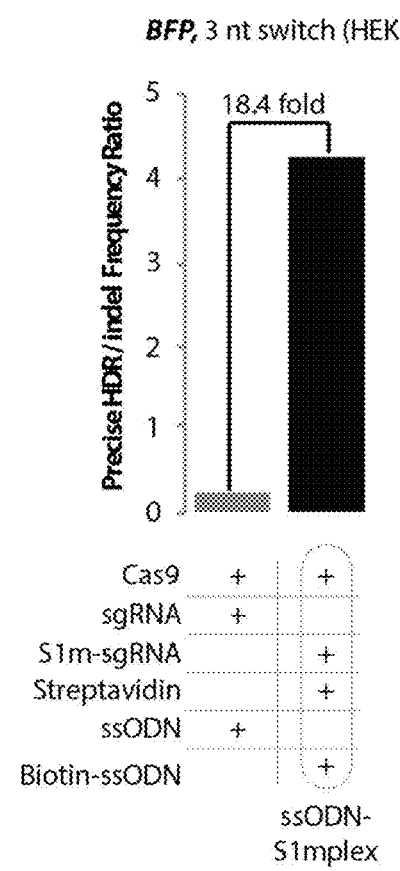
FIG. 15 shows the ratio of precise to imprecise editing at BFP locus. ssODN-S1mplexes had an 18.4-fold higher ratio than sgRNAs and contained four precise edits to every one indel as analyzed by deep sequencing 8 days post lipofection of HEKs.
Figure 16:
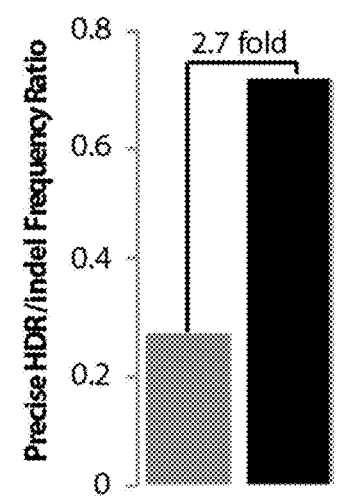
FIG. 16 shows the ratio of precise to imprecise editing at EMX1 locus. ssODN-S1mplexes had a 2.7-fold higher ratio than sgRNAs.
Figure 16:
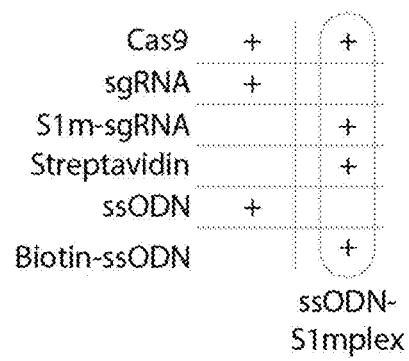

With this knowledge, we then evaluated S1mplexes in multiple human cell lines for their ability to generate a variety of precise nucleotide changes. We assembled ssODN-S1mplexes to again switch BFP to GFP. After delivery to HEK cells, deep sequencing revealed that the ssODN-S1mplexes enriched the ratio of precise insertions to imprecise editing 18.4-fold over standard RNPs and approached a ratio of four precise edits to every one indel (FIG. 15). When the same experiments were conducted in hPSCs, results from flow cytometry assays were consistent with these conclusions from deep sequencing (data not shown). Additionally, when introducing a 12 nucleotide insertion into the EMX1 locus[29] of HEKs with ssODN-S1mplexes, the ratio of precise insertions to imprecise editing increased 2.7-fold over standard sgRNA RNPs (FIG. 16 and data not shown). Taken together, this shows that ssODN-S1mplexes are able to shift the balance of editing to enrich for small, precise edits within the genome.

Figure 17:
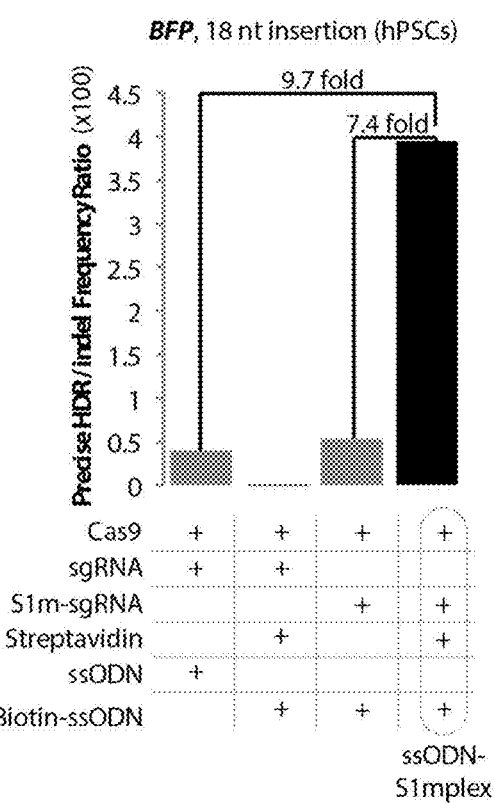
FIG. 17 shows the ratio of precise insertions to imprecise indels at BFP locus in hPSCs as analyzed by deep sequencing. ssODN-S1mplexes had a 9.7-fold increase in comparison to standard sgRNAs and a 7.4-fold increase when compared with untethered ssODNs.
Figure 18:
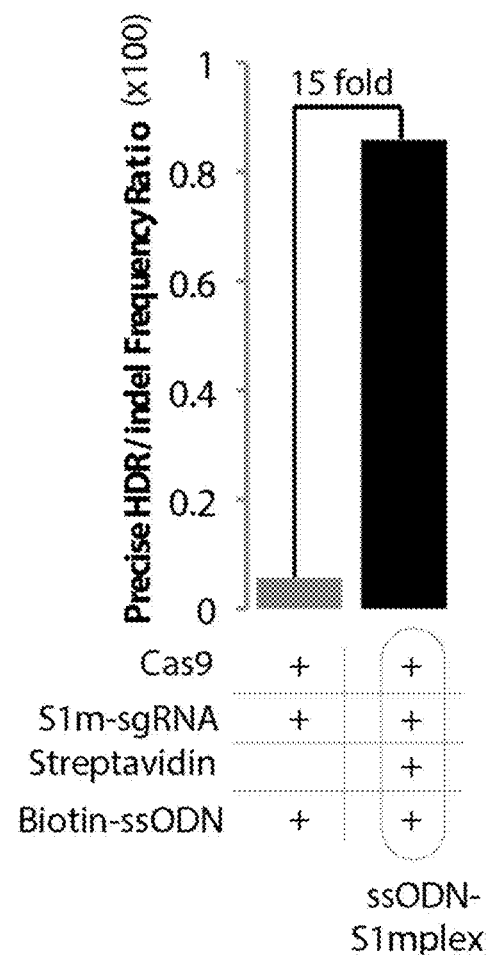
FIG. 18 shows the ratio of precise insertions to imprecise indels at EMX1 locus. Addition of streptavidin to S1mplex resulted in a 15-fold increase in the ratio of precise insertions to imprecise indels.

We tested the ability of this strategy to create even larger sequence changes in hPSCs by designing an ssODN that carried a variable 18 nucleotide insertion. We deep sequenced the cell population after delivery of ssODN-S1mplexes, again targeting the BFP and EMX1 loci. When standard sgRNA RNPs were transfected with streptavidin-ssODN complexes, minimal insertion was seen with a subsequently low ratio of precise HDR to imprecise indel alleles (FIG. 17). Equivalent precise:imprecise ratios were seen when standard sgRNA RNPs and ssODNs were transfected as when S1m-sgRNA RNPs were transfected with biotin-ssODN (without streptavidin) (FIG. 17 and data not shown). However, levels of indels were increased in the sgRNA RNP-free ssODN condition (data not shown). When the full ssODN-S1mplexes were transfected into hPSCs, HDR insertion levels greatly increased (data not shown) as did the ratio of precisely-edited to imprecisely-edited alleles to 9.7 fold over standard RNP methods (FIG. 17). Again, we observed four precise edits to every one indel with ssODN-S1mplexes at this locus. At the endogenous EMX1 locus, we delivered the S1m-sgRNA RNPs with biotin-ssODNs either with or without streptavidin. When streptavidin was added to generate the full ssODN-S1mplex, rates of insertion increased 51-fold (data not shown), and the ratio of precise to imprecise gene-editing increased 15-fold (FIG. 18). Taken together, each component of the ssODN-S1mplex is necessary to drive higher HDR:indel ratios within human cells.

Example 6: Design Constraints on the ssODN-S1mplex

Figure 19:
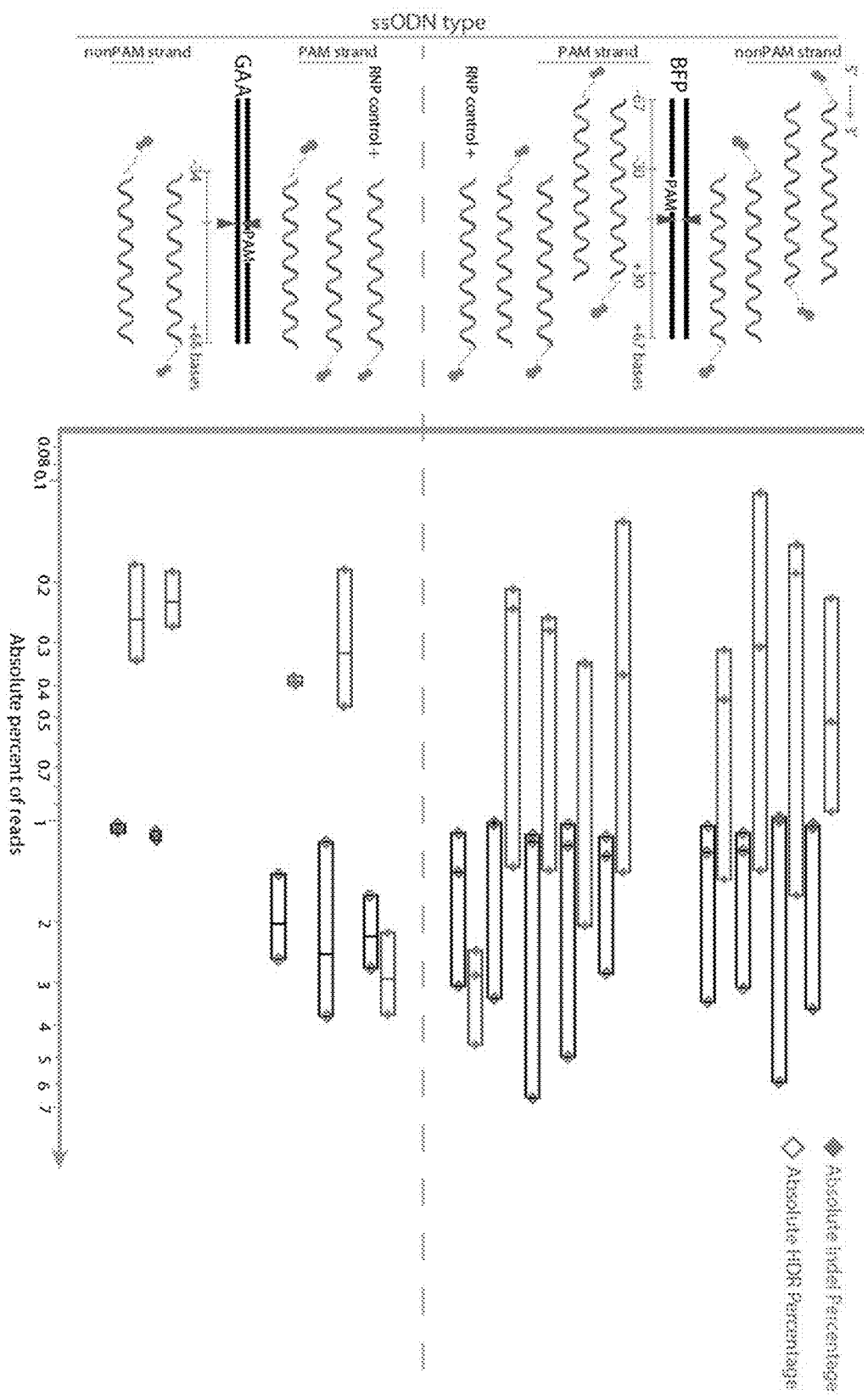
FIGS. 19 and 20: ssODN design. Genomic sequence is denoted with black bars. sgRNA targeting site and PAM is denoted by 'PAM' inside genomic locus, while red triangles are the sgRNA cut site. ssODN length is measured around cut site either upstream (−) or downstream (+) as read by the reading frame. Biotin (blue hexagon) was attached to either the 5' or 3' end of the ssODN. ssODNs were identical in sequence to either the PAM or Non-PAM sequence as read in a 5'-3' direction. RNP controls were standard sgRNAs plus corresponding ssODN.
Figure 20:
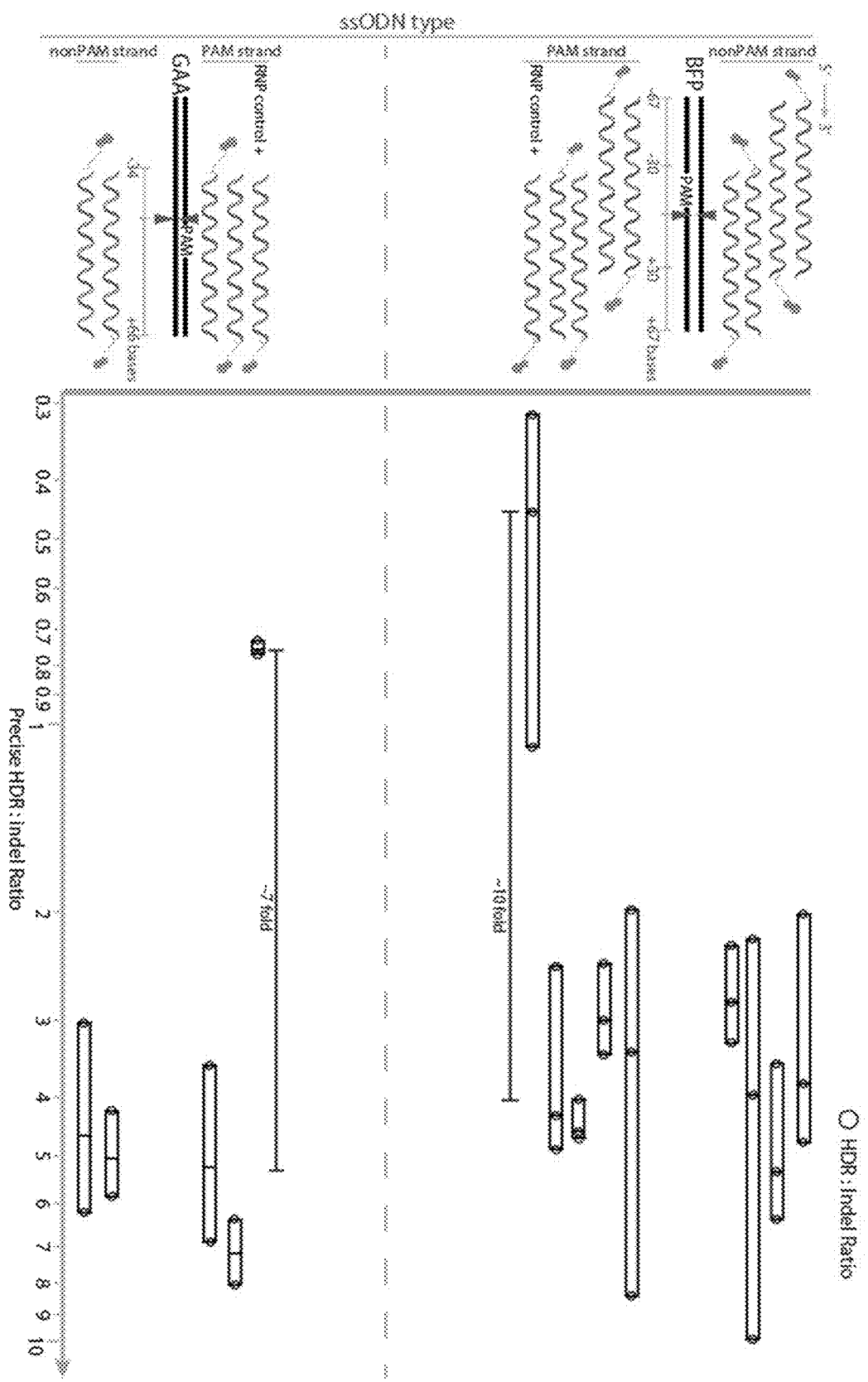

Recent studies have reported that the design of the ssODN has a significant effect on the rate of HDR. Accordingly, we explored various ssODN designs with ssODN-S1mplexes. Designs were limited to a 100 nucleotide length for ease of synthetic synthesis, but varied as follows: asymmetrical around the cut site, extending 30 upstream and 67 bp downstream or vice-versa, either identical to the sequence containing the PAM or the reverse complement (non-PAM), and biotinylated on either the 5' or 3' end of the ssODN (FIGS. 19, 20, left). S1mplexes containing each unique ssODN were assembled and transfected separately into BFP-expressing hPSCs. Four days after delivery, genomic DNA from each condition was collected and analyzed using deep sequencing. Under these conditions, 2.8±2.2% of alleles in all samples were edited via HDR and NHEJ (FIG. 19, top and data not shown). We observed that neither the asymmetry, sidedness, biotin, nor location on the ssODN had a significant effect on the HDR or indel outcomes using ssODN-S1mplexes (FIG. 19, top and data not shown). Precise editing ranged from 2-10 times greater than imprecise editing (FIG. 20, top and data not shown).

We next sought to test these ssODN designs at an endogenous GAA locus using a patient-derived hPSC line that contains a pathogenic 1 bp deletion in exon 10 on one allele. We designed sgRNAs that target only the mutant allele as well as ssODNs to correct the mutation to wildtype and modify the PAM site. These ssODNs were again asymmetrical, 34 bp upstream and 66 bp downstream from the cut site, complementary to the PAM or non-PAM strand, and biotinylated at either the 5' or 3' end of the ssODN (FIG. 19, 20, bottom). At this locus ssODN-S1mplexes again had higher levels of precise to imprecise editing than RNPs consisting of sgRNAs, with 3-8 precise edits occurring for every imprecise edit (FIG. 20, bottom and data not shown). Consistent with the sequencing results at the BFP locus, absolute levels of HDR and NHEJ editing were 2.0±1.1% (FIG. 19, 20, bottom and data not shown). There was still no significant difference between any of the ssODNs tested when complexed to the S1mplex.

Example 7: Imaging of S1mplexes Transfected Cells

Figure 21:
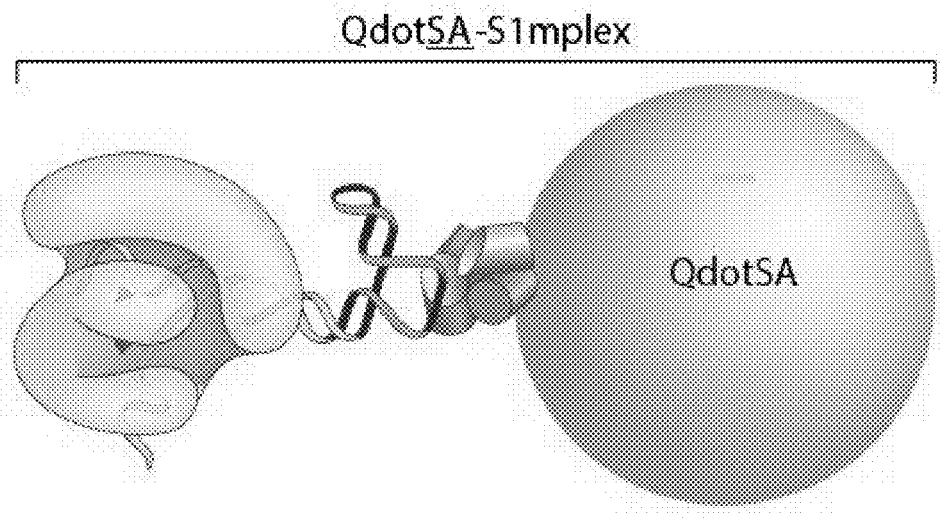
FIG. 21 is a schematic of S1mplexes with quantum dot cargoes. Qdots can be complexed with the S1mplex by a disulfide linker (Qdot-SS-S1mplex, top) or by using streptavidin covalently attached directly to the quantum dot (QdotSA-S1mplex, bottom). The quantum dot has a mean diameter of 20 nm.
Figure 21:
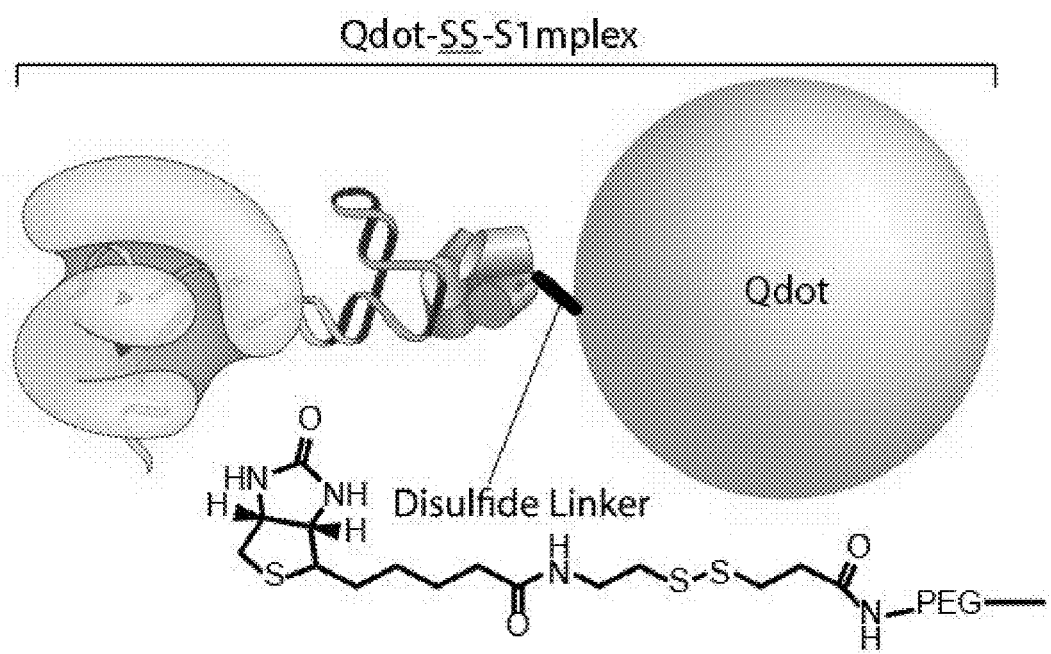
Figure 22:
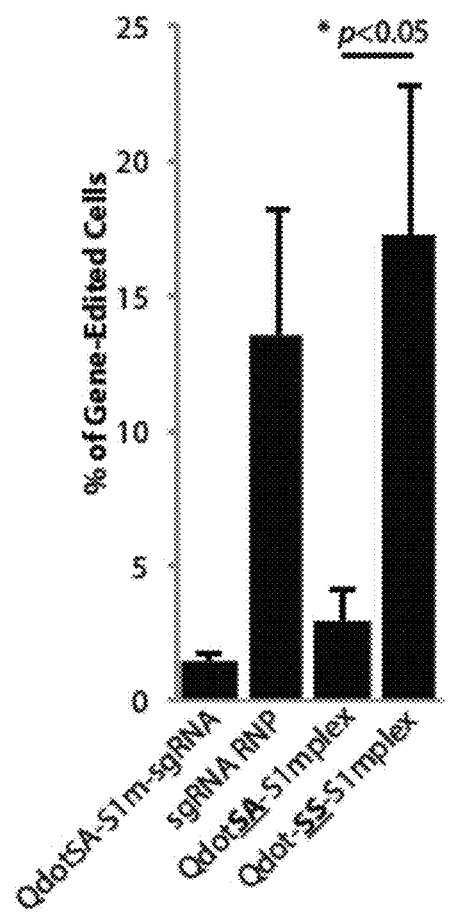
FIG. 22 shows a gene editing comparison of different Qdot S1mplexes. Gene editing of HEK H2B-mCherry reporter cells five days post sorting as assayed by flow cytometry. QdotSA interferes with RNP activity, while Qdot-SS has equivalent gene editing activity as the free RNP (n=3 technical replicates).
Figure 23:
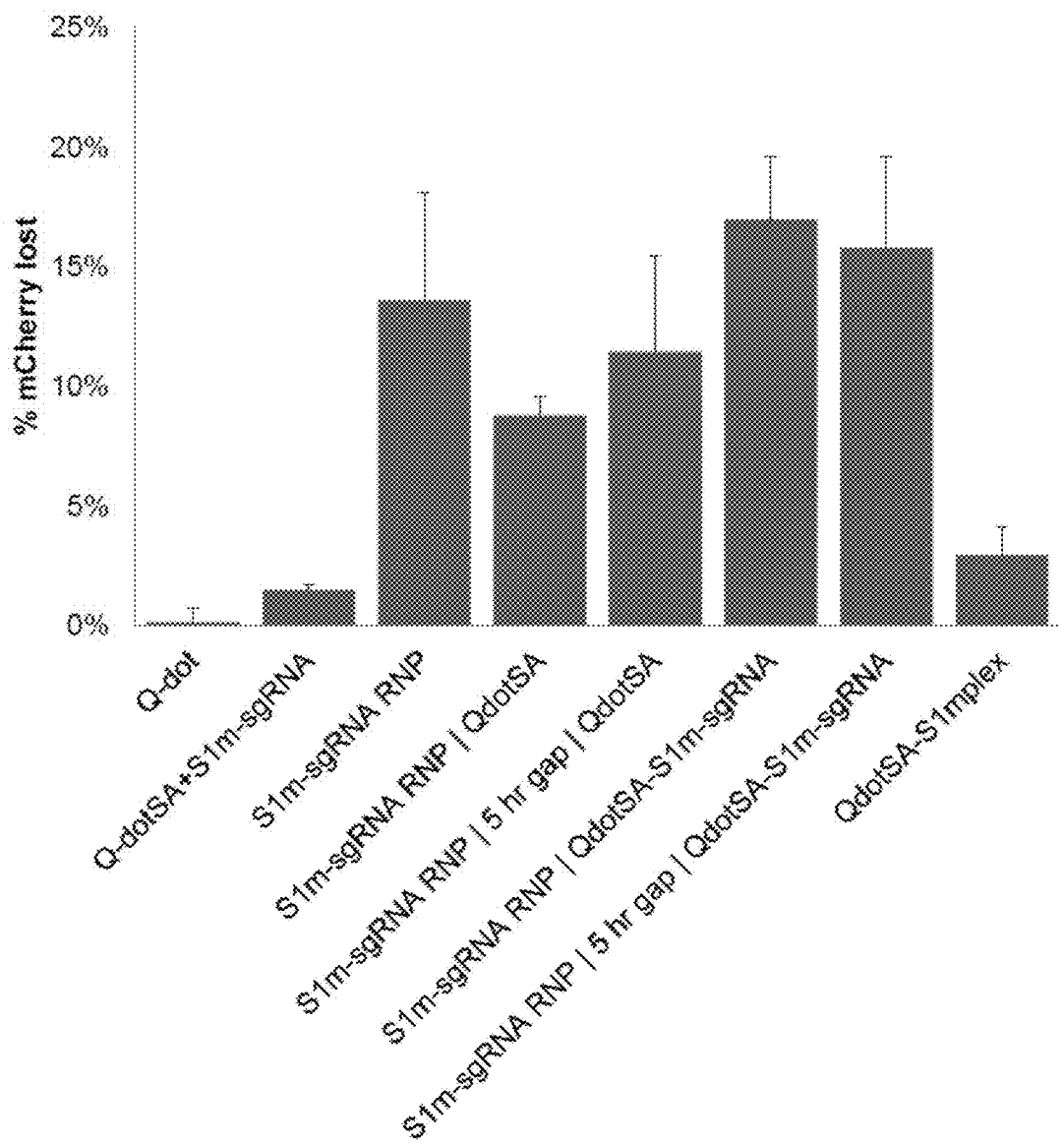
FIG. 23 shows gene-editing using various combinations of components with QdotSA. Conjugation of S1mplexes to QdotSA significantly lowers gene editing efficiency. Editing efficiency is lower even if QdotSA is transfected separately from the S1mplexes without complexation. S1m-sgR-NA|QdotSA indicates complexation of S1m-sgRNA RNP with transfection agent in a separate tube from QdotSA complexation with transfection agent, and subsequent addition of the contents of the S1m-sgRNA tube followed immediately by addition of the QdotSA tube. 5 hr. gap indicates a 5 hour culture time between transfections. Immediate application of the QdotSA can moderately interfere with the activity of the RNP, but these interference effects are abrogated if QdotSA is added 5 hours later. All RNP activity is abrogated by complexation with the QdotSA (last column) (n=3 technical replicates).
Figure 24:
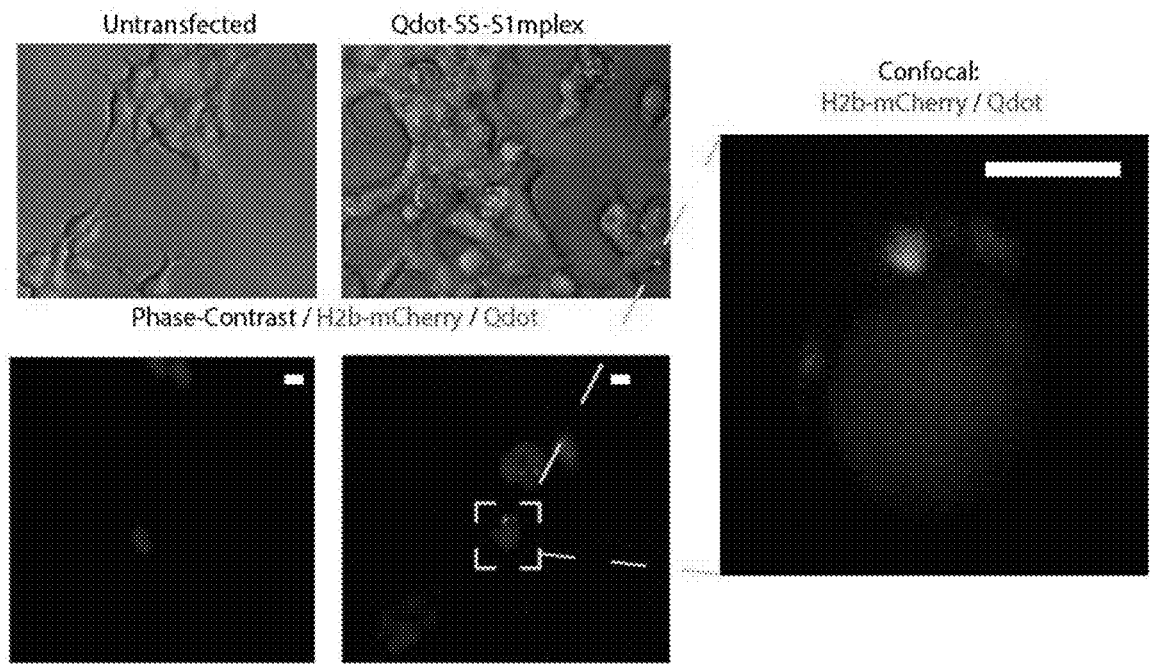
FIG. 24 shows representative epifluorescence images of untransfected and Qdot-SS-S1mplex transfected cells 24 hours post transfection (Scale bar: 10 μm). Arrowheads indicate Qdot fluorescence in the cytoplasm.
Figure 25:
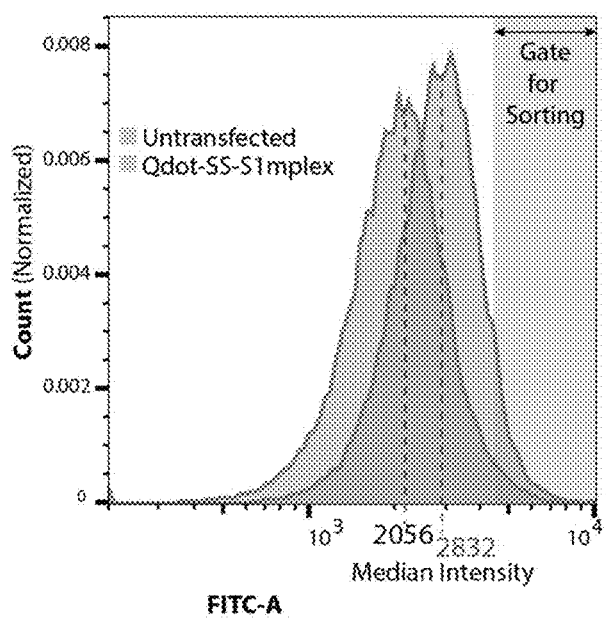
FIG. 25 shows increased fluorescence of Qdot-S1mplex allows sorting out of quantum dot positive fractions compared to untransfected cells 24 hours post transfection.
Figure 26:
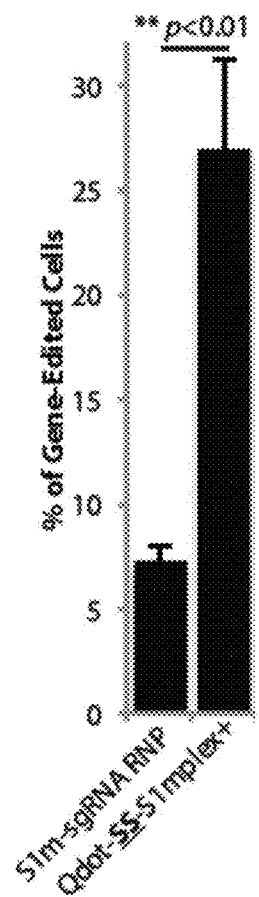
FIG. 26 shows quantum dot conjugation to S1mplex via a cleavable disulfide linker allows fluorescent enrichment of gene-edited human cells. Increased fluorescence of Qdot-S1mplex after cleavage of the disulfide linker allows sorting out of quantum dot positive fractions compared to untransfected cells 24 hours post transfection (n=3 biological replicates).

To facilitate isolation of the precisely-edited cells, we pursued a strategy to label the cells that received the S1mplexes by including additional biotinylated fluorescent cargoes. We preassembled standard streptavidin-conjugated quantum dots (QdotSA, 20 nm diameter) with S1mplexes (QdotSA-S1mplexes, FIG. 21, bottom). After transfection of QdotSA-S1mplexes, a subpopulation of cells contained Qdots within the cytoplasm. High-intensity green fluorescence dots were distributed variably across the transfected cell population, indicating that standard transfection methods likely generate significant heterogeneity in the number of RNPs delivered to each cell. Despite the presence of Qdots in the cytoplasm, no gene editing was observed upon further culture and analysis within the HEK H2B-mCherry reporter cell line (FIG. 22, FIG. 23). When the biotin linkage of the S1mplex to the Qdot was mediated through a pH-sensitive disulfide linker (Qdot-SS-S1mplex, FIG. 21, top), we observed a gain in gene editing activity (FIG. 22), while the Qdots remained largely within the cytoplasm (FIG. 24), suggesting separation and nuclear transport of the RNP. The fluorescence from the Qdot at 24 hours post transfection was utilized for fluorescence activated cell sorting (FACS). There was a shift in fluorescence for the whole cell population, indicating uptake of Qdot-S1mplexes in most cells, although to differing extents (FIG. 25). The fluorescence from the Qdot at 24 hours post transfection was utilized for cell sorting, and sorted cells with positive fluorescent signal were gene edited at 3.7-fold higher rates versus cells transfected using standard methods (FIG. 26).

Example 8: Multiplexed Gene Editing with S1mplexes

Figure 27:
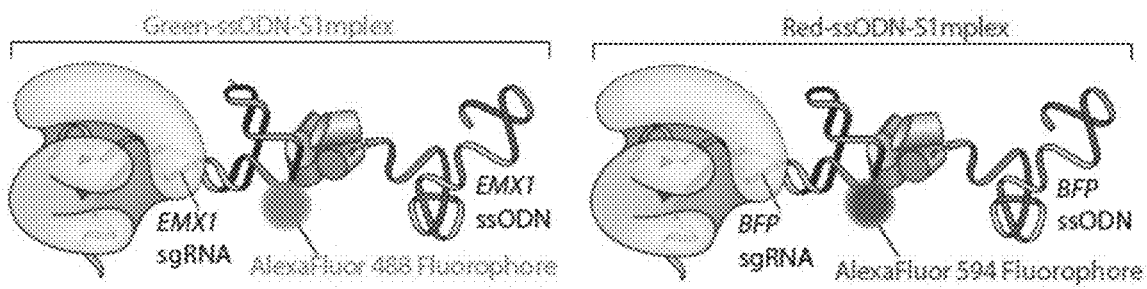
FIG. 27 shows a schematic of simultaneous editing at two loci strategy. HEK cells were transfected simultaneously with two S1m particles, labeled with distinct fluorophores. Editing at the BFP locus was associated with Red-ssODN-S1mplexes (AlexaFluor®-594 fluorophore), while editing at the EMX1 locus was associated with Green-ssODN-S1mplexes (AlexaFluor®-488 fluorophore).
Figure 28:
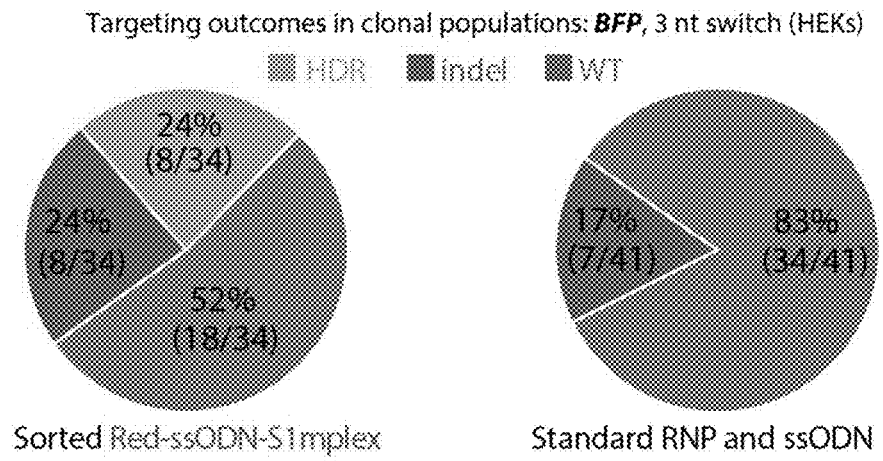
FIG. 28 shows single cells sorting for enrichment of editing at BFP locus. In enriched S1mplex clonal populations, indels (brown) and HDR (blue) events occurred in a 1:1 ratio. In sgRNA clones, all isolated clones either had indel or wildtype genotypes. Genotypes were assayed by Sanger sequencing. No mosaic genotypes were observed.
Figure 29:
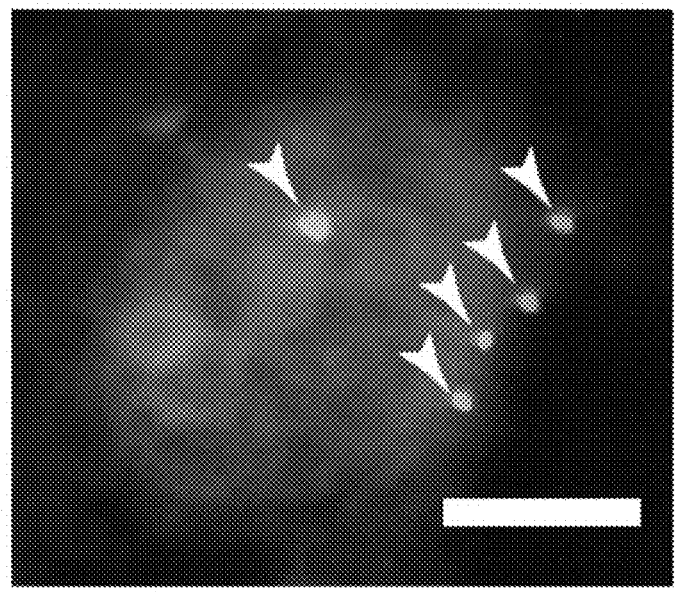
FIG. 29 shows fluorescent S1mplexes inside the cell using confocal microscopy. Arrows denote Green-S1mplex both inside the nucleus and outside the cell (Scale bar: 10 μm).

To obtain further control and refine the mutagenic spectrum of S1mplexes, we attached a fluorescent label directly to streptavidin that could be used for identification during flow cytometry. We preassembled an S1m-sgRNA and biotin-ssODN targeting BFP with a streptavidin labeled with a red fluorophore (AlexaFluor®-594) (FIG. 27) and then performed a single cell FACS for the isolation of clones that had high fluorescence after delivery. Upon further cell culture, clones were analyzed by Sanger sequencing for editing at the BFP locus. Of the 34 isolated clones in the S1mplex-positive population, eight underwent HDR; eight harbored indels; and, the rest remained unedited (FIG. 28). In comparison, when using sgRNAs, seven of the 41 isolated clones harbored indels and none were positive for HDR. Cell populations did not contain mosaic gene editing, indicating that defined gene editing outcomes could be enriched by FACS on the S1mplex fluorescence. Using this capability we tested whether if it was possible to multiplex edits using differently colored S1mplexes. We thus assembled the same ssODN-S1mplex targeting BFP, termed red-ssODN-S1mplex, and separately complexed an S1m-sgRNA and biotin-ssODN targeting EMX1 with a streptavidin labeled with a green fluorophore (AlexaFluor®-488), termed green-ssODN-S1mplex (FIG. 27). The two ssODN-S1mplexes were mixed and transfected simultaneously into HEKs (FIG. 29).

Figure 30:
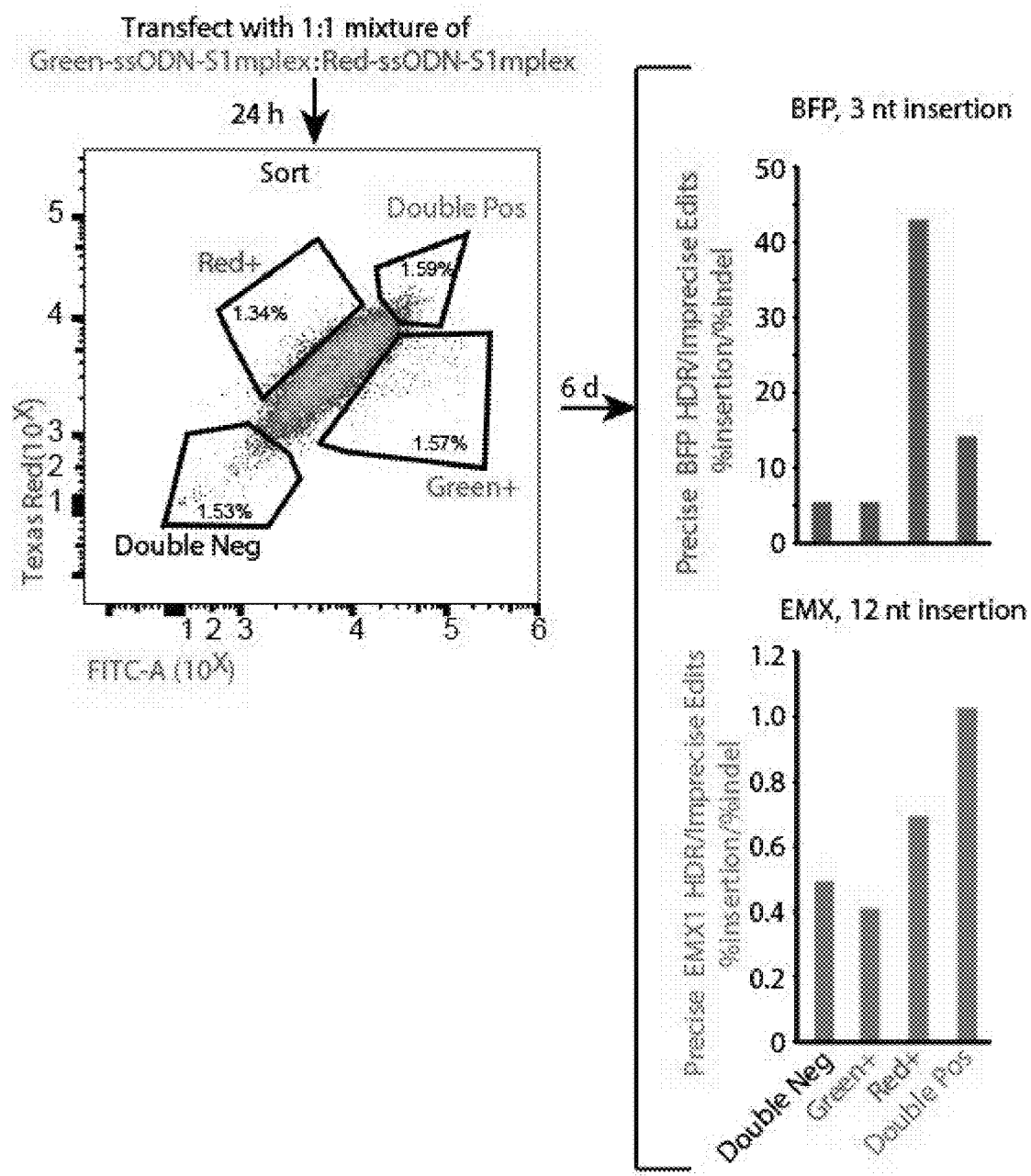
FIG. 30 shows twenty-four hours post transfection, cells were sorted into populations that were positive for either fluorophore, both or neither. Analysis via deep sequencing was done 6 days post sorting. Top: ratio of precise (perfect sequence match to ssODN) to imprecise editing (indels) in sorted populations. Populations enriched for BFP targeted S1mplexes (Red+ and double positive) had elevated ratios up to 40 times as many insertions as indels. Bottom: ratio of precise to imprecise editing in sorted populations. Populations enriched for EMX1 targeted S1mplexes (Red+ and double positive) had elevated ratios of precise insertions to indels.
Figure 31:
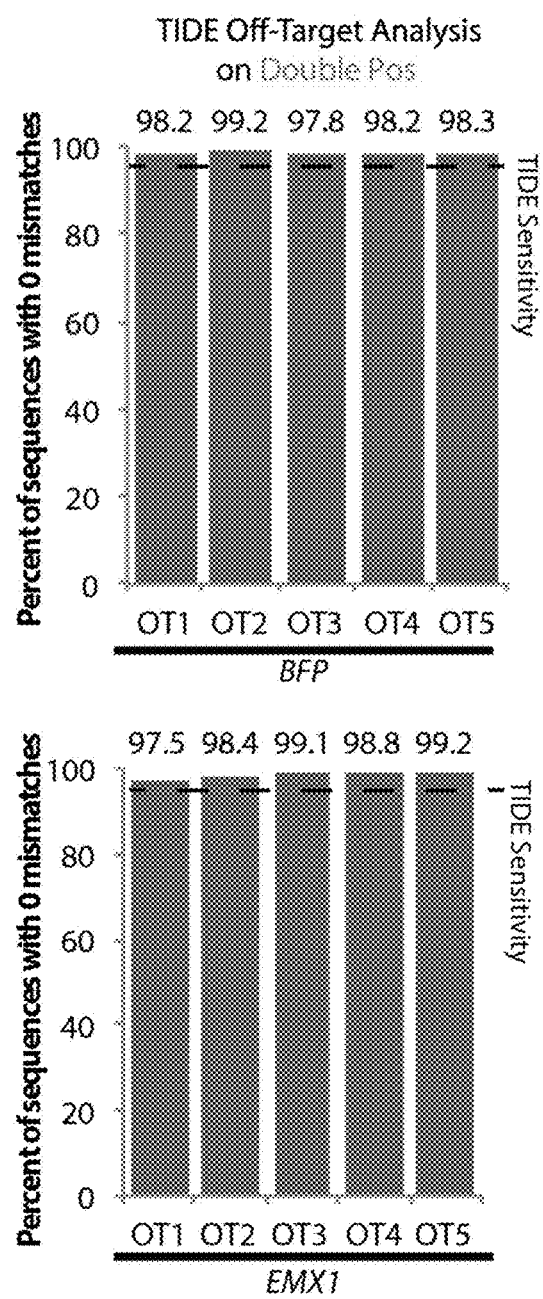
FIG. 31 Off-target analysis of double positive populations using TIDE at the top 5 off-target locations for each sgRNA. No modifications were detected below the TIDE limit of detection (dotted line).

Twenty-four hours post transfection, we sorted cells using FACS into one of four populations: positive for either fluorophore, both, or neither (FIG. 30). Only the top 2% of each population was taken, as we observed some association of the fluorescent S1mplex with the cell membrane in addition to robust fluorescent signal within the nucleus of some of the cells (FIG. 29). One-week post sort, each of the four populations was analyzed for editing via deep sequencing as well as by flow cytometry for BFP editing or insert-based PCR for EMX1. Deep sequencing revealed that editing at the EMX1 locus was increased in the presence of green-ssODN-S1mplexes (Green+ and double positive fractions) (FIG. 30, and data not shown). In these populations the ratio of precise to imprecise edits increased and approached one and was 2-fold greater than that of the double negative fraction (data not shown). Similarly, editing at the BFP locus was increased in the Red+ and double positive fractions. As was seen in previous deep sequencing experiments, the ratio of precise to imprecise edits was elevated in the presence of S1mplexes. With the addition and sorting of fluorescent S1mplexes, the ratio was greater than 10 insertions per indel (FIG. 30 and data not shown). Interestingly, the level of indels was highest in the double negative fraction (data not shown); this may be due to the presence of unlabeled RNPs that did not complex with streptavidin. Results with conventional flow cytometry and PCR assays followed the same trends, consistent with these conclusions from deep sequencing data not shown). We analyzed the top 5 off-target sites for both the BFP and EMX1 sgRNAs using TIDE[31] in the sorted fractions as well as previous samples used for deep sequencing. None of the sorted populations using ssODN-S1mplexes had modifications above the TIDE limit of detection (FIG. 31, data not shown). However, using standard sgRNA RNPs, notable off-target mutagenesis occurred at EMX1 off-target site 2 (data not shown). Taken together, the assembly of S1mplex particles with a fluorescent tag can be used to create multiple, precise edits with increased efficiency without needing multiple transfections or extended culture.

Figure 32:
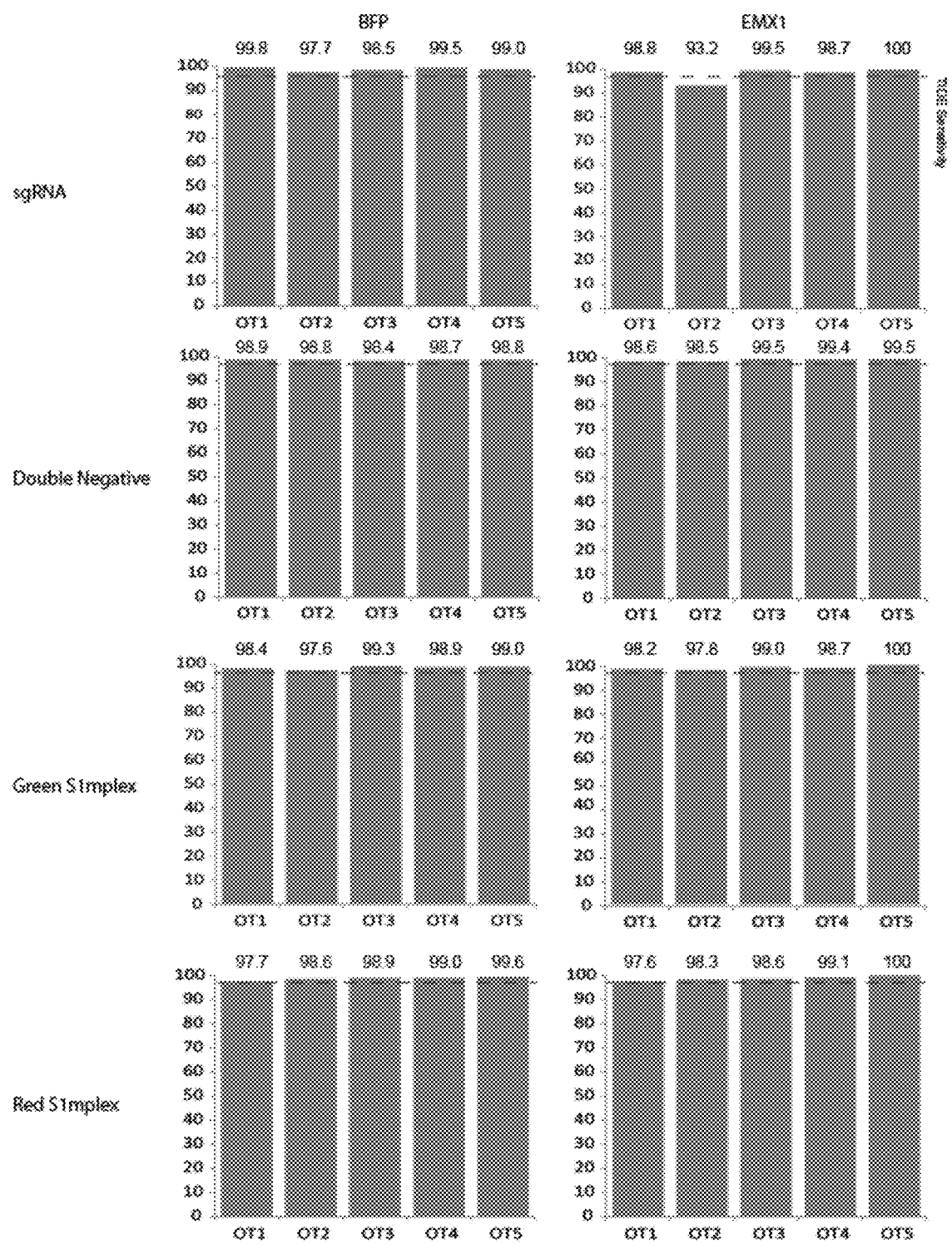
FIG. 32 shows an off-target analysis of sorted S1mplex populations. Off-target analysis using TIDE software at the top 5 predicted off-target sites within the human genome at the BFP and EMX1 loci. Y axis indicates the percentage of cells with 0 mismatches from the parental sequence (perfect matches in sequencing reads). None of the sorted S1mplex populations showed off-target effects above the limit of detection. The unsorted sgRNA RNP population had a small proportion of cells that may have been edited at OT-2 of the EMX1 off-target sites.

We analyzed the top 5 off-target sites for both the BFP and EMX1 sgRNAs using TIDE in the sorted fractions as well as previous samples used for deep sequencing. None of the sorted populations using ssODN-S1mplexes had modification above the limit of detection (FIG. 32). However, using standard sgRNA RNPs, notable off-target mutagenesis occurred at EMX1 off-target site 2 (FIG. 32). Taken together, the pairing of S1mplex particles with a fluorescent tag can be used to create multiple, precise edits with increased efficiency without needing multiple transfections or extended culture.

Figure 33:
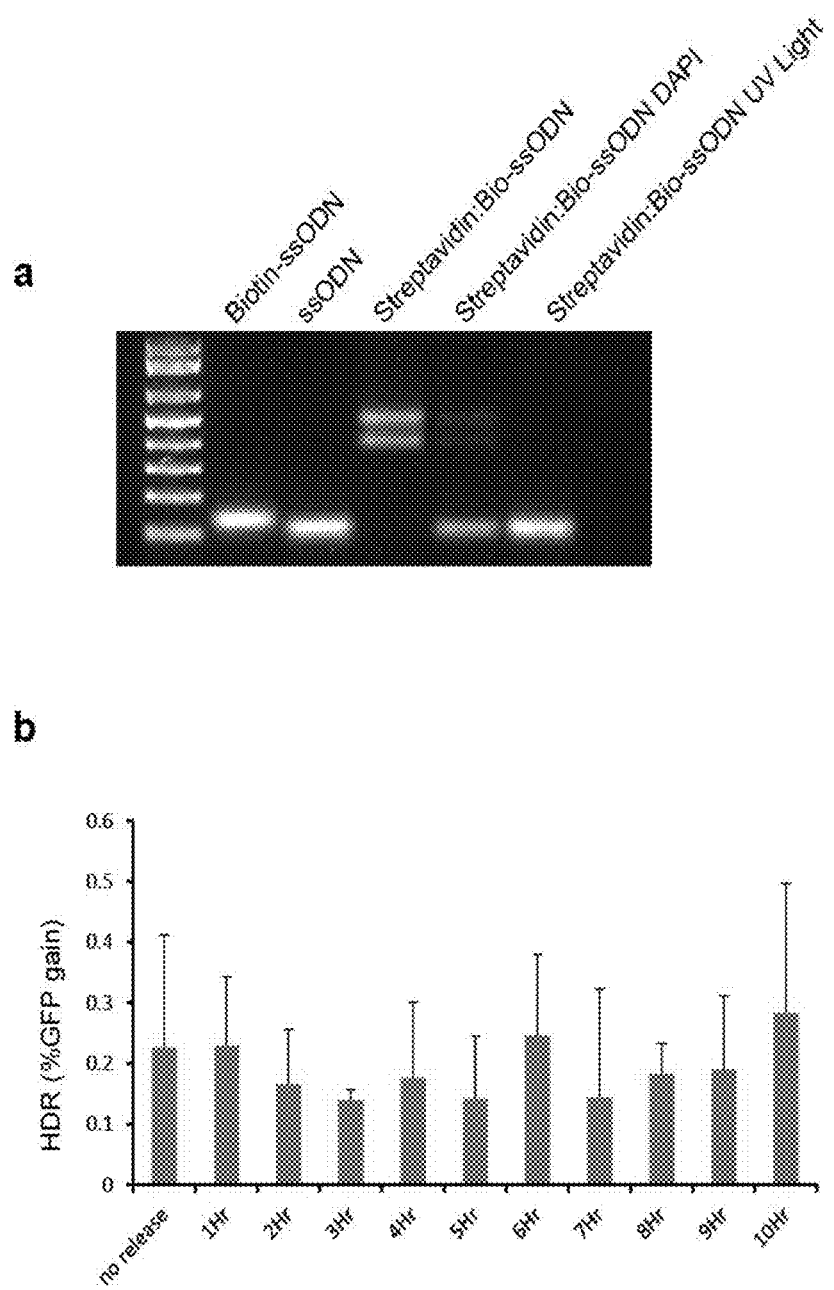
FIG. 33 shows release of a biotin-ssODN through a photocleavable linkage had no significant effect on HDR editing.

FIG. 33 shows release of a biotin-ssODN through a photocleavable linkage had no significant effect on HDR editing. FIG. 33a shows a biotin-ssODN that contained a UV-cleavable linker was attached to streptavidin and S1mplex particles in order to study the potential of releasing the ssODN inside the cell to promote HDR. Lane 1: DNA standard. Lane 2: Photo-cleavable biotin-ssODN. Lane 3: standard ssODN. Lane 4: Binary complexes of streptavidin and photo-cleavable biotin-ssODNs. Lane 5-6: Binary complexes cleaved by either exposure to light through a DAPI filter cube (lane 5) or exposure to a UV transilluminator (lane 6). DAPI filter cube cleaved nearly all ssODN after 10 minutes whereas transilluminator had complete cleavage. Cleaved DNA product was the same length as control standard ssODN. FIG. 33b shows release of biotin-ssODN by 15 minutes of light exposure through a DAPI filter cube every hour post transfection. Levels of HDR were not significantly affected by the release of the ssODN within the cell at any time point (n=3 biological replicates).

Conclusions from Examples 1-8

The S1mplex strategy provides a straightforward, robust and modular method to regulate the gene editing activity of Sp.Cas9 RNPs. RNA modification of the sgRNA with S1m can be performed readily through short nucleic acid synthesis methods, whereas other methods that engineer the Cas9 protein can add challenges in protein expression, purification and stability. Our strategy could complement and add functionality to generate engineered variants (e.g., high fidelity, switchable, and optogenetic nucleases). Pre-assembled S1mplexes could also be readily manufactured to be off-the-shelf reagents with well-defined critical quality attributes appropriate for clinical use: avidin has previously been tolerated in clinical trials and clinical grade Sp.Cas9 is available from several vendors.

Gene editing in human cells could be controlled by the linkages within the S1mplex. For the Qdot-S1mplexes, a gain of RNP activity occurred after switching to a labile disulfide bond. Without being held to theory, it is believed that large cargoes such as Qdots (20 nm diameter) complexed with the RNP inhibit Cas9 nuclease activity. The smaller ssODN-S1mplexes without labile bonds with mean diameters of 16 nm could generate edits at target loci. The Qdot-S1mplex results demonstrate that the biotin-streptavidin linkage is strong enough to associate biotinylated cargoes with the RNP, while disulfide bonds, which are enzymatically labile at low pH, likely dissociate the S1mplex in low pH endocytotic trafficking compartments and release the RNP from the cargo to fully recover activity. Regulating CRISPR gene editing tightly through the release of large cargoes could be explored with other chemistries that generate labile cargoes upon excitation by light or heat. Such strategies could advance targeted therapy to specific areas and cell types within the body.

Figure 34:
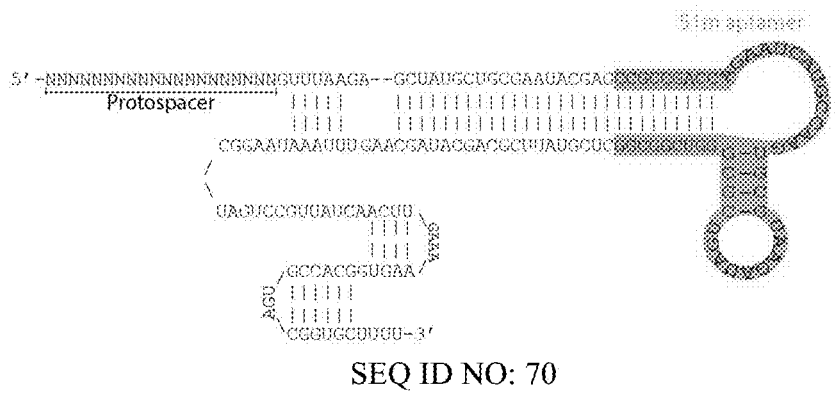
FIG. 34 is a schematic of the structure and sequence of S1m-sgRNA-V3. This sequence removes 6 nt from the beginning of the S1m aptamer. Removal of these nucleotides simplified the secondary structure of the RNA. This modification may potentially decrease the number of incorrectly folded and therefore inactive S1m-sgRNAs.

The site-specific complexation of the HDR donor template with the RNP through a biotin-streptavidin noncovalent interaction and an S1m RNA aptamer-streptavidin interaction favored precise gene editing outcomes at a ratio of ~1-10 precise edits to each indel. Absolute levels of precise editing decreased as the length of insertion increased, which has been shown previously, and we anticipate that even higher ratios of precise to imprecise editing could be generated for single nucleotide changes. 44,750 disease-associated single nucleotide or indel mutations in the ClinVar database can be corrected, in principle, by HDR via donor templates of 1-50 nucleotides in length. While dissociation of the RNP from its complexed quantum dot cargo was required for Cas9 activity, release of the biotin-ssODN through a photocleavable linkage had no significant effect on HDR editing (FIG. 34). Using a different chemistry in mouse cells, biotin-ssODNs could be recruited to RNPs within the cell produced by translation of injected Cas9-avidin mRNA. Increased local concentration of biotinylated donor template at the DSB through the streptavidin bridge of the S1mplex could be one mechanism that increases precise editing. Other potential mechanisms include differential modification of the ssODN ends to promote strand invasion or enhance stability within the cells, and a more defined stoichiometry of the RNP to the ssODN within each cell. Further modifications to the ssODN template and linkers could be used to dissect these gene editing mechanisms. The S1mplex strategy coupled with the variety of conjugatable biotinylated reagents enables the formation of a versatile toolkit centered around precise gene editing to advance gene editing scientific development and gene therapy.

Additional Materials and Methods

S1m-sgRNA-V3 was generated in a similar fashion but scaffold PCR was performed under different conditions. Phusion® PCR was performed using the following thermocycling protocol: 30 cycles of 98° C. for 10 s and 72° C. for 15 s with a final extension period of 72° C. for 10 min. These scaffolds were then combined with the same second primer as in S1m-sgRNA-1 but cycled for 30 cycles of 98° C. for 10 s and 60° C. for 10 s and 72° C. for 15 s with a final extension period of 72° C. for 10 min.

LysoSensor™ Quantification.

H9 hESCs and Pompe iPSCs were harvested and counted to establish correct cell number ratios prior to being plated on glass-bottom well slides (Ibidi™). Cells were allowed to attach for 24 hours prior to analysis. Cocultures were stained with LysoSensor™ Green (1:1000) and Hoescht33342 (1:2000) for 5 minutes followed by 2× washes with PBS. Images were obtained using confocal microscopy (Nikon AR-1) and analyzed using CellProfiler.

Creation of ArrayEdit Platform.

μCP was performed using previously described methods. The surface modification involved printing of an alkanethiol initiator to nucleate the polymerization of hydrophilic poly (ethylene glycol) (PEG) chains. Briefly, double sided-adhesive was attached to the bottom of a standard tissue culture plate, after which a laser cutter was used to cut out the well bottoms. Glass sheets were purchased at a size slightly smaller than a well plate. A metal evaporator was then used to deposit a thin layer of titanium, followed by a layer of gold onto one side of the glass sheet. Using previously described chemistry, patterns were transferred to gold-coated glass via a polydimethylsiloxane stamp after which the glass was submerged in a poly(ethylene glycol) (PEG) solution overnight to build hydrophillic PEG chains surrounding μFeatures. After submersion, sheets were washed with deionized water to remove residual copper deposited by the reaction and 70% ethanol to sterilize. Standard tissue culture plates with well bottoms cut out were then fastened to processed sheets using a custom-made alignment device.

Biallelic Correction of Pompe iPSC.

All hPSC transfections were performed using the 4D-Nucleofector™ System (Lonza) in P3 solution using protocol CA-137. Cells were pretreated with Rho-kinase (ROCK) inhibitor (Y-27632 Selleck Chemicals) 24 hours prior to transfection. 50 pmol Cas9, 60 pmol sgRNA, 50 pmol streptavidin, and 60 pmol ssODN were used to form particles per ssODN-S1mplex as described above. Cells were then harvested using TryPLE™ (Life Technologies) and counted. $2 \times 10^5$ cells per transfection were then centrifuged at 100×g for 3 minutes. Excess media was aspirated and cells were resuspended using 20 μL of RNP solution per condition. After nucleofection, samples were incubated in nucleocuvettes at room temperature for 15 minutes prior to plating into $3 \times 10^4$ cells per well of an ArrayEdit plate containing mTeSR1+10 μM ROCK inhibitor. Media was changed 24 hours post transfection and replaced with mTeSR1 medium.

High-Content Image Acquisition and Analysis.

Automated microscopy was performed using a Nikon Eclipse TI epifluorescent microscope and NIS Elements Advanced Research (V4.30) software. The ND acquisition 6D module was used to establish a 20×20 grid pattern such that one 10× image was taken at each μfeature and combined in a single file. Nikon Perfect Focus was used to ensure that all images were in the same Z-plane and in focus. Each image was then corrected for illumination defects using CellProfiler and the number of nuclei was determined as well as LysoSensor™ intensity and S1mplex presence within the cell.

Dual S1mplexes for the Excision of Genomic DNA.

Two different s1m-sgRNA-1 sequences, cutting ~238 bps apart in the LAMA5 locus were designed (target sequences+ PAM: GTAGCCGGGGAAGCGAAGCA-GGG (SEQ ID NO: 58) and GCTCACGGACGGCTCCTACC-TGG (SEQ ID NO: 59)) and sgRNAs for these sequences were made through in vitro transcription. One day prior to transfection, HEK 293 cells were seeded at ~5,000 cells/well in a 96 well plate. Prior to transfection, first, RNPs were formed by mixing each S1m-sgRNA at a 1:1 molar ratio with Cas9 protein separately. Dual S1mplexes were then formed by mixing the two different RNPs with streptavidin at a 1:1:1 molar ratio. S1mplexes were then mixed with Lipofectamine™ (100 ng Dual S1mplexes mixed with 0.75 uL Lipofectamine™ 2000 per well) and used to transfect the HEK293 cells. Three days post transfection, cells were harvested and genomic DNA extracted as described previously. A 744 bp portion of the LAMA5 locus spanning both targets was amplified using PCR (With primers CCC-CATCGTTCCATCTCCTCT (SEQ ID NO: 60) and CGCGGGTTCTTTTGGTATCTTG (SEQ ID NO: 61)) and band intensities of unaffected and excised portions were used to quantify excision efficiency.

TABLE 7 primers

| S1m Construct Name | SEQ ID NO: | Sequence (5' to 3') |
|---|---|---|
| S1m_V3_F | 62 | GTTTAAGAGCTATGCTGCGAATACGAGCCGCCG ACCAGAATCATGCAAGTGCGTAAGATAGTCGCG GGTCGGCGGCTCGTATTC |
| S1m_V3_R | 63 | AAAAGCACCGACTCGGTGCCACTTTTTCAAGTT GATAACGGACTAGCCTTATTTAAACTTGCTATG CTGCGAATACGAGCCGCCGACCCG |
| S1m1 Forward | 64 | TTAATACGACTCACTATAGGNNNNNNNNNNNNNN NNNNNNNGTTTAAGAGCTATGCTGCGA |
| S1m-SL2_F | 65 | GTTTAAGAGCTATGCTGGAAACAGCATAGCAAG TTTAAATAAGGCTAGTCCGTTATCAACTTCGAA TACGAGATGCGGCCGCCGACCAGA |

TABLE 7-continued primers

| S1m Construct Name | SEQ ID NO: | Sequence (5' to 3') |
|---|---|---|
| S1m-SL2_R | 66 | AAAAAAAGCACCGACTCGGTGCCACTTTTTCCG AATACGAGATGCGGCCGCCGACCCGCGACTATC TTACGCACTTGCATGATTCTGGTCGGCGGC |
| S1m-SL3_F | 67 | GTTTAAGAGCTATGCTGGAAACAGCATAGCAAG TTTAAATAAGGCTAGTCCGTTATCAACTTGAAA AAGTGGCACCGAGTCGGTGCCGAA |
| S1m-SL3_R | 68 | AAAAAAACGAATACGAGATGCGGCCGCCGACCC GCGACTATCTTACGCACTTGCATGATTCTGGTC GGCGGCCGCATCTCGTATTCGGCACCGACT |
| RNATracR | 69 | AAAAGCACCGACTCGGTGCC |

TABLE 8 protospacers and respective PAMs used for genomic targeting

| sgRNA Name | SEQ ID NO: | Sequence (5' to 3') | PAM |
|---|---|---|---|
| BFP (BFP→GFP) | 71 | GCTGAAGCACTGCACGCCAT | GGG |
| mCherry (mCherry_15) | 72 | GGAGCCGTACATGAACTGAG | GGG |
| GAA ΔT | 73 | CTCGTTGTCCAGGTAGGCCC | GGG |
| GAA X746 | 74 | TGGACCACCAGCTCCTGTGG | GGG |

Example 9: Variants of S1m-Sg RNA: Variable Length of S1m Linker

Figure 35:
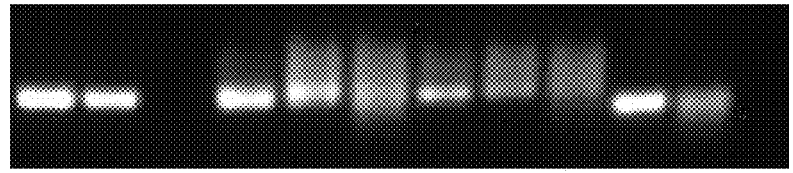
FIG. 35 shows the binding capability of S1m-sgRNA-1 and S1m-sgRNA-V3 with streptavidin using an electrophoretic mobility shift assay (EMSA). S1m-sgRNAs or standard sgRNAs were mixed with native streptavidin protein at the indicated ratios (w/w) and allowed to complex prior to being loaded on an agarose gel. Lane 1: S1m-sgRNA-1. Lane 2: S1m-sgRNA-V3. Lane 3: Streptavidin. Lane 4: 10:1 S1m-sgRNA-1:Streptavidin. Lane 5: 1:1 S1m-sgRNA-1:Streptavidin. Lane 6: 1:10 S1m-sgRNA-1:Streptavidin. Lane 7: 10:1 S1m-sgRNA-V3:Streptavidin. Lane 8: 1:1 S1m-sgRNA-V3:Streptavidin. Lane 9: 1:10 S1m-sgRNA-V3:Streptavidin. Lane 10: sgRNA. Lane 7: 1:10 sgRNA:Streptavidin.

We have created two different S1m-sgRNA versions that may serve different functions for downstream applications. Importantly, we have shown that the exact sequence of the construct is malleable and can be fine-tuned as desired. S1m-sgRNA-1 has a longer stem loop and may demonstrate more degrees of freedom in solution or when bound to Cas9 to form an RNP. This structure may have advantages when attaching larger cargoes such as additional proteins that may cause steric interference with Cas9 protein. Similarly S1m-sgRNA-V3 (FIG. 34) contains a shorter stem loop linking the sgRNA and S1m aptamer. This structure may be easier to fold in to the correct secondary structure due to the decreased complexity of the sequence and fewer binding partners for each nucleotide in the sequence. This sequence may also be amenable to synthetic construction methodologies that are length limited to preserve fidelity of the final product We next texted the capability of both sgRNAs to bind to streptavidin through an electrophoretic mobility shift assay (FIG. 35). Both sgRNAs showed a similar shift on the gel suggesting the same binding capability of both aptamer constructions. This is as we expected as the core sequence and therefore secondary structure of the streptavidin binding region is unchanged. However, with this assay we are unable to distinguish the portion of S1m-sgRNAs that are folded correctly. Both S1m-sgRNA-1 and V3 showed similar upward mobility following EMSA suggesting the presence of larger complexes within the solution. In comparison, no so shift was observed when mixing sgRNAs with streptavidin.

Figure 36:
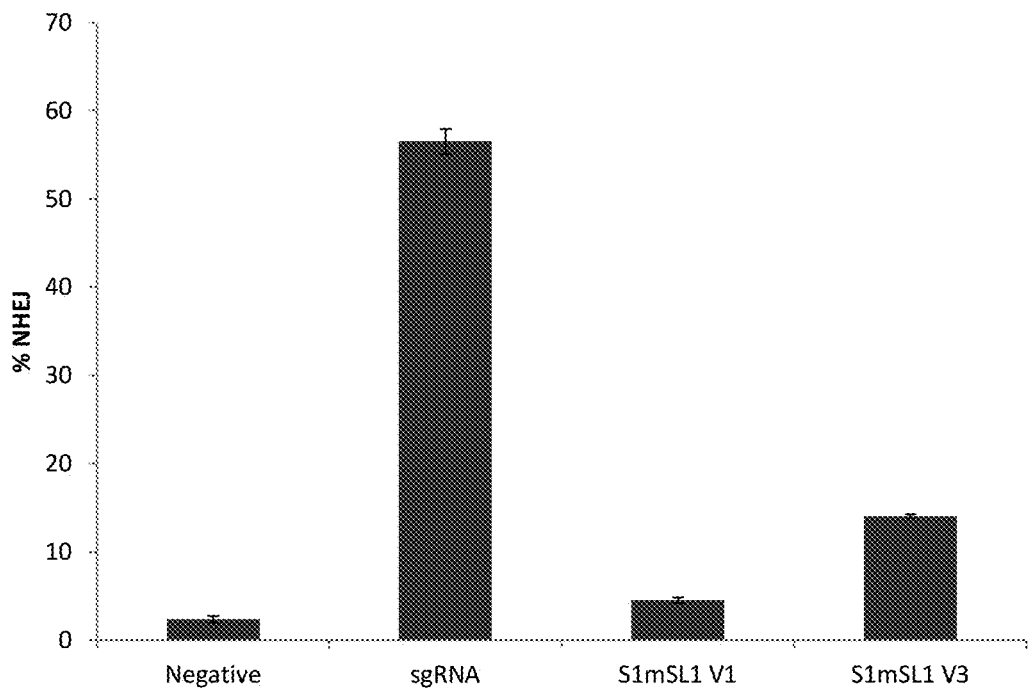
FIG. 36 shows the induction of NHEJ using various sgRNAs. Cas9 RNPs were formed with standard sgRNA, S1m-sgRNA-1, or S1m-sgRNA-V3 targeting the same locus and transfected into H2b-mCherry expressing HEK cells. % NHEJ was measured by loss of fluorescence 7 days post transfection. Both S1m-sgRNA versions were less effective at creating double strand breaks repaired by NHEJ than standard sgRNA. S1m-sgRNA-V3 induced more NHEJ events than V1 (~3-fold higher) potentially due to simplified secondary structure. Both S1m-sgRNA variants were still capable of creating genetic modifications. (n=3 technical replicates. Error bars represent ±1 S.D.)

A core capability of the CRISPR/Cas9 system is the ability to create double strand breaks that are subsequently repaired by cellular mechanisms. To test this capability with S1m-sgRNAs we transfected Cas9 RNPs containing an sgRNA in targeting the fluorophore (Table 8) into H2b-mCherry expressing HEK cells and tested for the loss of fluorescence after 7 days. Both S1m-sgRNA variants induced fewer NHEJ events than a standard sgRNA (FIG. 36). While this loss of function is significant, it may lend greater utility to S1m-sgRNAs in applications relating to precise editing. In clinical settings, the high level of uncontrolled NHEJ products is undesirable. Between the two S1m-sgRNA variants, V3 induced ~3-fold higher NHEJ events than S1m-sgRNA-1. This may be due to a higher number of active sgRNAs within the transfected pool and may also suggest that V3 is more suitable to targeted deletion strategies.

Figure 37:
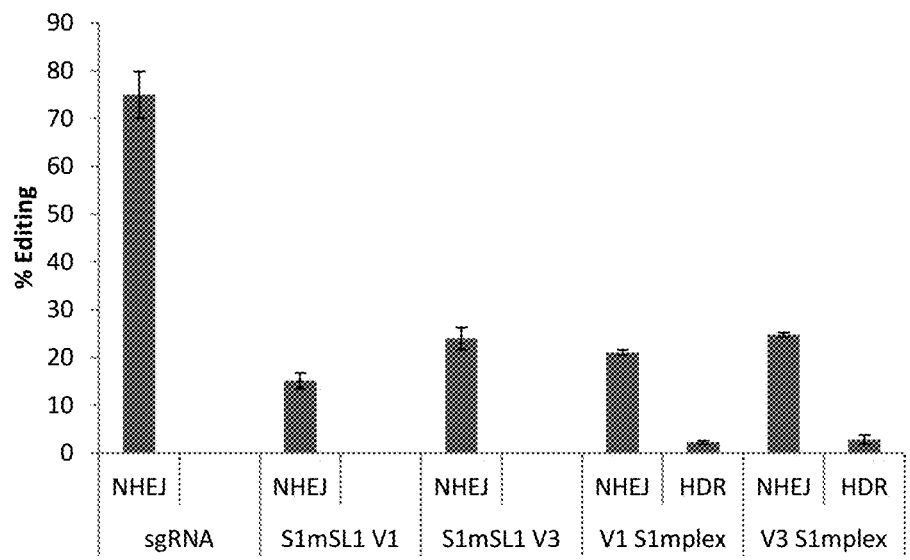
FIG. 37 shows the induction of HDR using various sgRNAs. Cas9 RNPs were formed with standard sgRNA, S1m-sgRNA-1, or S1m-sgRNA-V3 targeting the same locus. S1m-sgRNA-1 and V3 were also used to create S1mplexes containing an ssODN to induce HDR at the target site. S1m-sgRNAs again formed fewer DSBs and S1m-sgRNA-V3 was more efficient at inducing NHEJ than V1. Similarly, when S1mplexes were formed using S1m-sgRNAs, V3 induced higher levels of HDR than V1. However, in this replicate, ratios of HDR:NHEJ differed from what was seen in previous experiments (n=3 technical replicates. Error bars represent ±1 S.D.)

We next tested the capabilities of both S1m-sgRNAs to induce HDR when formed in to an ssODN-S1mplex. S1m-sgRNA-V3 again induced a higher level of HDR when compared to S1m-sgRNA-1 (FIG. 37). However, the ratio of precise to imprecise mutations was decreased in this condition as the level of NHEJ was significantly higher than S1m-sgRNA-1. This suggests that S1m-sgRNA-1 may be a better choice for when only precise mutations are desired within the target cell population.

Both S1m-sgRNA-1 and S1m-sgRNA-V3 have potential to be used in the field of clinical gene editing and may span different applications. S1m-sgRNA-V3 is easier to create and induces higher levels of overall editing, a feature that may be useful in ex vivo therapies. Due to the higher cutting efficiency of S1m-sgRNA-V3, one could also envision a strategy of large deletions by tethering together two RNPs at a defined length. S1m-sgRNA-1 in comparison is a longer aptamer and may feature more utility for attachment of larger cargoes such as qDots or growth factors. It generally has a lower level of overall editing efficiency for both HDR and NHEJ applications but may be more useful for in vivo editing where precise mutations are desired.

Example 10: Isolation of Biallelic Corrected iPSCs

Figure 38:
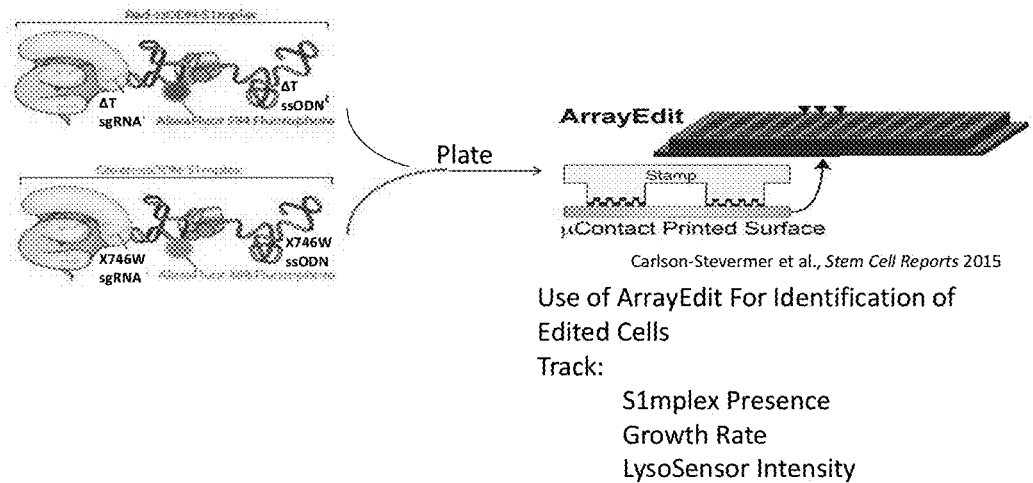
FIG. 38 shows identification of corrected Pompe iPSCs using ArrayEdit platform following transfection with fluorescent S1mplexes. Array Edit enables tracking of phenotypic characteristics.
Figure 39:
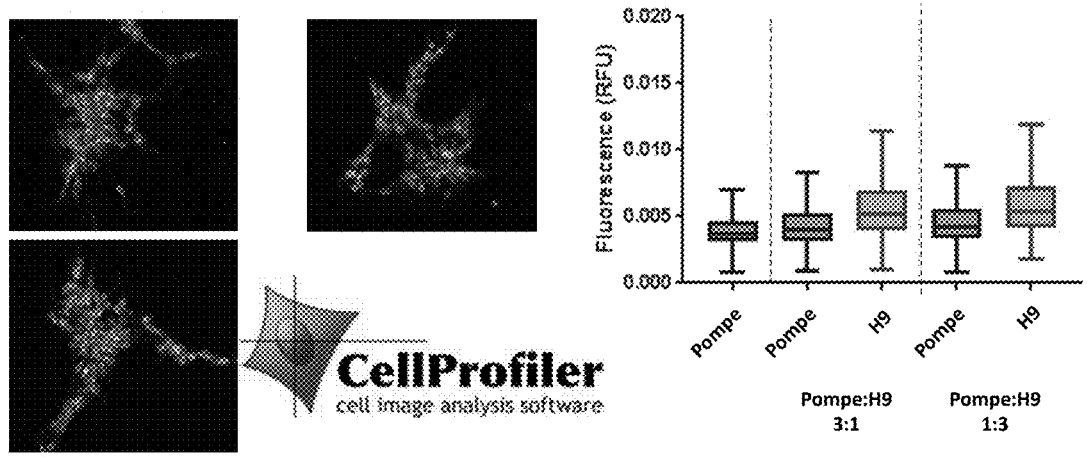
FIG. 39 shows the phenotypic difference between wild-type and Pompe disease iPSCs. Cell lines were cocultured together at the indicated ratio and evaluated for the presence of mCherry (wildtype) or DAPI (disease). Lysosome acidity was measured using LysoSensor™ Green and quantified on a per-cell basis.

We obtained an iPSC line derived from a patient afflicted with infantile-onset Pompe disease. This cell line contains two distinct deleterious mutations at different points within a single gene. We created two fluorescent S1mplex-ssODNs containing sgRNA (Table 8) and ssODNs specific to each diseased locus and transfected them into cells prior to plating on our ArrayEdit platform (FIG. 38). ArrayEdit functions by looking for phenotypic differences between cell colonies to enrich the proportion of selected clones that are edited. We identified lysosome acidity as a potential difference between healthy and diseased cell lines that can be analyzed using image cytometry. To test this hypothesis we co-cultured WA09-H2b-mCherry expressing cells with diseased Pompe iPSCs and stained the lysosomes with LysoSensor™ Green. LysosSensor™ Green is a dye that is preferentially trafficked to acidic organelles and fluoresces at higher intensity at lower pH. We then analyzed the green intensity of each cell within the colculture using CellProfiler and found that there was a significant difference between the two populations, even when growing within the same colony (FIG. 39).

Figure 40:
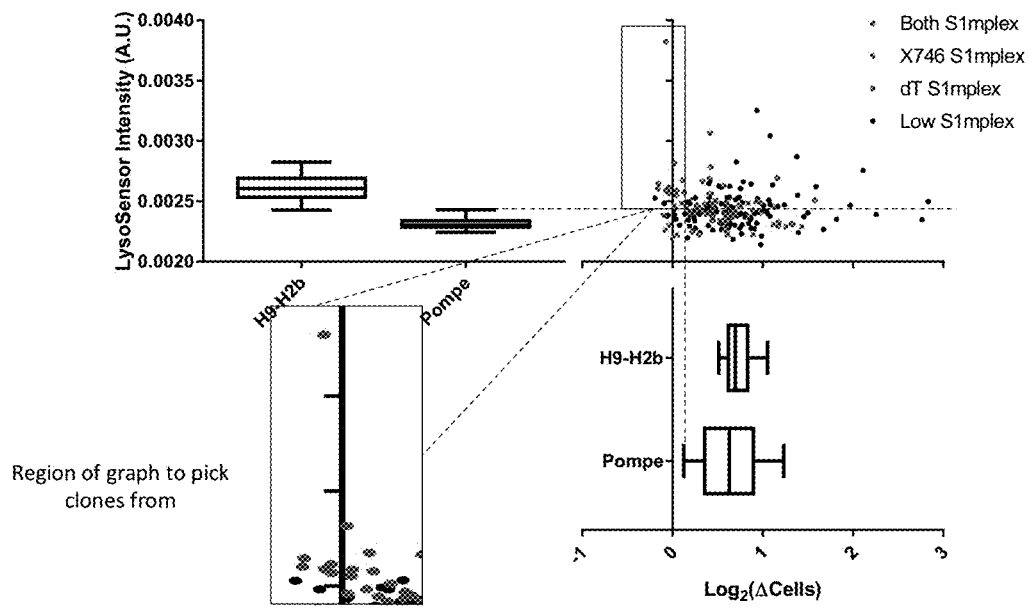
FIG. 40 shows identification of corrected Pompe iPSCs. Pompe iPSCs and H9-H2b-mCherry cells were mock transfected and plated of ArrayEdit platform. Over seven days number of cells per feature was tracked and used to calculate average growth rate (bottom right). On day seven, wells were stained with LysoSensor™ Green and per cell intensity was measured (top left). Data was plotted as a per-feature average. Pompe iPSCs were transfected with S1mplex-ssODNs targeting diseased loci and analyzed in the same manner as described above but with the addition of S1mplex presence on day 1. Clones to be selected (bottom left) were determined by gating out the lowest average growth rate of mock transfected cells as well as the upper intensity limit of mock transfected Pompe iPSCs. Microfeatures with cells meeting both of these criteria as well as displaying S1mplex presence were selected and expanded.
Figure 41:
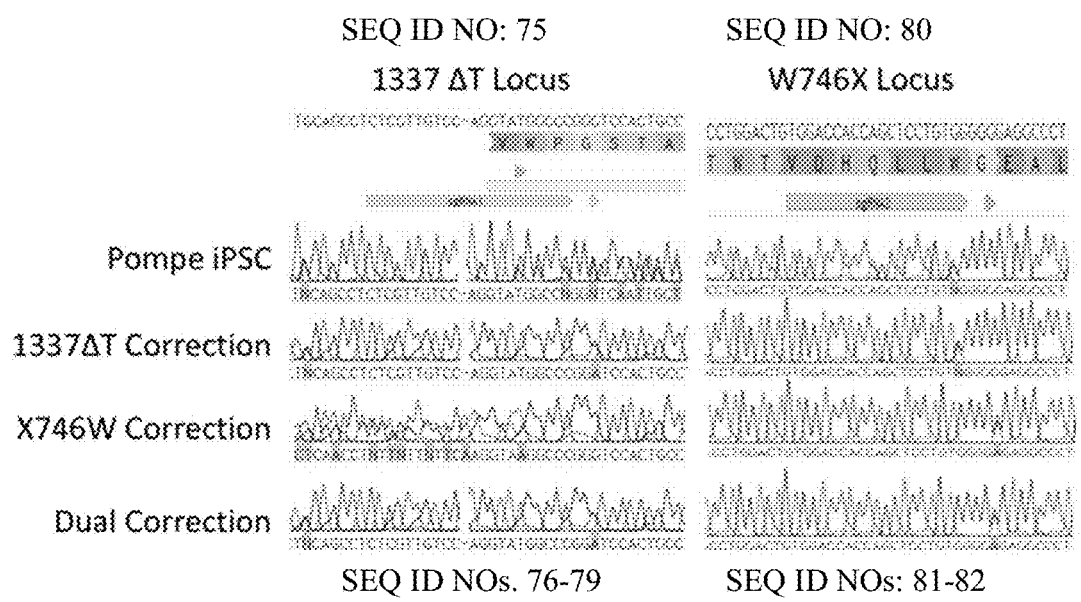
FIG. 41 shows selection of gene-corrected disease iPSCs. Sanger sequencing traces of corrected cell lines. Heterozygous mutations within the PAM sequence show that the ssODN was used as the HDR template in all lines.

With this knowledge we mock transfected WA09 and Pompe PSCs and plated them on ArrayEdit to obtain baseline phenotypic data. We simultaneously transfected Pompe iPSCs with both fluorescent S1mplex-ssODNs. Across all conditions we tracked the growth rate of colonies and seven days post-transfection the LysoSensor™ intensity. We also measured the presence of each S1mplex in the corresponding condition. We again found that the WA09 cell colonies had a significantly higher LysoSensor™ intensity than Pompe iPSCs. Importantly, we also observed Pompe iPSC colonies that displayed intensities similar to that of the control WA09 line, suggesting editing events (FIG. 40). In previous experiments we observed that edited cell colonies may suffer a decrease in fitness while editing events occurred. Accordingly, we tracked cell number of each colony over from day 1-7 of the experiment and plotted the average change in cell number over this time course. We again observed cell colonies that grew slower than mock transfected Pompe iPSCs. Importantly, there were numerous cell colonies that fit all of the criteria for selection for downstream analysis. These were: low growth rate, high Lysosensor™ intensity, and presence of at least one S1mplex type. After selection and Sanger sequencing we observed that we had obtained clones that were positive for correction at both loci individually, and most importantly one clones that contained edits at both alleles simultaneously including mutations to the PAM site (SEQ ID NOs. 76-79; 81-84), showing the ssODN that was the used as the donor DNA (SEQ ID NOs. 75 and 80) (FIG. 41).

TGCAGCCTCTCGTTGTCCAGGTATGGCCCGGGTC-CACTGCC SEQ ID NO: 75;
TNCAGCCTCTCGTTGTCCAGGTATGGCCNGGNT-CAATTGCT SEQ ID NO: 76;
TNCAGCCTCTCGTTGTCCAGGTATGGCCCGGATC-CACTGCC SEQ ID NO: 77;
CTCAGACCTNTTNTTNT-CAAGGTAAGGCCCGGGTCCACTGCC SEQ ID NO: 78;
TNCAGCCTCTCGTTGTCCAGGTATGGCCCGGATC-CACTGCC SEQ ID NO: 79;
CCTGGACTGTGGACCACCAGCTCCTGTGGGG-GAGGCCCT SEQ ID NO: 80;
CCTGGACTGTGGACCACCAGCTCCTGTNGGG-GAGGCCCT SEQ ID NO: 81;
CCTGGACTGTGGACCACCAGCTCCTGTGGG-GAGAGGCCCT SEQ ID NO: 82.

Example 11: Dual S1mplexes for the Excision of Genomic DNA

Figure 42:
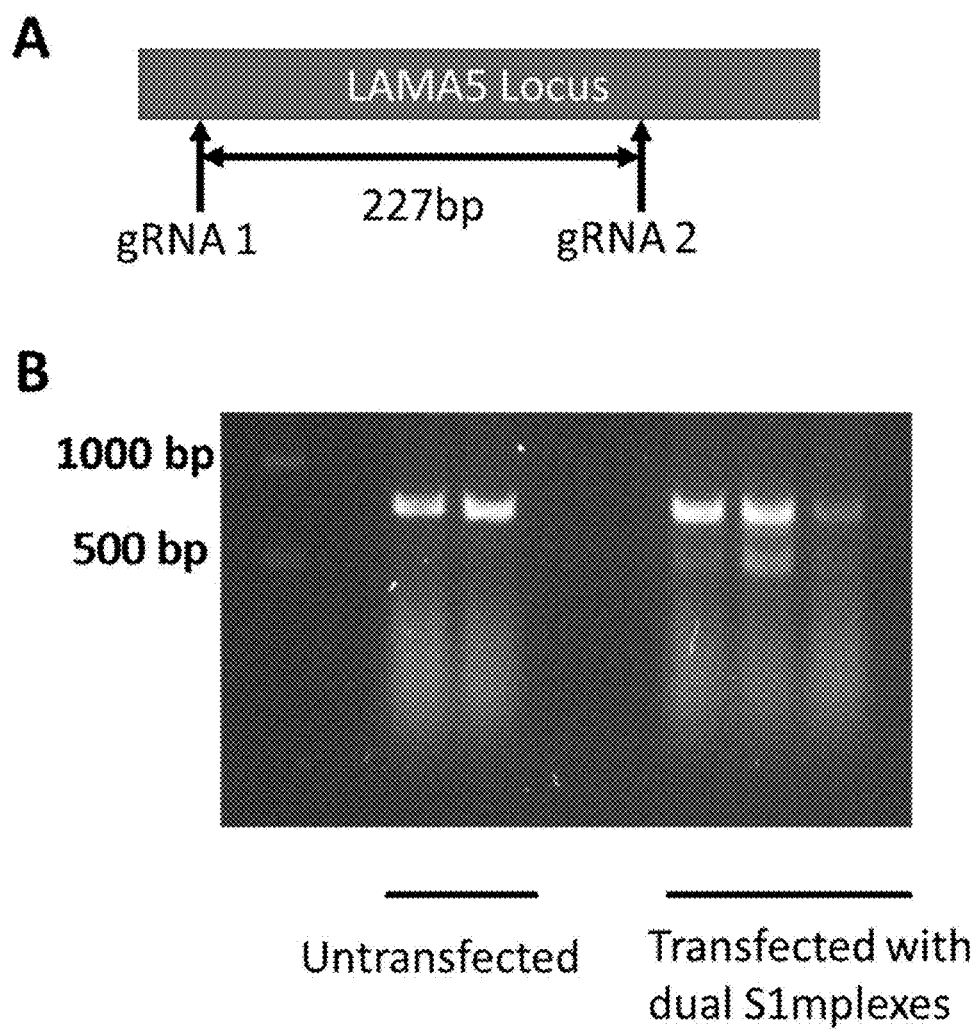
FIG. 42 shows dual S1mplexes for the precise excision of genomic DNA. a) 2 sgRNAs designed in the LAMA5 locus for excision of a 238 bp stretch of genomic DNA. B) Mixed S1m sgRNAs (1,2) with streptavidin added to HEK 293s, with ratio sgRNA:streptavidin 2:1 at 50 ng/well per guide. Gel shows LAMA5 locus PCR amplicon spanning both guides. Average excision efficiency of 22% with dual S1mplexes.

Dual S1mplexes containing S1m-sgRNAs targeted to 2 different spots in the LAMA5 locus were formed (FIG. 42) in order to test whether RNPs targeting 2 positions packaged into S1mplexes and transfected into HEK 293 cells were able to excise the intermediate genomic sequence. After genomic isolation and PCR amplification of the LAMA5, analysis (FIG. 42) showed an average excision efficiency of ~22% of the region spanned by the two sgRNAs in HEK293 cells, demonstrating the utility of dual guided S1mplexes for excision purposes.

To isolate the specific S1mplexes containing only one RNP targeting each site, we will use HPLC (high performance liquid chromatography) to separate out the various S1mplex species formed by random mixing of streptavidin and the various RNPs. We expect to be able to isolate the specific fraction containing one RNP for each of the two sites bound to a single streptavidin. We will compare the excision efficiency of that isolated dual S1mplexes with that of standard double sgRNAs, with and without a donor template for precise excision. For S1mplexes, the donor will be biotinylated and attached to the streptavidin as part of the S1mplex. We expect the simultaneous delivery in a nanoparticle of both RNPs as well as a donor to both increase the efficiency and precision of excision.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A ribonucleoprotein (RNP) complex, comprising
a modified guide RNA comprising,
   a crRNA comprising a single-stranded protospacer sequence and a first complementary strand of a binding region for a Cas9 polypeptide,
   a tracrRNA comprising a second complementary strand of the binding region for the Cas9 polypeptide,
   wherein the crRNA or the tracrRNA comprises a nucleic acid aptamer that binds an avidin,
   wherein the crRNA and the tracrRNA hybridize through the first and second complementary strands of the binding region for the Cas9 polypeptide;
an avidin
the Cas9 polypeptide, wherein the Cas9 polypeptide is active for guide RNA binding, and has an active, inactive or partially inactive nuclease domain, and
a biotinylated molecule.

2. The RNP complex of claim 1, wherein the avidin has one, two or four biotin binding sites, and wherein the avidin optionally comprises a fluorescent label.

3. The RNP complex of claim 1, wherein the biotinylated molecule is a biotinylated donor polynucleotide.

4. The RNP complex of claim 3, wherein the donor polynucleotide comprises single-stranded DNA, double-stranded DNA, RNA, or a duplex of RNA and DNA.

5. The RNP complex of claim 3, wherein the donor polynucleotide includes a mutation, deletion, alteration, integration, gene correction, gene replacement, transgene insertion, nucleotide deletion, gene disruption, and/or gene mutation in a target nucleic acid.

6. The RNP complex of claim 1, wherein the biotinylated molecule comprises a biotinylated nanoparticle, dye, contrast agent, or peptide.

7. The RNP complex of claim 6, wherein the nanoparticle is a quantum dot, a gold particle, a magnetic particle, or a polymeric nanoparticle.

8. The RNP complex of claim 1, wherein the avidin is covalently linked to a donor polynucleotide, either directly or via a linker molecule.

9. The RNP complex of claim 8, wherein the donor polynucleotide comprises single-stranded DNA, double-stranded DNA, RNA, or a duplex of RNA and DNA.

10. The RNP complex of claim 8, wherein the donor polynucleotide includes a mutation, deletion, alteration, integration, gene correction, gene replacement, transgene insertion, nucleotide deletion, gene disruption, and/or gene mutation in a target nucleic acid.

11. The RNP complex of claim 1, wherein the avidin is covalently linked to a nanoparticle, dye molecule, or peptide, either directly or via a linker molecule.

12. A kit comprising
a modified guide RNA, the modified guide RNA comprising,
   a crRNA comprising, a single-stranded protospacer sequence and a first complementary strand of a binding region for a Cas9 polypeptide, and a tracrRNA comprising, a second complementary strand of the binding region for the Cas9 polypeptide,
wherein the crRNA or the tracrRNA comprises a nucleic acid aptamer that binds an avidin,
wherein the crRNA and the tracrRNA hybridize through the first and second complementary strands of the binding region for the Cas9 polypeptide;
an avidin;
a Cas9 polypeptide, and
a biotinylated molecule.

13. A method of modifying a target nucleic acid in a cell, comprising
delivering to the cell an RNP complex, the RNP complex comprising
a modified guide RNA comprising,
a crRNA comprising a single-stranded protospacer sequence and a first complementary strand of a binding region for a Cas9 polypeptide,
a tracrRNA comprising a second complementary strand of the binding region for the Cas9 polypeptide,
wherein the crRNA or the tracrRNA comprises a nucleic acid aptamer that binds an avidin,
wherein the crRNA and the tracrRNA hybridize through the first and second complementary strands of the binding region for the Cas9 polypeptide;
an avidin; and
the Cas9 polypeptide, wherein the Cas9 polypeptide is active for guide RNA binding, and has an active, inactive or partially inactive nuclease domain,
wherein the single-stranded protospacer sequence of the modified guide RNA hybridizes to a sequence in the target nucleic acid to be modified.

14. The method of claim 13, wherein modifying the target nucleic acid increases or decreases expression of a gene product of the target nucleic acid.

15. The method of claim 13, further comprising delivering a donor polynucleotide to the cell, and wherein modifying the target nucleic acid comprises homology-directed repair (HDR).

16. The method of claim 13, further comprising delivering a donor polynucleotide to the cell, and wherein modifying the target nucleic acid comprises addition of a genetically encoded functionality, or correction of a mutation in the target nucleic acid.

17. The method of claim 13, wherein modifying the target nucleic acid creates a double strand break (DSB) which is repaired by a non-homologous end joining (NHEJ) cell repair mechanism generating indels thereby modifying the polynucleotide sequence of the target nucleic acid.

18. The method of claim 13, further comprising delivering a donor polynucleotide to the cell, and wherein modifying the target nucleic acid creates a DSB which is repaired by a HDR cell repair mechanism incorporating a donor DNA sequence thereby modifying the polynucleotide sequence of the target nucleic acid.

19. The method of claim 13, further comprising delivering a biotinylated molecule, wherein the biotinylated molecule targets the RNP complex to a specific cell type, organ or tissue.

20. The method of claim 13, wherein the RNP complex further comprises a biotinylated molecule.

21. The method of claim 20, wherein the biotinylated molecule is a biotinylated donor polynucleotide.

22. The method of claim 21, wherein the donor polynucleotide comprises single-stranded DNA, double-stranded DNA, RNA, or a duplex of RNA and DNA.

23. The method of claim 21, wherein the donor polynucleotide includes a mutation, deletion, alteration, integration, gene correction, gene replacement, transgene insertion, nucleotide deletion, and/or gene disruption.

24. A method of modifying a target nucleic acid in a cell, comprising delivering to the cell two RNP complexes, wherein each RNP complex comprises
a modified guide RNA comprising,
a crRNA comprising a single-stranded protospacer sequence and a first complementary strand of a binding region for a Cas9 polypeptide,
a tracrRNA comprising a second complementary strand of the binding region for the Cas9 polypeptide,
wherein the crRNA or the tracrRNA comprises a nucleic acid aptamer that binds an avidin,
wherein the crRNA and the tracrRNA hybridize through the first and second complementary strands of the binding region for the Cas9 polypeptide;
an avidin; and
a Cas9 polypeptide, wherein the Cas9 polypeptide is active for guide RNA binding, and has an active, inactive or partially inactive nuclease domain,
wherein each of the RNP complexes hybridizes to a different sequence in the target nucleic acid.

25. The method of claim 24, further comprising delivering a donor polynucleotide to the cell, wherein the donor polynucleotide comprises a gene correction relative to the sequence of the target nucleic acid, thereby providing multiple allelic correction of the target nucleic acid, or excision of target DNA from the target nucleic acid.

26. The method of claim 24, further comprising delivering a donor polynucleotide to the cell, wherein the donor polynucleotide comprises a gene correction relative to the sequence of the target nucleic acid, thereby providing multiple allelic correction of the target nucleic acid.

27. The method of claim 24, wherein modifying the target nucleic acid provides excision of genomic DNA.

28. The method of claim 24, wherein each RNP complex further comprises a biotinylated molecule.

29. The method of claim 28, wherein the biotinylated molecules are biotinylated donor polynucleotides.

30. The method of claim 29, wherein the donor polynucleotides comprise single-stranded DNA, double-stranded DNA, RNA, or a duplex of RNA and DNA.

31. The method of claim 29, wherein the donor polynucleotides include a mutation, deletion, alteration, integration, gene correction, gene replacement, transgene insertion, nucleotide deletion, and/or gene disruption.

32. A method of modifying a target nucleic acid in a cell, the cell comprising a Cas9 polypeptide, wherein the Cas9 polypeptide is active for guide RNA binding, and has an active, inactive or partially inactive nuclease domain, the method comprising
delivering to the cell a modified guide RNA, the modified guide RNA comprising,
a crRNA comprising, a single-stranded protospacer sequence and a first complementary strand of a binding region for the Cas9 polypeptide, and
a tracrRNA comprising, a second complementary strand of the binding region for a Cas9 polypeptide,
wherein the crRNA or the tracrRNA comprises a nucleic acid aptamer that binds an avidin,
wherein the crRNA and the tracrRNA hybridize through the first and second complementary strands of the binding region for the Cas9 polypeptide;
wherein the modified guide RNA is associated with an avidin; and wherein the single-stranded protospacer sequence of the modified guide RNA hybridizes to a sequence in the target nucleic acid to be modified.

33. The method of claim 32, wherein two modified guide RNAs are delivered to the cell, and wherein each of the modified guide RNAs hybridizes to a different nucleic acid sequence.

34. The method of claim 32, further comprising delivering a donor polynucleotide to the cell, wherein the donor polynucleotide comprises a gene correction relative to the sequence of the target nucleic acid, thereby providing multiple allelic correction of the target nucleic acid, or excision of target DNA from the target nucleic acid.

35. A method of modifying a target nucleic acid in a cell, comprising
delivering to the cell a vector expressing a modified guide RNA, a vector expressing a Cas9 polypeptide, an avidin, and a biotinylated donor DNA template, the modified guide RNA comprising,
a crRNA comprising, a single-stranded protospacer sequence and a first complementary strand of a binding region for the Cas9 polypeptide, and
a tracrRNA comprising, a second complementary strand of the binding region for the Cas9 polypeptide,
wherein the crRNA or the tracrRNA comprises a nucleic acid aptamer that binds the avidin,
wherein the crRNA and the tracrRNA hybridize through the first and second complementary strands of the binding region for the Cas9 polypeptide,
wherein the single-stranded protospacer sequence of the modified guide RNA hybridizes to a sequence in the target nucleic acid to be modified.

36. The method of claim 35, wherein the cell is a human cell.

37. The method of claim 36, wherein the human cell is a human pluripotent stem cell line, or a primary blood cell.

* * * * *

SEQUENCE LISTING

<160> NUMBER OF SEQ ID NOS: 74

<210> SEQ ID NO 1

-continued

```
<211> LENGTH: 180
<212> TYPE: RNA
<213> ORGANISM: artificial
<220> FEATURE:
<223> OTHER INFORMATION: sgRNA
<220> FEATURE:
<221> NAME/KEY: misc_feature
<222> LOCATION: (1)..(20)
<223> OTHER INFORMATION: n is a, c, g, or u

<400> SEQUENCE: 1
nnnnnnnnnn nnnnnnnnnn guuuaagagc uaugcugcga auacgagaug cggccgccga      60
ccagaaucau gcaagugcgu aagauagucg cggucggcg gcucguauuc gcagcauagc     120
aaguuuaaau aaggcuaguc cguuaucaac uugaaaaagu ggcaccgagu cggugcuuuu     180

<210> SEQ ID NO 2
<211> LENGTH: 190
<212> TYPE: RNA
<213> ORGANISM: artificial
<220> FEATURE:
<223> OTHER INFORMATION: sgRNA
<220> FEATURE:
<221> NAME/KEY: misc_feature
<222> LOCATION: (1)..(20)
<223> OTHER INFORMATION: n is a, c, g, or u

<400> SEQUENCE: 2
nnnnnnnnnn nnnnnnnnnn guuuaagagc uaugcuggaa acagcauagc aaguuuaaau      60
aaggcuaguc cguuaucaac uucgaauacg agaugcggcc gccgaccaga aucaugcaag     120
ugcguaagau agucgcgggu cggcggccgc aucucguauu cggaaaaagu ggcaccgagu     180
cggugcuuuu                                                            190

<210> SEQ ID NO 3
<211> LENGTH: 184
<212> TYPE: RNA
<213> ORGANISM: artificial
<220> FEATURE:
<223> OTHER INFORMATION: sgRNA
<220> FEATURE:
<221> NAME/KEY: misc_feature
<222> LOCATION: (1)..(20)
<223> OTHER INFORMATION: n is a, c, g, or u

<400> SEQUENCE: 3
nnnnnnnnnn nnnnnnnnnn guuuaagagc uaugcuggaa acagcauagc aaguuuaaau      60
aaggcuaguc cguuaucaac uugaaaaagu ggcaccgagu cggugccgaa uacgagaugc     120
ggccgccgac cagaaucaug caagugcgua agauagucgc gggucggcgg cucguauucg     180
uuuu                                                                  184

<210> SEQ ID NO 4
<211> LENGTH: 1368
<212> TYPE: PRT
<213> ORGANISM: Streptococcus pyogenes

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu

```
            465                 470                 475                 480
Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895
```

```
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
Arg Val Ile Leu Ala Asp Ala Asn Leu Asp Lys Val Leu Ser Ala
        1280                1285                1290
```

```
Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

<210> SEQ ID NO 5
<211> LENGTH: 1409
<212> TYPE: PRT
<213> ORGANISM: Streptococcus thermophilus

<400> SEQUENCE: 5

Met Leu Phe Asn Lys Cys Ile Ile Ser Ile Asn Leu Asp Phe Ser
1               5               10              15

Asn Lys Glu Lys Cys Met Thr Lys Pro Tyr Ser Ile Gly Leu Asp Ile
                20              25              30

Gly Thr Asn Ser Val Gly Trp Ala Val Ile Thr Asp Asn Tyr Lys Val
            35              40              45

Pro Ser Lys Lys Met Lys Val Leu Gly Asn Thr Ser Lys Lys Tyr Ile
    50              55              60

Lys Lys Asn Leu Leu Gly Val Leu Leu Phe Ser Gly Ile Thr Ala
65              70              75              80

Glu Gly Arg Arg Leu Lys Arg Thr Ala Arg Arg Tyr Thr Arg Arg
                85              90              95

Arg Asn Arg Ile Leu Tyr Leu Gln Glu Ile Phe Ser Thr Glu Met Ala
                100             105             110

Thr Leu Asp Asp Ala Phe Phe Gln Arg Leu Asp Asp Ser Phe Leu Val
            115             120             125

Pro Asp Asp Lys Arg Asp Ser Lys Tyr Pro Ile Phe Gly Asn Leu Val
    130             135             140

Glu Glu Lys Val Tyr His Asp Glu Phe Pro Thr Ile Tyr His Leu Arg
145             150             155             160

Lys Tyr Leu Ala Asp Ser Thr Lys Lys Ala Asp Leu Arg Leu Val Tyr
                165             170             175

Leu Ala Leu Ala His Met Ile Lys Tyr Arg Gly His Phe Leu Ile Glu
            180             185             190

Gly Glu Phe Asn Ser Lys Asn Asn Asp Ile Gln Lys Asn Phe Gln Asp
    195             200             205

Phe Leu Asp Thr Tyr Asn Ala Ile Phe Glu Ser Asp Leu Ser Leu Glu
    210             215             220

Asn Ser Lys Gln Leu Glu Glu Ile Val Lys Asp Lys Ile Ser Lys Leu
225             230             235             240

Glu Lys Lys Asp Arg Ile Leu Lys Leu Phe Pro Gly Glu Lys Asn Ser
                245             250             255

Gly Ile Phe Ser Glu Phe Leu Lys Leu Ile Val Gly Asn Gln Ala Asp
            260             265             270

Phe Arg Lys Cys Phe Asn Leu Asp Glu Lys Ala Ser Leu His Phe Ser
    275             280             285

Lys Glu Ser Tyr Asp Glu Asp Leu Glu Thr Leu Leu Gly Tyr Ile Gly
    290             295             300
```

```
Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
    370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
        435                 440                 445

Lys Phe Tyr Pro Phe Leu Ala Lys Asn Lys Glu Arg Ile Glu Lys Ile
    450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
        515                 520                 525

Leu Pro Lys His Ser Leu Leu Tyr Glu Thr Phe Asn Val Tyr Asn Glu
    530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590

Tyr Gly Tyr Asp Gly Ile Glu Leu Lys Gly Ile Glu Lys Gln Phe Asn
        595                 600                 605

Ser Ser Leu Ser Thr Tyr His Asp Leu Leu Asn Ile Ile Asn Asp Lys
    610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
            660                 665                 670

Arg Arg His Tyr Thr Gly Trp Gly Lys Leu Ser Ala Lys Leu Ile Asn
        675                 680                 685

Gly Ile Arg Asp Glu Lys Ser Gly Asn Thr Ile Leu Asp Tyr Leu Ile
    690                 695                 700

Asp Asp Gly Ile Ser Asn Arg Asn Phe Met Gln Leu Ile His Asp Asp
705                 710                 715                 720
```

```
Ala Leu Ser Phe Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
            740                 745                 750

Pro Ala Ile Lys Lys Gly Ile Leu Gln Ser Ile Lys Ile Val Asp Glu
            755                 760                 765

Leu Val Lys Val Met Gly Gly Arg Lys Pro Glu Ser Ile Val Val Glu
            770                 775                 780

Met Ala Arg Glu Asn Gln Tyr Thr Asn Gln Gly Lys Ser Asn Ser Gln
785                 790                 795                 800

Gln Arg Leu Lys Arg Leu Glu Lys Ser Leu Lys Glu Leu Gly Ser Lys
                805                 810                 815

Ile Leu Lys Glu Asn Ile Pro Ala Lys Leu Ser Lys Ile Asp Asn Asn
                820                 825                 830

Ala Leu Gln Asn Asp Arg Leu Tyr Leu Tyr Tyr Leu Gln Asn Gly Lys
                835                 840                 845

Asp Met Tyr Thr Gly Asp Asp Leu Asp Ile Asp Arg Leu Ser Asn Tyr
                850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
                900                 905                 910

Gln Leu Leu Lys Ser Lys Leu Ile Ser Gln Arg Lys Phe Asp Asn Leu
                915                 920                 925

Thr Lys Ala Glu Arg Gly Gly Leu Leu Pro Glu Asp Lys Ala Gly Phe
                930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Asn Arg
                965                 970                 975

Ala Val Arg Thr Val Lys Ile Ile Thr Leu Lys Ser Thr Leu Val Ser
                980                 985                 990

Gln Phe Arg Lys Asp Phe Glu Leu Tyr Lys Val Arg Glu Ile Asn Asp
                995                 1000                1005

Phe His His Ala His Asp Ala Tyr Leu Asn Ala Val Ile Ala Ser
                1010                1015                1020

Ala Leu Leu Lys Lys Tyr Pro Lys Leu Glu Pro Glu Phe Val Tyr
                1025                1030                1035

Gly Asp Tyr Pro Lys Tyr Asn Ser Phe Arg Glu Arg Lys Ser Ala
                1040                1045                1050

Thr Glu Lys Val Tyr Phe Tyr Ser Asn Ile Met Asn Ile Phe Lys
                1055                1060                1065

Lys Ser Ile Ser Leu Ala Asp Gly Arg Val Ile Glu Arg Pro Leu
                1070                1075                1080

Ile Glu Val Asn Glu Glu Thr Gly Glu Ser Val Trp Asn Lys Glu
                1085                1090                1095

Ser Asp Leu Ala Thr Val Arg Arg Val Leu Ser Tyr Pro Gln Val
                1100                1105                1110

Asn Val Val Lys Lys Val Glu Glu Gln Asn His Gly Leu Asp Arg
                1115                1120                1125

Gly Lys Pro Lys Gly Leu Phe Asn Ala Asn Leu Ser Ser Lys Pro
```

```
            1130                1135               1140
Lys Pro Asn Ser Asn Glu Asn Leu Val Gly Ala Lys Glu Tyr Leu
    1145                1150               1155
Asp Pro Lys Lys Tyr Gly Gly Tyr Ala Gly Ile Ser Asn Ser Phe
            1160                1165               1170
Ala Val Leu Val Lys Gly Thr Ile Glu Lys Gly Ala Lys Lys Lys
    1175                1180               1185
Ile Thr Asn Val Leu Glu Phe Gln Gly Ile Ser Ile Leu Asp Arg
            1190                1195               1200
Ile Asn Tyr Arg Lys Asp Lys Leu Asn Phe Leu Leu Glu Lys Gly
    1205                1210               1215
Tyr Lys Asp Ile Glu Leu Ile Ile Glu Leu Pro Lys Tyr Ser Leu
            1220                1225               1230
Phe Glu Leu Ser Asp Gly Ser Arg Arg Met Leu Ala Ser Ile Leu
    1235                1240               1245
Ser Thr Asn Asn Lys Arg Gly Glu Ile His Lys Gly Asn Gln Ile
            1250                1255               1260
Phe Leu Ser Gln Lys Phe Val Lys Leu Leu Tyr His Ala Lys Arg
    1265                1270               1275
Ile Ser Asn Thr Ile Asn Glu Asn His Arg Lys Tyr Val Glu Asn
            1280                1285               1290
His Lys Lys Glu Phe Glu Glu Leu Phe Tyr Tyr Ile Leu Glu Phe
    1295                1300               1305
Asn Glu Asn Tyr Val Gly Ala Lys Lys Asn Gly Lys Leu Leu Asn
            1310                1315               1320
Ser Ala Phe Gln Ser Trp Gln Asn His Ser Ile Asp Glu Leu Cys
    1325                1330               1335
Ser Ser Phe Ile Gly Pro Thr Gly Ser Glu Arg Lys Gly Leu Phe
            1340                1345               1350
Glu Leu Thr Ser Arg Gly Ser Ala Ala Asp Phe Glu Phe Leu Gly
    1355                1360               1365
Val Lys Ile Pro Arg Tyr Arg Asp Tyr Thr Pro Ser Ser Leu Leu
            1370                1375               1380
Lys Asp Ala Thr Leu Ile His Gln Ser Val Thr Gly Leu Tyr Glu
    1385                1390               1395
Thr Arg Ile Asp Leu Ala Lys Leu Gly Glu Gly
            1400                1405

<210> SEQ ID NO 6
<211> LENGTH: 1082
<212> TYPE: PRT
<213> ORGANISM: Neisseria

<400> SEQUENCE: 6

Met Ala Ala Phe Lys Pro Asn Pro Ile Asn Tyr Ile Leu Gly Leu Asp
1               5                   10                  15
Ile Gly Ile Ala Ser Val Gly Trp Ala Met Val Glu Ile Asp Glu Glu
                20                  25                  30
Glu Asn Pro Ile Arg Leu Ile Asp Leu Gly Val Arg Val Phe Glu Arg
        35                  40                  45
Ala Glu Val Pro Lys Thr Gly Asp Ser Leu Ala Met Val Arg Arg Leu
    50                  55                  60
Ala Arg Ser Val Arg Arg Leu Thr Arg Arg Arg Ala His Arg Leu Leu
65                  70                  75                  80
```

-continued

```
Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Ile Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
```

```
              500                 505                 510
Phe Lys Asp Arg Lys Glu Ile Glu Lys Arg Gln Glu Glu Asn Arg Lys
            515                 520                 525

Asp Arg Glu Lys Ala Ala Lys Phe Arg Glu Tyr Phe Pro Asn Phe
            530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
                580                 585                 590

Ser Arg Thr Trp Asp Asp Ser Phe Asn Asn Lys Val Leu Val Leu Gly
                595                 600                 605

Ser Glu Asn Gln Asn Lys Gly Asn Gln Thr Pro Tyr Glu Tyr Phe Asn
                610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
                660                 665                 670

Val Asn Arg Phe Leu Cys Gln Phe Val Ala Asp Arg Met Arg Leu Thr
                675                 680                 685

Gly Lys Gly Lys Lys Arg Val Phe Ala Ser Asn Gly Gln Ile Thr Asn
                690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
                740                 745                 750

Phe Asp Gly Lys Thr Ile Asp Lys Glu Thr Gly Glu Val Leu His Gln
                755                 760                 765

Lys Thr His Phe Pro Gln Pro Trp Glu Phe Phe Ala Gln Glu Val Met
                770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
                835                 840                 845

Ser Ala Lys Arg Leu Asp Glu Gly Val Ser Val Leu Arg Val Pro Leu
                850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
                900                 905                 910

Ala Gly Asn Arg Thr Gln Gln Val Lys Ala Val Arg Val Glu Gln Val
                915                 920                 925
```

```
Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
            965                 970                 975

Arg Ala Val Val Gln Gly Lys Asp Glu Glu Asp Trp Gln Leu Ile Asp
                980                 985                 990

Asp Ser Phe Asn Phe Lys Phe Ser Leu His Pro Asn Asp Leu Val Glu
            995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 7
<211> LENGTH: 1395
<212> TYPE: PRT
<213> ORGANISM: Treponema

<400> SEQUENCE: 7

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
                20                  25                  30

Ala Asn Arg Lys Asp Leu Trp Gly Met Arg Cys Phe Glu Thr Ala Glu
            35                  40                  45

Thr Ala Glu Val Arg Arg Leu His Arg Gly Ala Arg Arg Ile Glu
50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
```

-continued

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
            245                 250                 255

Glu Lys Asn Ser Ile Ser Phe Ser Lys Asp Asp Phe Asp Ala Leu Ser
                260                 265                 270

Asp Asp Leu Ala Ser Ile Leu Gly Asp Ser Phe Glu Leu Leu Leu Lys
            275                 280                 285

Ala Lys Ala Val Tyr Asn Cys Ser Val Leu Ser Lys Val Ile Gly Asp
        290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
        370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
            485                 490                 495

Thr Thr Pro Trp Asn Phe Phe Asp His Ile Asp Lys Glu Lys Thr Ala
                500                 505                 510

Glu Ala Phe Ile Thr Ser Arg Thr Asn Phe Cys Thr Tyr Leu Val Gly
            515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Ile Asp Gly Lys Asn Ile
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
        595                 600                 605

Glu Cys Thr Ser Ser Leu Lys Ser Tyr Ile Glu Leu Lys Asn Ile Phe
    610                 615                 620

Gly Lys Gln Val Asp Glu Ile Ser Thr Lys Asn Met Leu Glu Glu Ile
625                 630                 635                 640

```
Ile Arg Trp Ala Thr Ile Tyr Asp Glu Gly Glu Gly Lys Thr Ile Leu
                645                 650                 655
Lys Thr Lys Ile Lys Ala Glu Tyr Gly Lys Tyr Cys Ser Asp Glu Gln
                660                 665                 670
Ile Lys Lys Ile Leu Asn Leu Lys Phe Ser Gly Trp Gly Arg Leu Ser
                675                 680                 685
Arg Lys Phe Leu Glu Thr Val Thr Ser Glu Met Pro Gly Phe Ser Glu
            690                 695                 700
Pro Val Asn Ile Ile Thr Ala Met Arg Glu Thr Gln Asn Asn Leu Met
705                 710                 715                 720
Glu Leu Leu Ser Ser Glu Phe Thr Phe Thr Glu Asn Ile Lys Lys Ile
                725                 730                 735
Asn Ser Gly Phe Glu Asp Ala Glu Lys Gln Phe Ser Tyr Asp Gly Leu
                740                 745                 750
Val Lys Pro Leu Phe Leu Ser Pro Ser Val Lys Lys Met Leu Trp Gln
                755                 760                 765
Thr Leu Lys Leu Val Lys Glu Ile Ser His Ile Thr Gln Ala Pro Pro
770                 775                 780
Lys Lys Ile Phe Ile Glu Met Ala Lys Gly Ala Glu Leu Glu Pro Ala
785                 790                 795                 800
Arg Thr Lys Thr Arg Leu Lys Ile Leu Gln Asp Leu Tyr Asn Asn Cys
                805                 810                 815
Lys Asn Asp Ala Asp Ala Phe Ser Ser Glu Ile Lys Asp Leu Ser Gly
                820                 825                 830
Lys Ile Glu Asn Glu Asp Asn Leu Arg Leu Arg Ser Asp Lys Leu Tyr
                835                 840                 845
Leu Tyr Tyr Thr Gln Leu Gly Lys Cys Met Tyr Cys Gly Lys Pro Ile
                850                 855                 860
Glu Ile Gly His Val Phe Asp Thr Ser Asn Tyr Asp Ile Asp His Ile
865                 870                 875                 880
Tyr Pro Gln Ser Lys Ile Lys Asp Asp Ser Ile Ser Asn Arg Val Leu
                885                 890                 895
Val Cys Ser Ser Cys Asn Lys Asn Lys Glu Asp Lys Tyr Pro Leu Lys
                900                 905                 910
Ser Glu Ile Gln Ser Lys Gln Arg Gly Phe Trp Asn Phe Leu Gln Arg
                915                 920                 925
Asn Asn Phe Ile Ser Leu Glu Lys Leu Asn Arg Leu Thr Arg Ala Thr
            930                 935                 940
Pro Ile Ser Asp Asp Glu Thr Ala Lys Phe Ile Ala Arg Gln Leu Val
945                 950                 955                 960
Glu Thr Arg Gln Ala Thr Lys Val Ala Ala Lys Val Leu Glu Lys Met
                965                 970                 975
Phe Pro Glu Thr Lys Ile Val Tyr Ser Lys Ala Glu Thr Val Ser Met
                980                 985                 990
Phe Arg Asn Lys Phe Asp Ile Val Lys Cys Arg Glu Ile Asn Asp Phe
                995                 1000                1005
His His Ala His Asp Ala Tyr Leu Asn Ile Val Val Gly Asn Val
        1010                1015                1020
Tyr Asn Thr Lys Phe Thr Asn Asn Pro Trp Asn Phe Ile Lys Glu
        1025                1030                1035
Lys Arg Asp Asn Pro Lys Ile Ala Asp Thr Tyr Asn Tyr Tyr Lys
        1040                1045                1050
```

-continued

```
Val Phe Asp Tyr Asp Val Lys Arg Asn Asn Ile Thr Ala Trp Glu
    1055                1060                1065

Lys Gly Lys Thr Ile Ile Thr Val Lys Asp Met Leu Lys Arg Asn
    1070                1075                1080

Thr Pro Ile Tyr Thr Arg Gln Ala Ala Cys Lys Lys Gly Glu Leu
    1085                1090                1095

Phe Asn Gln Thr Ile Met Lys Lys Gly Leu Gly Gln His Pro Leu
    1100                1105                1110

Lys Lys Glu Gly Pro Phe Ser Asn Ile Ser Lys Tyr Gly Gly Tyr
    1115                1120                1125

Asn Lys Val Ser Ala Ala Tyr Tyr Thr Leu Ile Glu Tyr Glu Glu
    1130                1135                1140

Lys Gly Asn Lys Ile Arg Ser Leu Glu Thr Ile Pro Leu Tyr Leu
    1145                1150                1155

Val Lys Asp Ile Gln Lys Asp Gln Asp Val Leu Lys Ser Tyr Leu
    1160                1165                1170

Thr Asp Leu Leu Gly Lys Lys Glu Phe Lys Ile Leu Val Pro Lys
    1175                1180                1185

Ile Lys Ile Asn Ser Leu Leu Lys Ile Asn Gly Phe Pro Cys His
    1190                1195                1200

Ile Thr Gly Lys Thr Asn Asp Ser Phe Leu Leu Arg Pro Ala Val
    1205                1210                1215

Gln Phe Cys Cys Ser Asn Asn Glu Val Leu Tyr Phe Lys Lys Ile
    1220                1225                1230

Ile Arg Phe Ser Glu Ile Arg Ser Gln Arg Glu Lys Ile Gly Lys
    1235                1240                1245

Thr Ile Ser Pro Tyr Glu Asp Leu Ser Phe Arg Ser Tyr Ile Lys
    1250                1255                1260

Glu Asn Leu Trp Lys Lys Thr Lys Asn Asp Glu Ile Gly Glu Lys
    1265                1270                1275

Glu Phe Tyr Asp Leu Leu Gln Lys Lys Asn Leu Glu Ile Tyr Asp
    1280                1285                1290

Met Leu Leu Thr Lys His Lys Asp Thr Ile Tyr Lys Lys Arg Pro
    1295                1300                1305

Asn Ser Ala Thr Ile Asp Ile Leu Val Lys Gly Lys Glu Lys Phe
    1310                1315                1320

Lys Ser Leu Ile Ile Glu Asn Gln Phe Glu Val Ile Leu Glu Ile
    1325                1330                1335

Leu Lys Leu Phe Ser Ala Thr Arg Asn Val Ser Asp Leu Gln His
    1340                1345                1350

Ile Gly Gly Ser Lys Tyr Ser Gly Val Ala Lys Ile Gly Asn Lys
    1355                1360                1365

Ile Ser Ser Leu Asp Asn Cys Ile Leu Ile Tyr Gln Ser Ile Thr
    1370                1375                1380

Gly Ile Phe Glu Lys Arg Ile Asp Leu Leu Lys Val
    1385                1390                1395
```

<210> SEQ ID NO 8
<211> LENGTH: 90
<212> TYPE: DNA
<213> ORGANISM: artificial
<220> FEATURE:
<223> OTHER INFORMATION: primer

<400> SEQUENCE: 8

```
gtttaagagc tatgctgcga atacgagatg cggccgccga ccagaatcat gcaagtgcgt    60
aagatagtcg cgggtcggcg gctcgtattc                                     90
```

<210> SEQ ID NO 9
<211> LENGTH: 90
<212> TYPE: DNA
<213> ORGANISM: artificial
<220> FEATURE:
<223> OTHER INFORMATION: primer

<400> SEQUENCE: 9

```
aaaagcaccg actcggtgcc acttttcaa gttgataacg gactagcctt atttaaactt    60
gctatgctgc gaatacgagc cgccgacccg                                     90
```

<210> SEQ ID NO 10
<211> LENGTH: 60
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (21)..(40)
<223> OTHER INFORMATION: n is a, c, g, or t

<400> SEQUENCE: 10

```
ttaatacgac tcactatagg nnnnnnnnnn nnnnnnnnnn gtttaagagc tatgctgcga    60
```

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11

```
aaaagcaccg actcggtgcc                                                20
```

<210> SEQ ID NO 12
<211> LENGTH: 20
<212> TYPE: DNA
<213> ORGANISM: artificial
<220> FEATURE:
<223> OTHER INFORMATION: protospacer

<400> SEQUENCE: 12

```
gctgaagcac tgcacgccat                                                20
```

<210> SEQ ID NO 13
<211> LENGTH: 20
<212> TYPE: DNA
<213> ORGANISM: artificial
<220> FEATURE:
<223> OTHER INFORMATION: protospacer

<400> SEQUENCE: 13

```
gtcacctcca atgactaggg                                                20
```

<210> SEQ ID NO 14
<211> LENGTH: 20
<212> TYPE: DNA
<213> ORGANISM: artificial
<220> FEATURE:
<223> OTHER INFORMATION: protospacer

<400> SEQUENCE: 14

```
ggagccgtac atgaactgag                                               20

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
ccatcccctt ctgtgaatgt                                               20

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
ggagattgga gacacggaga                                               20

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
tccaccttgg cttggctttg                                               20

<210> SEQ ID NO 18
<211> LENGTH: 19
<212> TYPE: DNA
<213> ORGANISM: artificial
<220> FEATURE:
<223> OTHER INFORMATION: primer

<400> SEQUENCE: 18
ccctccacca gtaccccac                                                19

<210> SEQ ID NO 19
<211> LENGTH: 22
<212> TYPE: DNA
<213> ORGANISM: artificial
<220> FEATURE:
<223> OTHER INFORMATION: primer

<400> SEQUENCE: 19
aagggcgagg aggataacat gg                                            22

<210> SEQ ID NO 20
<211> LENGTH: 21
<212> TYPE: DNA
<213> ORGANISM: artificial
<220> FEATURE:
<223> OTHER INFORMATION: primer

<400> SEQUENCE: 20
ttgtacagct cgtccatgcc g                                             21

<210> SEQ ID NO 21
<211> LENGTH: 20
<212> TYPE: DNA
```

```
<213> ORGANISM: artificial
<220> FEATURE:
<223> OTHER INFORMATION: primer

<400> SEQUENCE: 21
ccaatgacaa gcttgctagc                                                     20

<210> SEQ ID NO 22
<211> LENGTH: 100
<212> TYPE: DNA
<213> ORGANISM: artificial
<220> FEATURE:
<223> OTHER INFORMATION: ssODN

<400> SEQUENCE: 22
tcatgtggtc ggggtagcgg ctgaagcact gcacgccatg ggtcagggtg gtcacgaggg         60
tgggccaggg caccggcagc ttgccggtgg tgcagatgaa                               100

<210> SEQ ID NO 23
<211> LENGTH: 100
<212> TYPE: DNA
<213> ORGANISM: artificial
<220> FEATURE:
<223> OTHER INFORMATION: ssODN

<400> SEQUENCE: 23
tcatgtggtc ggggtagcgg ctgaagcact gcacgccatg ggtcagggtg gtcacgaggg         60
tgggccaggg caccggcagc ttgccggtgg tgcagatgaa                               100

<210> SEQ ID NO 24
<211> LENGTH: 90
<212> TYPE: DNA
<213> ORGANISM: artificial
<220> FEATURE:
<223> OTHER INFORMATION: ssODN

<400> SEQUENCE: 24
aagcagcact ctgccctcgt gggtttgtgg ttgcccaccg ctagcaagct tgtcattgga         60
ggtgacatcg atgtcctccc cattggcctg                                          90

<210> SEQ ID NO 25
<211> LENGTH: 90
<212> TYPE: DNA
<213> ORGANISM: Artificial Sequence
<220> FEATURE:
<223> OTHER INFORMATION: ssODN

<400> SEQUENCE: 25
aagcagcact ctgccctcgt gggtttgtgg ttgcccaccg ctagcaagct tgtcattgga         60
ggtgacatcg atgtcctccc cattggcctg                                          90

<210> SEQ ID NO 26
<211> LENGTH: 20
<212> TYPE: DNA
<213> ORGANISM: artificial
<220> FEATURE:
<223> OTHER INFORMATION: Off-target sequence

<400> SEQUENCE: 26
gctgaagcac tgcacgccat                                                     20

<210> SEQ ID NO 27
<211> LENGTH: 20
```

```
<212> TYPE: DNA
<213> ORGANISM: artificial
<220> FEATURE:
<223> OTHER INFORMATION: Off-target sequence

<400> SEQUENCE: 27
gcagaagcac tgcaagccat                                                 20

<210> SEQ ID NO 28
<211> LENGTH: 20
<212> TYPE: DNA
<213> ORGANISM: artificial
<220> FEATURE:
<223> OTHER INFORMATION: Off-target sequence

<400> SEQUENCE: 28
tctgaagtgc tgcacgccat                                                 20

<210> SEQ ID NO 29
<211> LENGTH: 20
<212> TYPE: DNA
<213> ORGANISM: artificial
<220> FEATURE:
<223> OTHER INFORMATION: Off-target sequence

<400> SEQUENCE: 29
gtggaagcac tgcaagccat                                                 20

<210> SEQ ID NO 30
<211> LENGTH: 20
<212> TYPE: DNA
<213> ORGANISM: artificial
<220> FEATURE:
<223> OTHER INFORMATION: Off-target sequence

<400> SEQUENCE: 30
ggtggagcag ggcacgccat                                                 20

<210> SEQ ID NO 31
<211> LENGTH: 20
<212> TYPE: DNA
<213> ORGANISM: artificial
<220> FEATURE:
<223> OTHER INFORMATION: Off-target sequence

<400> SEQUENCE: 31
gaagaagcac tgcaccccat                                                 20

<210> SEQ ID NO 32
<211> LENGTH: 20
<212> TYPE: DNA
<213> ORGANISM: artificial
<220> FEATURE:
<223> OTHER INFORMATION: Off-target sequence

<400> SEQUENCE: 32
gtcacctcca atgactaggg                                                 20

<210> SEQ ID NO 33
<211> LENGTH: 20
<212> TYPE: DNA
<213> ORGANISM: artificial
<220> FEATURE:
<223> OTHER INFORMATION: Off-target sequence

<400> SEQUENCE: 33
```
aggaccacca atgactaggg                                                        20

<210> SEQ ID NO 34
<211> LENGTH: 20
<212> TYPE: DNA
<213> ORGANISM: artificial
<220> FEATURE:
<223> OTHER INFORMATION: Off-target sequence

<400> SEQUENCE: 34
accacctgta atgactaggg                                                        20

<210> SEQ ID NO 35
<211> LENGTH: 20
<212> TYPE: DNA
<213> ORGANISM: artificial
<220> FEATURE:
<223> OTHER INFORMATION: Off-target sequence

<400> SEQUENCE: 35
ggagcctcca gtgactaggg                                                        20

<210> SEQ ID NO 36
<211> LENGTH: 20
<212> TYPE: DNA
<213> ORGANISM: artificial
<220> FEATURE:
<223> OTHER INFORMATION: Off-target sequence

<400> SEQUENCE: 36
gtgaactaca gtgactaggg                                                        20

<210> SEQ ID NO 37
<211> LENGTH: 20
<212> TYPE: DNA
<213> ORGANISM: artificial
<220> FEATURE:
<223> OTHER INFORMATION: Off-target sequence

<400> SEQUENCE: 37
ctggcctcca aagactaggg                                                        20

<210> SEQ ID NO 38
<211> LENGTH: 22
<212> TYPE: DNA
<213> ORGANISM: artificial
<220> FEATURE:
<223> OTHER INFORMATION: primer

<400> SEQUENCE: 38
tttcctagca agcagactca ga                                                     22

<210> SEQ ID NO 39
<211> LENGTH: 21
<212> TYPE: DNA
<213> ORGANISM: artificial
<220> FEATURE:
<223> OTHER INFORMATION: primer

<400> SEQUENCE: 39
agctgtcctt tgtcccattg a                                                      21

<210> SEQ ID NO 40
<211> LENGTH: 21
<212> TYPE: DNA
<213> ORGANISM: artificial

```
<220> FEATURE:
<223> OTHER INFORMATION: primer

<400> SEQUENCE: 40
tctccatgcc ctcctttcca t                                              21

<210> SEQ ID NO 41
<211> LENGTH: 23
<212> TYPE: DNA
<213> ORGANISM: artificial
<220> FEATURE:
<223> OTHER INFORMATION: primer

<400> SEQUENCE: 41
ggatgtagtc catgatcttc ccc                                            23

<210> SEQ ID NO 42
<211> LENGTH: 22
<212> TYPE: DNA
<213> ORGANISM: artificial
<220> FEATURE:
<223> OTHER INFORMATION: primer

<400> SEQUENCE: 42
tcccagaatg tgaaagtgga gg                                             22

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
ctgtgggctt tcctcagctc                                                20

<210> SEQ ID NO 44
<211> LENGTH: 20
<212> TYPE: DNA
<213> ORGANISM: artificial
<220> FEATURE:
<223> OTHER INFORMATION: primer

<400> SEQUENCE: 44
gctgactaac gtccactgct                                                20

<210> SEQ ID NO 45
<211> LENGTH: 24
<212> TYPE: DNA
<213> ORGANISM: artificial
<220> FEATURE:
<223> OTHER INFORMATION: primer

<400> SEQUENCE: 45
tggacctatg tttttcttcg tcac                                           24

<210> SEQ ID NO 46
<211> LENGTH: 21
<212> TYPE: DNA
<213> ORGANISM: artificial
<220> FEATURE:
<223> OTHER INFORMATION: primer

<400> SEQUENCE: 46
aaagtctgtg gccttgtgag a                                              21
```

```
<210> SEQ ID NO 47
<211> LENGTH: 20
<212> TYPE: DNA
<213> ORGANISM: artificial
<220> FEATURE:
<223> OTHER INFORMATION: primer

<400> SEQUENCE: 47
aaccctaccc cctacctgaa                                               20

<210> SEQ ID NO 48
<211> LENGTH: 21
<212> TYPE: DNA
<213> ORGANISM: artificial
<220> FEATURE:
<223> OTHER INFORMATION: primer

<400> SEQUENCE: 48
ttccccaggt agttgctgtt c                                             21

<210> SEQ ID NO 49
<211> LENGTH: 21
<212> TYPE: DNA
<213> ORGANISM: artificial
<220> FEATURE:
<223> OTHER INFORMATION: primer

<400> SEQUENCE: 49
tctgcacatg tcccaactgt c                                             21

<210> SEQ ID NO 50
<211> LENGTH: 21
<212> TYPE: DNA
<213> ORGANISM: artificial
<220> FEATURE:
<223> OTHER INFORMATION: primer

<400> SEQUENCE: 50
atccgtacct aaccatgacc c                                             21

<210> SEQ ID NO 51
<211> LENGTH: 20
<212> TYPE: DNA
<213> ORGANISM: artificial
<220> FEATURE:
<223> OTHER INFORMATION: primer

<400> SEQUENCE: 51
gcacagatct tggtggcttt                                               20

<210> SEQ ID NO 52
<211> LENGTH: 20
<212> TYPE: DNA
<213> ORGANISM: artificial
<220> FEATURE:
<223> OTHER INFORMATION: primer

<400> SEQUENCE: 52
ggctgggttt cccaaacgta                                               20

<210> SEQ ID NO 53
<211> LENGTH: 20
<212> TYPE: DNA
<213> ORGANISM: artificial
<220> FEATURE:
<223> OTHER INFORMATION: primer
```

```
<400> SEQUENCE: 53
caaactgctg tgttgggtgg                                              20

<210> SEQ ID NO 54
<211> LENGTH: 20
<212> TYPE: DNA
<213> ORGANISM: artificial
<220> FEATURE:
<223> OTHER INFORMATION: primer

<400> SEQUENCE: 54
acttggaagg gtccacacaa                                              20

<210> SEQ ID NO 55
<211> LENGTH: 24
<212> TYPE: DNA
<213> ORGANISM: artificial
<220> FEATURE:
<223> OTHER INFORMATION: primer

<400> SEQUENCE: 55
ccttgaatag agcattttc ccca                                          24

<210> SEQ ID NO 56
<211> LENGTH: 20
<212> TYPE: DNA
<213> ORGANISM: artificial
<220> FEATURE:
<223> OTHER INFORMATION: primer

<400> SEQUENCE: 56
tcctaccctt ggatggggtt                                              20

<210> SEQ ID NO 57
<211> LENGTH: 20
<212> TYPE: DNA
<213> ORGANISM: artificial
<220> FEATURE:
<223> OTHER INFORMATION: primer

<400> SEQUENCE: 57
gggctacacg gtccctaaag                                              20

<210> SEQ ID NO 58
<211> LENGTH: 23
<212> TYPE: DNA
<213> ORGANISM: artificial
<220> FEATURE:
<223> OTHER INFORMATION: target sequence

<400> SEQUENCE: 58
gtagccgggg aagcgaagca ggg                                          23

<210> SEQ ID NO 59
<211> LENGTH: 23
<212> TYPE: DNA
<213> ORGANISM: artificial
<220> FEATURE:
<223> OTHER INFORMATION: target sequence

<400> SEQUENCE: 59
gctcacggac ggctcctacc tgg                                          23

<210> SEQ ID NO 60
```

```
<211> LENGTH: 21
<212> TYPE: DNA
<213> ORGANISM: artificial
<220> FEATURE:
<223> OTHER INFORMATION: primer

<400> SEQUENCE: 60
ccccatcgtt ccatctcctc t                                                   21

<210> SEQ ID NO 61
<211> LENGTH: 22
<212> TYPE: DNA
<213> ORGANISM: artificial
<220> FEATURE:
<223> OTHER INFORMATION: primer

<400> SEQUENCE: 61
cgcgggttct tttggtatct tg                                                  22

<210> SEQ ID NO 62
<211> LENGTH: 84
<212> TYPE: DNA
<213> ORGANISM: artificial
<220> FEATURE:
<223> OTHER INFORMATION: primer

<400> SEQUENCE: 62
gtttaagagc tatgctgcga atacgagccg ccgaccagaa tcatgcaagt gcgtaagata         60
gtcgcgggtc ggcggctcgt attc                                                84

<210> SEQ ID NO 63
<211> LENGTH: 90
<212> TYPE: DNA
<213> ORGANISM: artificial
<220> FEATURE:
<223> OTHER INFORMATION: primer

<400> SEQUENCE: 63
aaaagcaccg actcggtgcc acttttccaa gttgataacg gactagcctt atttaaactt         60
gctatgctgc gaatacgagc cgccgacccg                                          90

<210> SEQ ID NO 64
<211> LENGTH: 60
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (21)..(40)
<223> OTHER INFORMATION: n is a, c, g, or t

<400> SEQUENCE: 64
ttaatacgac tcactatagg nnnnnnnnnn nnnnnnnnnn gtttaagagc tatgctgcga         60

<210> SEQ ID NO 65
<211> LENGTH: 90
<212> TYPE: DNA
<213> ORGANISM: artificial
<220> FEATURE:
<223> OTHER INFORMATION: primer

<400> SEQUENCE: 65
gtttaagagc tatgctggaa acagcatagc aagtttaaat aaggctagtc cgttatcaac         60
ttcgaatacg agatgcggcc gccgaccaga                                          90
```

```
<210> SEQ ID NO 66
<211> LENGTH: 96
<212> TYPE: DNA
<213> ORGANISM: artificial
<220> FEATURE:
<223> OTHER INFORMATION: primer

<400> SEQUENCE: 66
aaaaaaagca ccgactcggt gccactttt ccgaatacga gatgcggccg ccgacccgcg      60
actatcttac gcacttgcat gattctggtc ggcggc                              96

<210> SEQ ID NO 67
<211> LENGTH: 90
<212> TYPE: DNA
<213> ORGANISM: artificial
<220> FEATURE:
<223> OTHER INFORMATION: primer

<400> SEQUENCE: 67
gtttaagagc tatgctggaa acagcatagc aagtttaaat aaggctagtc cgttatcaac      60
ttgaaaaagt ggcaccgagt cggtgccgaa                                      90

<210> SEQ ID NO 68
<211> LENGTH: 96
<212> TYPE: DNA
<213> ORGANISM: artificial
<220> FEATURE:
<223> OTHER INFORMATION: protospacer

<400> SEQUENCE: 68
aaaaaaacga atacgagatg cggccgccga cccgcgacta tcttacgcac ttgcatgatt      60
ctggtcggcg gccgcatctc gtattcggca ccgact                              96

<210> SEQ ID NO 69
<211> LENGTH: 20
<212> TYPE: DNA
<213> ORGANISM: artificial
<220> FEATURE:
<223> OTHER INFORMATION: protospacer

<400> SEQUENCE: 69
aaaagcaccg actcggtgcc                                                 20

<210> SEQ ID NO 70
<211> LENGTH: 174
<212> TYPE: RNA
<213> ORGANISM: artificial
<220> FEATURE:
<223> OTHER INFORMATION: sgRNA
<220> FEATURE:
<221> NAME/KEY: misc_feature
<222> LOCATION: (1)..(20)
<223> OTHER INFORMATION: n is a, c, g, or u

<400> SEQUENCE: 70
nnnnnnnnnn nnnnnnnnnn guuuaagagc uaugcugcga auacgagccg ccgaccagaa      60
ucaugcaagu gcguaagaua gucgcggguc ggcggcucgu auucgcagca uagcaaguuu     120
aaauaaggcu aguccguuau caacuugaaa aaguggcacc gagucggugc uuuu           174

<210> SEQ ID NO 71
<211> LENGTH: 20
<212> TYPE: DNA
```

```
<213> ORGANISM: artificial
<220> FEATURE:
<223> OTHER INFORMATION: protospacer

<400> SEQUENCE: 71
gctgaagcac tgcacgccat                                              20

<210> SEQ ID NO 72
<211> LENGTH: 20
<212> TYPE: DNA
<213> ORGANISM: artificial
<220> FEATURE:
<223> OTHER INFORMATION: protospacer

<400> SEQUENCE: 72
ggagccgtac atgaactgag                                              20

<210> SEQ ID NO 73
<211> LENGTH: 20
<212> TYPE: DNA
<213> ORGANISM: artificial
<220> FEATURE:
<223> OTHER INFORMATION: protospacer

<400> SEQUENCE: 73
ctcgttgtcc aggtaggccc                                              20

<210> SEQ ID NO 74
<211> LENGTH: 20
<212> TYPE: DNA
<213> ORGANISM: artificial
<220> FEATURE:
<223> OTHER INFORMATION: protospacer

<400> SEQUENCE: 74
tggaccacca gctcctgtgg                                              20
```